US009783509B2

(12) United States Patent
Alig et al.

(10) Patent No.: US 9,783,509 B2
(45) Date of Patent: Oct. 10, 2017

(54) SIX-MEMBERED C-N-LINKED ARYL SULFIDE DERIVATIVES AND ARYL SULFOXIDE DERIVATIVES AS PEST CONROL AGENTS

(71) Applicant: BAYER CROPSCIENCE AKTIENGESELLSCHAFT, Monheim am Rhein (DE)

(72) Inventors: Bernd Alig, Königswinter (DE); Silvia Cerezo-Galvez, Langenfeld (DE); Reiner Fischer, Monheim (DE); Adeline Köhler, Langenfeld (DE); Julia Johanna Hahn, Düsseldorf (DE); Kerstin Ilg, Köln (DE); Peter Lösel, Leverkusen (DE); Olga Malsam, Rösrath (DE); Daniela Portz, Vettweiß (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/903,426

(22) PCT Filed: Jul. 4, 2014

(86) PCT No.: PCT/EP2014/064352
§ 371 (c)(1),
(2) Date: Jan. 7, 2016

(87) PCT Pub. No.: WO2015/004028
PCT Pub. Date: Jan. 15, 2015

(65) Prior Publication Data
US 2016/0251321 A1    Sep. 1, 2016

(30) Foreign Application Priority Data

Jul. 8, 2013    (EP) .................................... 13175501

(51) Int. Cl.
| | |
|---|---|
| *C07D 239/54* | (2006.01) |
| *C07D 239/553* | (2006.01) |
| *C07D 239/557* | (2006.01) |
| *C07D 251/20* | (2006.01) |
| *C07D 251/26* | (2006.01) |
| *C07D 253/075* | (2006.01) |
| *C07D 257/08* | (2006.01) |
| *A01N 43/54* | (2006.01) |
| *A01N 43/64* | (2006.01) |
| *A01N 43/707* | (2006.01) |
| *A01N 43/713* | (2006.01) |
| *C07D 401/04* | (2006.01) |

(52) U.S. Cl.
CPC ......... *C07D 253/075* (2013.01); *A01N 43/54* (2013.01); *A01N 43/64* (2013.01); *A01N 43/707* (2013.01); *A01N 43/713* (2013.01); *C07D 239/54* (2013.01); *C07D 239/553* (2013.01); *C07D 239/557* (2013.01); *C07D 251/20* (2013.01); *C07D 251/26* (2013.01); *C07D 257/08* (2013.01); *C07D 401/04* (2013.01)

(58) Field of Classification Search
CPC ...... A01N 43/54; A01N 43/707; A01N 43/64; A01N 43/58; A01N 43/713; A01N 43/40; C07D 401/04; C07D 253/075; C07D 239/54; C07D 239/557; C07D 251/30; C07D 251/38; C07D 237/16; C07D 237/18; C07D 239/553; C07D 239/58; C07D 253/04; C07D 257/08; C07D 213/69; C07D 213/70; C07D 251/20; C07D 251/26
See application file for complete search history.

(56) References Cited

U.S. PATENT DOCUMENTS

| | | | | |
|---|---|---|---|---|
| 4,906,287 | A * | 3/1990 | Lyga | A01N 43/707 504/178 |
| 6,159,903 | A | 12/2000 | Linker et al. | |
| 6,509,354 | B1 * | 1/2003 | Toriyabe | A01N 31/08 514/222.2 |

FOREIGN PATENT DOCUMENTS

| | | |
|---|---|---|
| DE | 2543497 A1 | 4/1977 |
| DE | 2724673 A1 | 12/1978 |
| DE | 19528305 A1 | 2/1997 |
| DE | 19536842 A1 | 3/1997 |
| EP | 1 803 712 A1 | 4/2007 |
| GB | 2021098 A | 11/1979 |
| JP | WO 2013/027660 A1 * 2/2013 ............ A01N 43/40 |
| WO | 8 600 072 A1 | 1/1986 |
| WO | 9730980 A1 | 8/1997 |
| WO | 9959983 A1 | 11/1999 |
| WO | 2005112941 A2 | 12/2005 |

OTHER PUBLICATIONS

International Search Report of PCT/EP2014/064352 dated Aug. 5, 2014.

* cited by examiner

*Primary Examiner* — John Pak
*Assistant Examiner* — Nathan W Schlientz
(74) *Attorney, Agent, or Firm* — McBee Moore Woodward & Vanik IP, LLC; Susan McBee; David Woodward

(57) ABSTRACT

The present invention relates to novel heterocyclic compounds, to processes for preparation thereof and to the use thereof for controlling animal pests, which include arthropods and especially insects and acarids.

18 Claims, No Drawings

SIX-MEMBERED C-N-LINKED ARYL SULFIDE DERIVATIVES AND ARYL SULFOXIDE DERIVATIVES AS PEST CONROL AGENTS

CROSS REFERENCE TO RELATED APPLICATIONS

This application is a §371 National Stage Application of PCT/EP2014/064352, filed 4 Jul. 2014, which claims priority to EP 13175501.9, filed 8 Jul. 2013.

BACKGROUND

Field of the Invention

The present invention relates to novel heterocyclic compounds, to processes for preparation thereof and to the use thereof for controlling animal pests, which include arthropods and especially insects.

Description of Related Art

2-Aryl-1,2,4-triazine-3,5-diones (including 1-aryl-6-azauracils) are already known in the literature with herbicidal, antiprotozoic, anthelmintic, antiinfective and insecticidal action, for example in WO 8600072, WO 9730980 and WO 2005/112941.

2-Aryl-1,2,4-triazine-3,5-dithiones are disclosed in WO 9730980 as herbicides. 6-Aryl-3-thioxo-5-(thi)oxo-1,2,4-triazines are disclosed, for example, in WO 9959983 as herbicides.

Identically 1,3-disubstituted 1,3,5-triazine-2,4-diones are described, for example, in DE 2543497 and DE 2724673 with insecticidal action.

Also disclosed are various substituted 1-aryl- and 1-pyridyluracils, which have fungicidal (GB 2021098) or herbicidal (DE 19528305) action, or which are described in general terms as pesticides (DE 19536842).

Crop protection agents, which also include pesticides, have to meet many demands, for example in relation to efficacy, persistence, and spectrum of action and possible use. Questions of toxicity and of combinability with other active ingredients or formulation auxiliaries play a role, as does the question of the expense that the synthesis of an active ingredient requires. In addition, resistances can occur. For all these reasons, the search for novel crop protection compositions cannot be considered to be complete, and there is a constant need for novel compounds having properties which, compared to the known compounds, are improved at least in relation to individual aspects.

SUMMARY

It was an object of the present invention to provide compounds which widen the spectrum of the pesticides in various respects.

This object, and further objects which are not stated explicitly but can be discerned or derived from the connections discussed herein, are achieved by novel compounds of the formula (I)

in which
D is a substructure of the formula (I-A)

in which the nitrogen is bonded to the six-membered ring in formula (I) and the arrow represents the bond to this six-membered ring, $V^1$, $V^2$ are each independently an oxygen, a sulphur or a substituted nitrogen;
$Q^1$ is a substituted carbon or substituted nitrogen;
$Q^3$ is a substituted carbon or nitrogen;
$Q^4$ is a substituted carbon or nitrogen;
W is hydrogen or halogen;
n is the number 0, 1 or 2;
X, Y and Z are each independently
  hydrogen, halogen, hydroxyl, amino, cyano, nitro, OCN, SCN, $SF_5$; or
  trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulphinyl, haloalkylsulphinyl, alkoxyalkylsulphinyl, alkylsulphinylalkyl, alkylsulphonyl, halo alkylsulphonyl, alkoxyalkylsulphonyl, alkylsulphonylalkyl, alkylsulphonyloxy, alkylcarbonyl, haloalkylcarbonyl, carboxyl, alkylcarbonyloxy, alkoxycarbonyl, haloalkoxycarbonyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl, where all the aforementioned radicals may optionally be substituted; or
  phenylalkyl, phenoxy, phenylalkyloxy, phenoxyalkyl, phenylthio, phenylthioalkyl, phenylsulphinyl, phenylsulphonyl, hetarylalkyl, hetaryloxy, hetarylalkyloxy, hetarylthio, hetarylsulphinyl or hetarylsulphonyl, where all the aforementioned radicals may optionally be substituted; or
  cycloalkylalkyl, cycloalkyloxy, cycloalkylalkoxy, cycloalkylthio, cycloalkylalkylthio, cycloalkylsulphinyl, cycloalkylalkylsulphinyl, cycloalkylsulphonyl, cycloalkylalkylsulphonyl or cycloalkenyl, where all the aforementioned radicals may each optionally be substituted; or
  NR'R"
    where R' and R" are each independently
      hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl; or
    R' and R" together with the nitrogen atom to which they are bonded may form an optionally substituted, saturated or unsaturated five- to eight-membered ring optionally interrupted by one or more heteroatoms which are selected independently from the group consisting of O, S and N; or are a 3- to 6-membered saturated, partly saturated or aromatic ring which may optionally contain one to three heteroatoms which are selected independently from the group consisting of O, S and N, and which may optionally be substituted;

or X and Z, or Y and Z, together with the carbon atoms to which they are bonded, form a 5- or 6-membered ring which is optionally substituted and optionally interrupted by one or more heteroatoms which are selected independently from the group consisting of O, S, N and CO.

It has been additionally found that the novel compounds of the formula (I) have good efficacy as pesticides, for example against arthropods and especially insects and acarids, and additionally generally have very good compatibility with plants, especially crop plants, and/or have favourable toxicological and/or environmentally relevant properties.

DETAILED DESCRIPTION OF A PREFERRED EMBODIMENT

Preferred substituents or ranges for the radicals shown in the compounds of the formula (I) are elucidated below.

D is a substructure of the formula (I-A);

$V^1$, $V^2$ are each independently an oxygen, sulphur or N—$R^{11}$, especially oxygen;

$Q^1$ is $CR^2R^7$ or N—$R^1$, especially N—$R^1$;

$Q^3$ is $CR^4$ or nitrogen, especially $CR^4$;

$Q^4$ is $CR^5$ or nitrogen;

$R^1$ is hydrogen, cyano or nitro;

or alkyl, cycloalkylalkyl, haloalkyl, cyanoalkyl, hydroxyalkyl, alkoxyalkyl, aminoalkyl, alkoxycarbonylalkyl, alkylthioalkyl, haloalkylthioalkyl, alkylsulphinylalkyl, haloalkylsulphinylalkyl, alkylsulphonylalkyl, haloalkylsulphonylalkyl, phenylalkyl, phenoxyalkyl, phenylsulphanylalkyl, phenylsulphinylalkyl, phenylsulphonylalkyl, hetarylalkyl, hetaryloxyalkyl, hetarylthioalkyl, where the aforementioned radicals may each be saturated or unsaturated and/or optionally substituted, and where one of the nitrogen atoms present in hetarylalkyl, hetaryloxyalkyl and hetarylthioalkyl may also be in the form of the N-oxide;

or optionally substituted saturated or unsaturated cycloalkyl which may optionally be interrupted by one or more heteroatoms;

or hydroxyl, alkoxy or haloalkoxy;

or alkylcarbonyl, haloalkylcarbonyl, hydroxyalkylcarbonyl, alkoxyalkylcarbonyl, phenylcarbonyl, hetarylcarbonyl, alkoxycarbonyl, halo alkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl (aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or is carbonyl or carboxyl; or or optionally substituted phenyl or optionally substituted hetaryl, where one of the nitrogen atoms present in hetaryl may also be in the form of the N-oxide;

or alkoxy, haloalkoxy, cycloalkyloxy, aryloxy, arylalkyloxy or carbonyloxy, where the aforementioned radicals may optionally be substituted, or hydroxyl;

or alkylamino, haloalkylamino, dihaloalkylamino, dialkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulphonylamino, or arylsulphonylamino, where the aforementioned radicals may each be saturated or unsaturated and/or optionally substituted, or amino;

or aminosulphonyl, alkylaminosulphonyl, dialkylaminosulphonyl or arylaminosulphonyl, where the aforementioned radicals may each be saturated or unsaturated and/or optionally substituted;

$R^2$ and $R^7$ are each independently hydrogen, cyano, halogen or nitro;

or alkyl, cycloalkylalkyl, haloalkyl, cyanoalkyl, hydroxyalkyl, alkoxyalkyl, aminoalkyl, alkoxycarbonylalkyl, alkylsulphanylalkyl, alkylsulphinylalkyl, alkylsulphonylalkyl, halo alkylsulphanylalkyl, haloalkylsulphinylalkyl, haloalkylsulphonylalkyl, alkoxyalkylsulphanylalkyl, alkoxyalkylsulphinylalkyl, alkoxyalkylsulphonylalkyl, phenylalkyl, phenoxyalkyl, phenylsulphanylalkyl, phenylsulphinylalkyl, phenylsulphonylalkyl, hetarylalkyl, hetaryloxyalkyl, hetarylthioalkyl, where the aforementioned radicals may each be saturated or unsaturated and/or optionally substituted;

or optionally substituted saturated or unsaturated cycloalkyl which may optionally be interrupted by one or more heteroatoms;

or alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl (aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or carbonyl or carboxyl;

or optionally substituted phenyl or optionally substituted hetaryl;

or alkoxy, haloalkoxy, alkoxyalkoxy, aryloxy, arylalkyloxy, cycloalkyloxy, cycloalkylalkyloxy or carbonyloxy, where the aforementioned radicals may be saturated or unsaturated and/or optionally substituted, or hydroxyl;

or alkylamino, dialkylamino, haloalkylamino, dihalodialkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulphonylamino, or arylsulphonylamino, where the aforementioned radicals may each be saturated or unsaturated and/or optionally substituted, or amino;

or alkylsulphanyl, alkylsulphinyl, alkylsulphonyl, haloalkylsulphanyl, haloalkylsulphinyl, haloalkylsulphonyl, cycloalkylsulphanyl, cycloalkylsulphinyl, cycloalkylsulphonyl, cycloalkylalkylsulphanyl, cycloalkylalkylsulphinyl, cycloalkylalkylsulphonyl, arylsulphanyl, arylsulphinyl, arylsulphonyl, arylalkylsulphanyl, arylalkylsulphinyl, arylalkylsulphonyl, aminosulphonyl, alkylaminosulphonyl, dialkylaminosulphonyl or arylaminosulphonyl, where the aforementioned radicals may each be saturated or unsaturated and/or optionally substituted, or sulphanyl;

or $R^2$ and $R^7$ may, together with the atom to which they are bonded, form an optionally substituted, saturated or unsaturated three- to eight-membered ring optionally interrupted by one or more heteroatoms which are selected independently from the group consisting of O, S and N;

or $R^2$ is a saturated or unsaturated cycle optionally interrupted by one or more heteroatoms which are each selected from the group consisting of O, S and N, which may optionally be substituted;

where $R^2$ and $R^7$ are especially each independently hydrogen, cyano, halogen or nitro;

or $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated;

or optionally substituted saturated or unsaturated $(C_3-C_6)$cycloalkyl which may optionally be interrupted by one or more heteroatoms;

or $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or carbonyl or carboxyl;

or optionally substituted phenyl or optionally substituted hetaryl;

or $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or hydroxyl;

or $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkyl amino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or amino;

or $(C_1-C_6)$alkylsulphanyl, $(C_1-C_6)$alkyl sulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cyclo alkyl$(C_1-C_6)$alkylsulphanyl, $(C_3-C_6)$cycloalkyl$(C_1-C_6)$alkylsulphinyl, $(C_3-C_6)$cyclo alkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or sulphanyl;

or $R^2$ and $R^7$ together with the atom to which they are bonded form an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

$R^4$ and $R^5$ are each independently
hydrogen, hydroxy, halogen, cyano, nitro, alkyl, cycloalkyl, haloalkyl, cyanoalkyl, alkoxy, haloalkoxy, alkylthio, haloalkylthio, alkylsulphinyl, haloalkylsulphinyl, alkylsulphonyl, haloalkylsulphonyl, amino, thiol, carboxyl, monoalkylamino or dialkylamino;

$R^{11}$ is hydrogen, hydroxyl, cyano, alkyl, cycloalkyl, haloalkyl, cyanoalkyl, alkoxy, haloalkoxy, alkylthio, haloalkylthio, alkylsulphinyl, haloalkylsulphinyl, alkylsulphonyl, haloalkylsulphonyl, amino, monoalkylamino or dialkylamino;

W is hydrogen or halogen;

n is the number 0 or 1;

X, Y and Z are each independently hydrogen, fluorine, chlorine, bromine, cyano, nitro, amino, hydroxyl, alkyl, haloalkyl, alkenyl, alkynyl, alkoxy, haloalkoxy or aminothiocarbonyl;

or benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluorometphoxy, trifluoroethoxy, or optionally methyl-, fluorine-, chlorine-, cyano-substituted cyclopropyl;

or cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy, or optionally methyl-, fluorine-, chlorine-, cyano-substituted cyclopropyl.

Further preferred substituents or ranges for the radicals shown in the compounds of the formula (I) are elucidated below.

D is a substructure of the formula (I-A);

$V^1$, $V^2$ are each independently an oxygen or $N—R^{11}$, especially oxygen;

$Q^1$ is $N—R^1$;

$Q^3$ is $CR^4$ or nitrogen;

$Q^4$ is $CR^5$ or nitrogen;

$R^1$ is hydrogen;

or $(C_1-C_6)$alkyl, $(C_3-C_8)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

or $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^4$ and $R^5$ are each independently hydrogen, halogen, $(C_1-C_4)$alkyl, $(C_1-C_4)$haloalkyl, cyano$(C_1-C_6)$alkyl, $(C_3-C_6)$cycloalkyl, cyano or carboxyl;

$R^{11}$ is hydrogen, $(C_1-C_4)$alkyl, $(C_1-C_4)$haloalkyl, cyano$(C_1-C_6)$alkyl or $(C_3-C_6)$cycloalkyl;

where $R^{11}$ is especially hydrogen, methyl, ethyl, tert-butyl, trifluoromethyl, methoxy, trifluoromethoxy or cyclopropyl; and more preferably hydrogen, methyl or trifluoroethyl;

W is hydrogen or fluorine;

n is the number 0 or 1;

X and Y are each independently hydrogen, fluorine, chlorine, bromine, methyl, ethyl, trifluoromethyl, difluoromethyl, difluoromethoxy, trifluoromethoxy, cyclopropyl, cyano, amino, hydroxyl or nitro;

Z is hydrogen.

Likewise further preferred substituents or ranges for the radicals shown in the compounds of the formula (I) are elucidated below.

D is a substructure of the formula (I-A);

$V^1$, $V^2$ are each independently an oxygen or $N—R^{11}$, especially oxygen;

$Q^1$ is $N—R^1$;

$Q^3$ is $CR^4$ or nitrogen;

$Q^4$ is $CR^5$ or nitrogen;

$R^1$ is hydrogen;

or $(C_1-C_6)$alkyl, $(C_3-C_8)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl, phenyl$(C_1-C_3)$alkyl or pyridyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl, and where the nitrogen atom present in pyridyl$(C_1-C_3)$alkyl may also be in the form of the N-oxide;

or $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyridyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, optionally methyl-, fluorine-, chlorine-, cyano-substituted cyclopropyl, and where the nitrogen atom present in pyridyl may also be in the form of the N-oxide;

$R^4$ and $R^5$ are each independently hydrogen, halogen, $(C_1-C_4)$alkyl, $(C_1-C_4)$haloalkyl, cyano$(C_1-C_6)$alkyl, $(C_3-C_6)$cycloalkyl, cyano or carboxyl;

$R^{11}$ is hydrogen, $(C_1-C_4)$alkyl, $(C_1-C_4)$haloalkyl, cyano$(C_1-C_6)$alkyl or $(C_3-C_6)$cycloalkyl;

where $R^{11}$ is especially hydrogen, methyl, ethyl, tert-butyl, trifluoromethyl, methoxy, trifluoromethoxy or cyclopropyl; and more preferably hydrogen, methyl or trifluoroethyl;

W is hydrogen or fluorine;

n is the number 0 or 1;

X and Y are each independently hydrogen, fluorine, chlorine, bromine, methyl, ethyl, trifluoromethyl, difluoromethyl, difluoromethoxy, trifluoromethoxy, cyclopropyl, cyano, amino, hydroxyl or nitro;

Z is hydrogen.

Particularly preferred substituents or ranges for the radicals shown in the compounds of the formula (I) are elucidated below.

D is a substructure of the formula (I-A);

$V^1$, $V^2$ are each independently an oxygen;

$Q^1$ is $N—R^1$;

$Q^3$ is $CR^4$;

$Q^4$ is $CR^5$ or nitrogen;

$R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, trifluoroethyl, 2,2-difluoroethyl, $CH_2CN$, $CH_2CH_2OCH_3$, benzyl, cyclopropyl, cyclobutyl or phenyl;

$R^4$ and $R^5$ are each independently hydrogen, methyl, ethyl, tert-butyl, trifluoromethyl, methoxy, trifluoromethoxy, cyclopropyl, cyano or carboxyl;

W is hydrogen or fluorine;

n is the number 0 or 1;

X is hydrogen, chlorine, fluorine, methyl or ethyl;
Y is chlorine, bromine, cyano, methyl, ethyl, trifluoromethyl, fluorine or methoxy;
Z is hydrogen.

It is further preferred among these particularly preferred substituents or ranges that X and Y represent the following combinations (Y,X): (Me,F), (Me,H), (Me,Cl), (Me,Me), (Et,Et), (Cl,Cl), (Cl,F), (CN,F), (MeO,F), (MeO,H), (Cl,H), (Me,H), (Br,H), (Br,F), (CN,H), (F,F), (CF$_3$,H).

Likewise very particularly preferred substituents or ranges of the radicals shown in the compounds of the formula (I) are elucidated below.
D is a substructure of the formula (I-A);
$V^1$, $V^2$ are each independently an oxygen;
$Q^1$ is N—$R^1$;
$Q^3$ is CR$^4$;
$Q^4$ is CR$^5$ or nitrogen;
$R^1$ is hydrogen, methyl, ethyl, n-propyl, CH(CH$_3$)$_2$, n-butyl, sec-butyl, C(CH$_3$)$_3$, CH$_2$C(CH$_3$)$_3$, CH$_2$CH(CH$_3$)$_2$, CH$_2$CH=CH$_2$, CH$_2$CCH, cyclopropylmethyl, trifluoroethyl, 2,2-difluoroethyl, CH$_2$CN, CH$_2$OCH$_3$, CH$_2$CH$_2$OCH$_3$, benzyl, cyclopropyl, cyclobutyl, phenyl, 2-fluorophenylmethyl, 3-fluorophenylmethyl, 4-fluorophenylmethyl, 2-pyridylmethyl, N-oxide-2-pyridylmethyl, 3-pyridylmethyl, N-oxide-3-pyridylmethyl, 4-pyridylmethyl or N-oxide-4-pyridylmethyl;
$R^4$ and $R^5$ are each independently
hydrogen, methyl, ethyl, tert-butyl, trifluoromethyl, methoxy, trifluoromethoxy, cyclopropyl, cyano or carboxyl;
W is hydrogen or fluorine;
n is the number 0 or 1;
X is hydrogen, chlorine, fluorine, methyl or ethyl;
Y is chlorine, bromine, cyano, methyl, ethyl, trifluoromethyl, fluorine or methoxy;
Z is hydrogen.

It is further preferred among these particularly preferred substituents or ranges that X and Y represent the following combinations (Y,X): (Me,F), (Me,H), (Me,Cl), (Me,Me), (Et,Et), (Cl,Cl), (Cl,F), (CN,F), (MeO,F), (MeO,H), (Cl,H), (Me,H), (Br,H), (Br,F), (CN,H), (F,F), (CF$_3$,H).

Very particularly preferred substituents or ranges of the radicals shown in the compounds of the formula (I) are elucidated below.
D is a substructure of the formula (I-A);
$V^1$, $V^2$ are each independently an oxygen;
$Q^1$ is N—$R^1$;
$Q^3$ is CR$^4$;
$Q^4$ is CR$^5$ or nitrogen;
$R^1$ is hydrogen, methyl, trifluoroethyl;
$R^4$ and $R^5$ are each independently hydrogen, cyano or methyl;
W is hydrogen or fluorine;
n is the number 0 or 1;
X is chlorine, fluorine, methyl or ethyl;
X is chlorine, methyl or ethyl;
Z is hydrogen.

It is further preferred among these very particularly preferred substituents or ranges that X and Y represent the following combinations (Y,X): (Me,F), (Me,Me), (Cl,Cl), (Et,Et).

Likewise very particularly preferred substituents or ranges of the radicals shown in the compounds of the formula (I) are elucidated below.
D is a substructure of the formula (I-A);
$V^1$, $V^2$ are each independently an oxygen;
$Q^1$ is N—$R^1$;
$Q^3$ is CR$^4$;
$Q^4$ is CR$^5$ or nitrogen;
$R^1$ is hydrogen, methyl, ethyl, n-propyl, CH(CH$_3$)$_2$, CH$_2$CH(CH$_3$)$_2$, CH$_2$CH=CH$_2$, CH$_2$CCH, cyclopropylmethyl, trifluoroethyl, 2,2-difluoroethyl, CH$_2$CN, CH$_2$OCH$_3$, benzyl, 4-fluorophenylmethyl, 3-pyridylmethyl or N-oxide-3-pyridylmethyl;
$R^4$ and $R^5$ are each independently hydrogen, cyano or methyl;
W is hydrogen or fluorine;
n is the number 0 or 1;
X is hydrogen, chlorine, fluorine, methyl or ethyl;
X is chlorine, methyl or ethyl;
Z is hydrogen.

It is further preferred among these very particularly preferred substituents or ranges that X and Y represent the following combinations (Y,X): (Me,F), (Me,Me), (Cl,Cl), (Et,Et), (Me,H), (Cl,H).

When sulphur and/or nitrogen occur in rings in the above definitions, for example in expressions such as "in which the rings may contain at least one heteroatom from the group of sulphur, oxygen (where oxygen atoms must not be directly adjacent) and nitrogen" or "in which one or two ring members may each be replaced by a heteroatom from the group of sulphur, oxygen (where oxygen atoms must not be directly adjacent) and nitrogen", unless stated otherwise, the sulphur may also be present in the form of SO or SO$_2$; the nitrogen, if it is not in the form of —N=, as well as NH, may also be in the form of N-alkyl (especially N—C$_1$-C$_6$-alkyl).

In the broadest and the preferred definitions, unless stated otherwise,
halogen is selected from the group of fluorine, chlorine, bromine and iodine, preferably in turn from the group of fluorine, chlorine and bromine,
hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

In the further preferred definitions, unless stated otherwise,
halogen is selected from the group of fluorine, chlorine, bromine and iodine, preferably in turn from the group of fluorine, chlorine and bromine, and
hetaryl (synonymous with heteroaryl, including as part of a larger unit, for example hetarylalkyl) is selected from the group of pyridyl, pyrimidyl, pyridazinyl and pyrazinyl, preferably pyridyl, Halogen-substituted radicals, for example haloalkyl, are mono- or polyhalogenated, up to the maximum number of possible substituents. In the case of polyhalogenation, the halogen atoms may be the same or different. Halogen is fluorine, chlorine, bromine and iodine, especially fluorine, chlorine and bromine.

Saturated or unsaturated hydrocarbon radicals, such as alkyl or alkenyl, may each be straight-chain or branched if possible, including in combination with heteroatoms, as, for example, in alkoxy.

Optionally substituted radicals may be mono- or polysubstituted, where the substituents in the case of polysubstitution may be the same or different.

The radical definitions or elucidations given above in general terms or within areas of preference apply correspondingly to the end products (including the compounds of the formula (I) with the substructures (I-A-I) to (I-A-III), and also (I-A-1), (I-A-5) and (I-A-9), which will be elucidated later), and to the starting materials and intermediates. These radical definitions can be combined with one another as desired, i.e. including combinations between the respective preferred ranges.

Preference is given in accordance with the invention to compounds of the formula (I) in which a combination of the definitions given above as preferred is present, and every configuration described above as preferred constitutes an independent combination.

Further preference is given in accordance with the invention to compounds of the formula (I) in which a combination of the definitions given above as further preferred is present, and every configuration described above as further preferred constitutes an independent combination.

Particular preference is given in accordance with the invention to compounds of the formula (I) in which a combination of the definitions given above as particularly preferred is present, and every configuration described above as particularly preferred constitutes an independent combination.

Very particular preference is given in accordance with the invention to compounds of the formula (I) in which a combination of the definitions given above as very particularly preferred is present, and every configuration described above as very particularly preferred constitutes an independent combination.

In a preferred embodiment, the invention relates to compounds of the formula (I) in which D is a substructure of the formula (I-A-I):

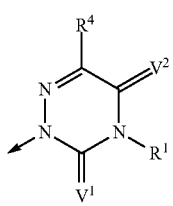

(I-A-I)

In a further preferred embodiment, the invention relates to compounds of the formula (I) in which D is a substructure of the formula (I-A-II):

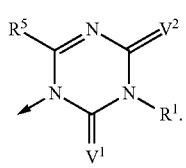

(I-A-II)

In a further preferred embodiment, the invention relates to compounds of the formula (I) in which D is a substructure of the formula (I-A-III):

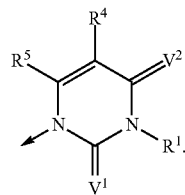

(I-A-III)

In the compounds of the formula (I) defined by the structures (I-A-I) to (I-A-III), the radicals or structural elements $V^1$, $V^2$, $R^1$, $R^4$, $R^5$, W, n, X, Y and Z are each as defined above.

More particularly, X and Y represent the following (Y,X) combinations: (Me,F), (Me,H), (Me,Cl), (Me,Me), (Et,Et), (Cl,Cl), (Cl,F), (CN,F), (MeO,F), (MeO,H), (Cl,H), (Br,H), (Br,F), (CN,H), (F,F), (CF$_3$,H), particular preference being given to the following (Y,X) combinations: (Me,F), (Me,Me), (Cl,Cl), (Et,Et), (Me,H), (Cl,H).

In a further preferred configuration of embodiment (I-A-I), the invention relates to compounds of the formula (I) in which D is a substructure of the formula (I-A-1):

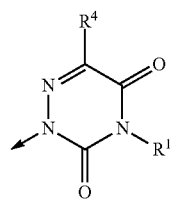

(I-A-1)

In a further preferred configuration of embodiment (I-A-II), the invention relates to compounds of the formula (I) in which D is a substructure of the formula (I-A-5):

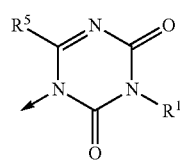

(I-A-5)

In a further preferred configuration of embodiment (I-A-III), the invention relates to compounds of the formula (I) in which D is a substructure of the formula (I-A-9):

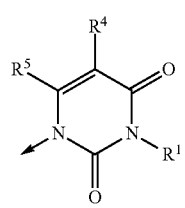

(I-A-9)

In the compounds of the formula (I) defined by the structures (I-A-1), (I-A-5) and (I-A-9), the radicals or structural elements $R^1$, $R^4$, $R^5$, W, n, X, Y and Z are as defined above.

More particularly, X and Y represent the following (Y,X) combinations: (Me,F), (Me,H), (Me,Cl), (Me,Me), (Et,Et), (Cl,Cl), (Cl,F), (CN,F), (MeO,F), (MeO,H), (Cl,H), (Br,H), (Br,F), (CN,H), (F,F), ($CF_3$,H), particular preference being given to the following (Y,X) combinations: (Me,F), (Me,Me), (Cl,Cl), (Et,Et), (Me,H), (Cl,H).

Within the embodiments in which D is a substructure of the formula (I-A-I), (I-A-II), (I-A-III), (I-A-1), (I-A-5) or (I-A-9), preference is given to those compounds in which a combination of the definitions given above as preferred is present, and every configuration described above as preferred constitutes an independent combination.

Within the embodiments in which D is a substructure of the formula (I-A-I), (I-A-II), (I-A-III), (I-A-1), (I-A-5) or (I-A-9), further preference is given to those compounds in which a combination of the definitions given above as further preferred is present, and every configuration described above as further preferred constitutes an independent combination.

Within the embodiments in which D is a substructure of the formula (I-A-I), (I-A-II), (I-A-III), (I-A-1), (I-A-5) or (I-A-9), particular preference is given to those compounds in which a combination of the definitions given above as particularly preferred is present, and every configuration described above as particularly preferred constitutes an independent combination.

Within the embodiments in which D is a substructure of the formula (I-A-I), (I-A-II), (I-A-III), (I-A-1), (I-A-5) or (I-A-9), very particular preference is given to those compounds in which a combination of the definitions given above as very particularly preferred is present, and every configuration described above as very particularly preferred constitutes an independent combination. In these compounds, especially in the embodiments in which D is a substructure of the formula (I-A-1), $R^1$ is hydrogen, methyl or trifluoroethyl;
$R^4$ is hydrogen;
W is fluorine;
n is the number 0 or 1;
X is chlorine, fluorine or methyl;
Y is chlorine or methyl;
where X and Y especially represent the following (Y,X) combinations: (Me,F), (Me,Me), (Cl,Cl);
Z is hydrogen,
or
$R^1$ is hydrogen, methyl, ethyl, $CH(CH_3)_2$, $CH_2CH(CH_3)_2$, cyclopropylmethyl, trifluoroethyl, $CH_2CN$, benzyl, 3-pyridylmethyl or N-oxide-3-pyridylmethyl;
$R^4$ is hydrogen;
W is fluorine;
n is the number 0 or 1;
X is hydrogen, chlorine, fluorine or methyl;
Y is chlorine or methyl;
where X and Y especially represent the following (Y,X) combinations: (Me,F), (Me,Me), (Cl,Cl), (Me,H), (Cl,H);
Z is hydrogen,
and, in embodiments in which D is a substructure of the formula (I-A-9),
$R^1$ is hydrogen;
$R^4$ is cyano;
$R^5$ is methyl,
W is fluorine;
n is the number 0 or 1;
X is fluorine or ethyl;
Y is methyl or ethyl;
where X and Y especially represent the following (Y,X) combinations: (Me,F), (Et,Et);
Z is hydrogen,
or
$R^1$ is hydrogen, methyl, ethyl, n-propyl, $CH(CH_3)_2$, $CH_2CH(CH_3)_2$, $CH_2CH=CH_2$, $CH_2CCH$, cyclopropylmethyl, trifluoroethyl, 2,2-difluoroethyl, $CH_2CN$, $CH_2OCH_3$ or 4-fluorophenylmethyl;
$R^4$ is hydrogen or cyano;
$R^5$ is hydrogen or methyl;
W is fluorine;
n is the number 0 or 1;
X is hydrogen, fluorine, methyl or ethyl;
Y is methyl or ethyl;
where X and Y especially represent the following (Y,X) combinations: (Me,F), (Et,Et), (Me,Me), (Me,H);
Z is hydrogen.

The inventive compounds of the formula (I) and the acid addition salts and metal salt complexes thereof have good efficacy, especially for controlling animal pests, which include arthropods and especially insects and acarids.

The compounds of the formula (I) may possibly also, depending on the nature of the substituents, be in the form of stereoisomers, i.e. in the form of geometric and/or optically active isomers or isomer mixtures of varying composition. This invention provides both the pure stereoisomers and any desired mixtures of these isomers, even though it is generally only compounds of the formula (I) that are discussed here.

However, preference is given in accordance with the invention to using the optically active, stereoisomeric forms of the compounds of the formula (I) and salts thereof.

The invention therefore relates both to the pure enantiomers and diastereomers and to mixtures thereof for controlling animal pests, including arthropods and especially insects and acarids. An individual configuration of the invention is therefore directed to the presence of the R enantiomer, or to a mixture comprising a majority of the R enantiomer, preferably where the ratio of R to S enantiomer is at least 60:40 and, with increasing preference, at least 70:30, 75:25, 80:20, 85:15 and 90:10. A further individual configuration of the invention is therefore directed to the presence of the S enantiomer, or to a mixture comprising a majority of the S enantiomer, preferably where the ratio of S to R enantiomer is at least 60:40 and, with increasing preference, at least 70:30, 75:25, 80:20, 85:15 and 90:10.

The inventive compounds of the formula (I) may be present in different polymorphic forms or as a mixture of different polymorphic forms. Both the pure polymorphs and the polymorph mixtures are provided by the invention and can be used according to the invention.

Suitable salts of the compounds of the general formula (I) include customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulphates, trihydrosulphates, or phosphates, salts with organic carboxylic acids or sulphonic acids, for example formates, acetates, trifluoroacetates, maleates, tartrates, methanesulphonates, benzenesulphonates or para-toluenesulphonates, salts with basic amino acids, for example arginates, aspartates or glutamates, and the like.

The inventive compounds are defined in general terms by the formula (I), which includes all the possible rotamers and mixtures thereof.

The inventive compounds of the formula (I) can be prepared by customary methods known to those skilled in the art. Various preparation methods, which likewise form part of the subject-matter of the invention, are described in the processes P1, P2, P3, P3', Pa1, Pa2, Pa3, Pa4 and Pa5 which follow.

Preparation Processes

The compounds of the general formula (I) can be divided into compounds with n=0 (Ia) and n=1 (Ib) and can in principle be prepared by the general processes P1, P2, P3 and P3'.

Process P1 includes all the methods which—usually in a multistage process—enable formation of the 5-membered ring, especially proceeding from the anilines of the general formula (IVa), according to the following scheme:

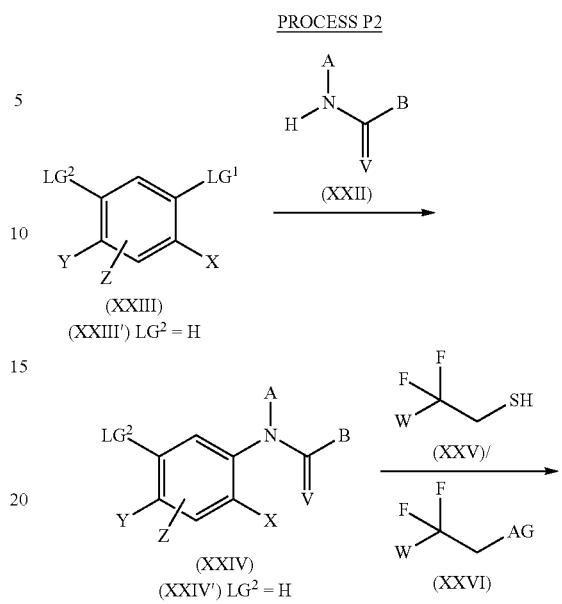

PROCESS P1

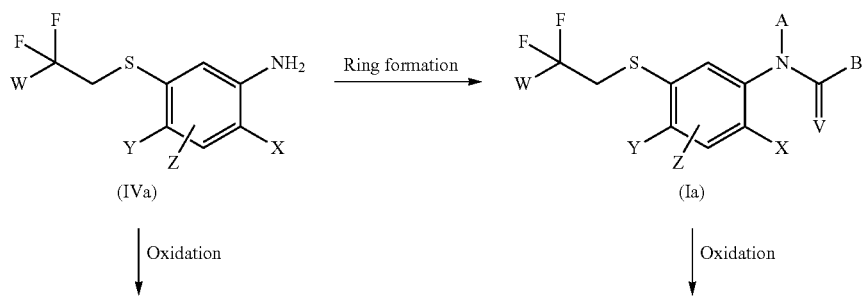

where X, Y, Z, A, B and V are as defined above.

By oxidation of the thioethers of the general formula (Ia) by methods known from the literature, it is possible to obtain the sulphoxides of the general formula (Ib).

Alternatively, some of the methods described in Process P1 can also be employed proceeding from sulphoxides of the general formula (IVb) to give the sulphoxides of the general formula (Ib). The sulphoxides of the formula (IVb) can be prepared from the sulphides (IVa) by methods known from the literature.

Alternatively, the compounds of the general formula (Ia) can also be prepared by Process P2, according to the following scheme:

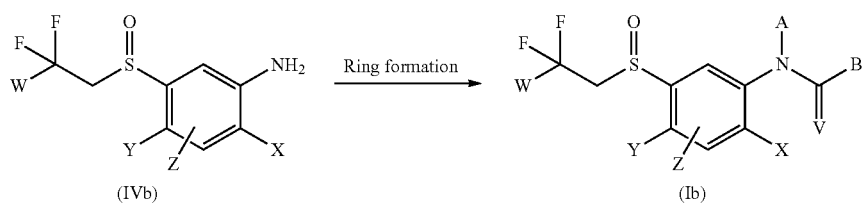

-continued

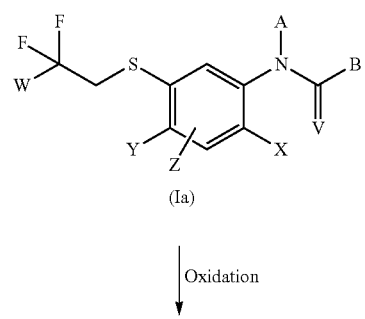

-continued

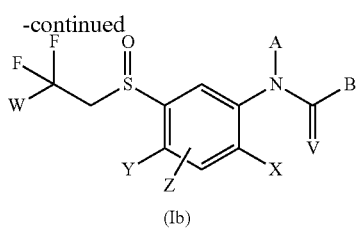

(Ib)

where Z, A, B, V and W are as defined above, X is hydrogen or an electron-withdrawing group (especially nitro, chlorine, fluorine, cyano), Y represents electron-withdrawing substituents (especially nitro, chlorine, fluorine, cyano), $LG^1$ represents typical leaving groups in nucleophilic substitution reactions (especially fluoride, chloride) and $LG^2$ may represent hydrogen or typical leaving groups in nucleophilic substitution reactions (especially fluoride, chloride).

The reaction of compounds of the general formula (XXIII) with heterocyclic compounds of the general formula (XXII), usually under basic reaction conditions as, for example, in DE 4431218 for pyrimidin(ethi)ones, WO 2009/012275 and WO 2008/155034 for pyridones or DE 19528305 for uracils, gives the compounds of the general formula (XXIV). Through another nucleophilic aromatic substitution with thiols of the general formula (XXV), the thioethers of the formula (Ia) can be prepared. Suitable reaction conditions for such reactions are described in WO 2007/131680 and WO 2008/086226.

By oxidation of the thioethers of the general formula (Ia) by methods known from the literature, it is possible to obtain the sulphoxides of the general formula (Ib).

Compounds of the formula (XXIII) in which $LG^2$ is hydrogen are referred to as (XXIII') and can be reacted in a manner similar to that described above with compounds of the formula (XXII), in this case to give compounds of the formula (XXIV').

Some compounds of the formula (XXIV') are commercially available.

The compounds of the formula (XXIV') can be converted in a multistage process to the inventive compounds (Ia). The steps required include chlorosulphonation, reduction and alkylation with haloalkyl electrophiles of the formula (XXVI), all possible by methods known from the literature. The chlorosulphonation of the compounds (XXIV') with chlorosulphonic acid gives the corresponding sulphonyl chlorides and these can be converted to their disulphides by methods known from the literature, for example iron in hydrochloric acid or iodide. The reaction of the disulphides with haloalkyl electrophiles of the formula (XXVI) gives the sulphides (Ia).

By oxidation of the thioethers of the general formula (Ia) by methods known from the literature, it is possible to obtain the sulphoxides of the general formula (Ib).

Process P2 is especially suitable for preparation of embodiment I-A in which X is hydrogen or represents electron-withdrawing substituents (especially nitro, chloride, fluoride, cyano) and Y represents electron-withdrawing substituents (especially nitro, chloride, fluoride, cyano).

Alternatively, the compounds of the general formula (Ia) can be prepared by Processes P3 and P3', as shown in the following scheme:

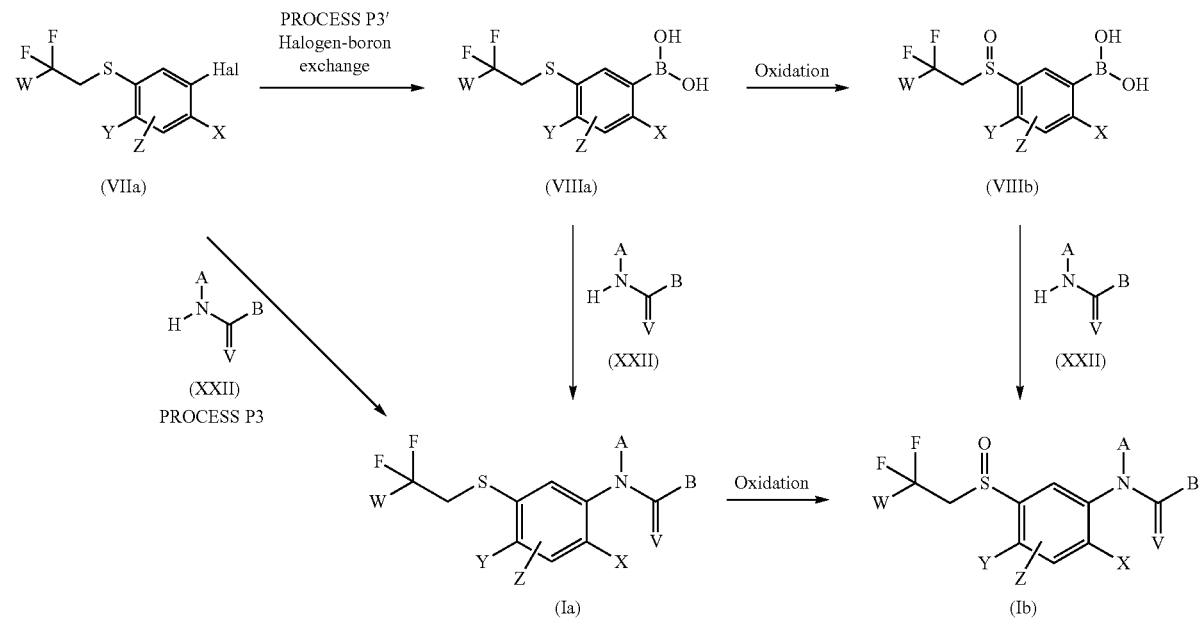

where X, Y, Z, W, A, B and V are as defined above and Hal is halogen (preferably chlorine, bromine, iodine).

According to Process P3, compounds of the general formula (Ia) can be prepared by methods known from the literature by reaction of aryl halides of the general formula (VIIa) with heterocyclic compounds of the general formula (XXII). The reaction preferably takes place through transition metal catalysis or mediation. Numerous illustrative sets of reaction conditions are known in the literature, for example in WO 2006/117657 A1, in US 2010/99725 A1 or in WO 2010/47956 A1. Preference is given to using copper or copper salts, for example copper(I) iodide, copper(I) oxide, copper(I) triflate or copper(II) triflate, as catalyst, frequently in the presence of a ligand, for example diamine ligands such as N,N'-dimethylethylenediamine, N,N-dimethylethylenediamine or trans-N,N'-dimethyl-1,2-cyclohexanediamine. A review can be found, for example, in Chem. Sci. 2010, vol. 1, 13-31. Alternatively, it is possible to use 1,3-diketones, for example 2,4-pentanedione, 2,2,6,6-tetramethyl-3,5-heptanedione or dibenzoylmethane, amino acids, for example L-proline or glycine, or other compounds such as 8-hydroxyquinoline (Tetrahedron Lett. 2009, vol. 50, 7293-7296), dibenzylideneacetone, bipyridine or phenanthroline. In general, the reaction is performed in the presence of a base, frequently carbonate or phosphate bases, for example potassium carbonate, sodium carbonate, caesium carbonate or potassium phosphate, in suitable solvents, for example dioxane, toluene, dimethyl sulphoxide or N,N-dimethylformamide. It is additionally possible to use other additives, for example potassium iodide, caesium fluoride or other salts.

Alternatively, it is possible to perform reactions of this kind under palladium catalysis, for instance using catalysts, for example palladium acetate, tetrakis(triphenylphosphine) palladium, bis(triphenylphosphine)palladium(II) chloride, tris(dibenzylideneacetone)dipalladium(0) in the presence of ligands, for example 2,2'-bis(diphenylphosphino)-1,1'-binaphthyl, 9,9-dimethyl-4,5-bis(diphenylphosphino)xanthene, 1,1'-bis(diphenylphosphino)ferrocene, and bases, for example potassium carbonate, sodium carbonate, caesium carbonate or potassium phosphate, in suitable solvents, for example dioxane, toluene, dimethyl sulphoxide or N,N-dimethylformamide.

Compounds of the general formula (Ia) can alternatively be prepared by Process P3' by reaction of boronic acids of the general formula (VIIIa) with heterocyclic compounds of the general formula (XXII).

In general, the reactions take place under catalysis or mediation by copper(II) salts, for example copper(II) acetate, copper(II) triflate, or else by copper(I) salts, for example copper(I) chloride, copper(I) acetate, under an air or oxygen atmosphere, frequently under dehydrating conditions (for example with molecular sieve). Bases used are, for example, triethylamine, N-ethyldiisopropylamine, pyridine, 2,6-lutidine, N-methylmorpholine or 1,8-diazabicycloundec-7-ene in suitable solvents, for example dichloromethane, dichloroethane, methanol, N,N-dimethylformamide, tetrahydrofuran, dioxane, acetonitrile, ethyl acetate or toluene. The literature describes numerous examples, including U.S. Pat. No. 6,673,810 or Synthesis 2001, 6, 829-856 (for uracils). Comprehensive reviews can be found, for example, in Synthesis 2011, no. 6, 829-856 or in Tetrahedron 2012, vol. 68, 7735-7754. Instead of the boronic acid, it is also possible to use other boron compounds, for instance potassium trifluoroborate, boronic esters, etc., or else other organometallic compounds, for instance stannanes, silanes or bismuthanes.

By oxidation of the thioethers of the general formula (Ia) by methods known from the literature, it is possible to obtain the sulphoxides of the general formula (Ib). Alternatively, the oxidative transition metal-mediated carbon-nitrogen coupling to give aryl sulphoxides of the general formula (Ib) can be enabled proceeding from boronic sulphoxides of the general formula (VIIIb), which are obtainable by oxidation of the boronic acids (VIIIa), for example with sodium periodate, or analogous derivatives.

Process Pa1 (for I-A-I, $V^1=V^2=O$)

The 6-azauracils of the general formula (I-A-I) can be divided into (I-A-Ia) (n=0) and (I-A-Ib) (n=1) and can be prepared, for example, by Process Pa1, as shown in the following scheme:

PROCESS Pa1

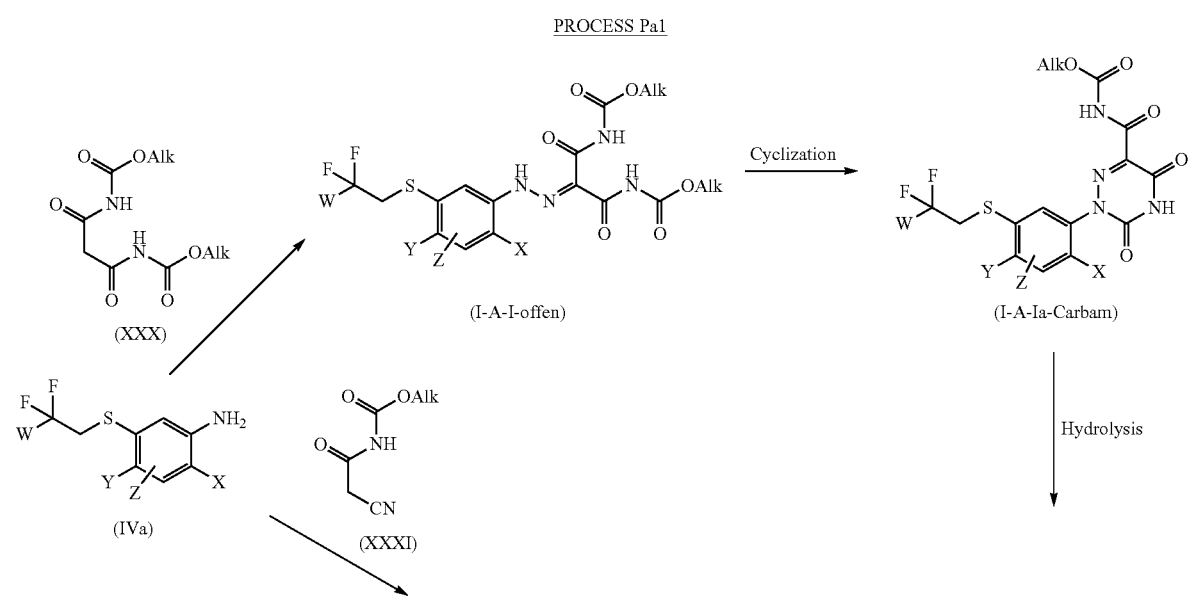

-continued

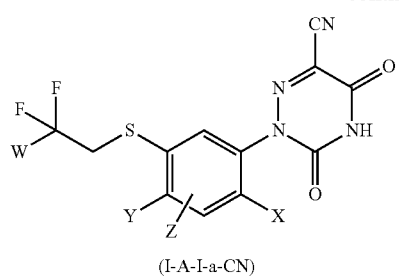
(I-A-I-a-CN)

Hydrolysis →

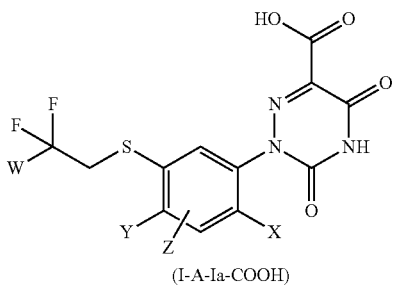
(I-A-Ia-COOH)

Decarbox. ↓

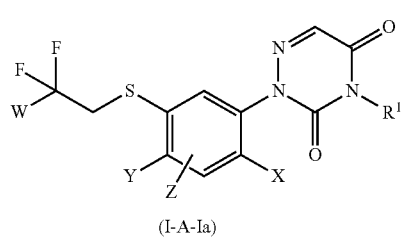
(I-A-Ia)

← Alkylation
R¹—LG

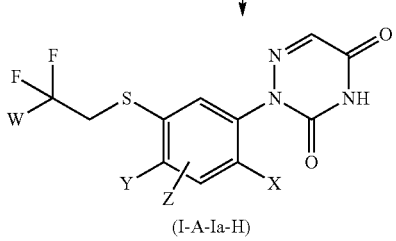
(I-A-Ia-H)

Oxidation ↓

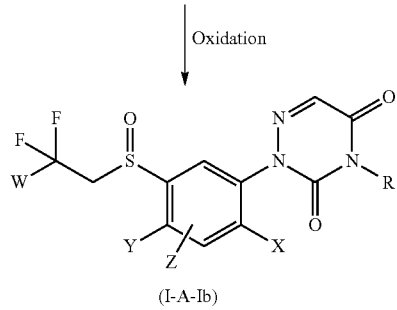
(I-A-Ib)

Oxidation ↓

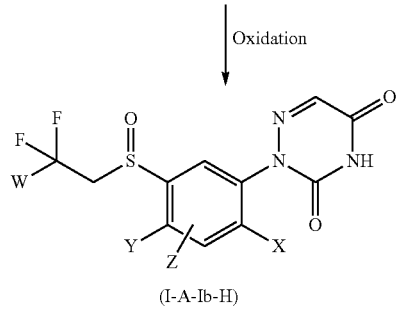
(I-A-Ib-H)

where X, Y, Z, W and $R^1$ are as defined above, Alk is a small alkyl group (especially methyl and ethyl) and LG is a typical leaving group in nucleophilic substitution reactions (especially bromide, iodide, triflate, mesylate) or in Mitsunobu reactions (especially hydroxyl).

Compounds of the general formula (I-A-Ia) and (I-A-Ia-H) where $R^1$=hydrogen can be prepared by Process Pa1 in a multistage operation from the anilines (IVa).

As the first synthesis step, anilines of the formula (IVa) can be converted by diazotization (for example by reaction with sodium nitrite in aqueous hydrochloric acid) followed by reaction with malonyldiurethanes of the formula (XXX) to give the hydrazones of the formula (I-A-I-open), for example in an aqueous sodium acetate solution. These intermediates (I-A-I-open) can then be converted, for example by treatment with sodium acetate in acetic acid while heating, to the 6-azauracils of the formula (I-A-Ia-carbam). By hydrolysis of these, for example in aqueous hydrochloric acid, it is possible to obtain the carboxylic acids (I-A-I-COOH).

Alternatively, 6-azauracil-5-carboxylic acids (I-A-I-COOH) can be obtained from the corresponding nitriles (I-A-I-CN) by hydrolysis. These can be prepared from the anilines (IVa), for example when they are reacted after the diazotization reaction with N-cyanoacetylurethane (XXXI), with Alk=ethyl, under similar reaction conditions to those mentioned above for the reaction with malonyldiurethanes.

Numerous methods for synthesis and cyclizations of hydrazones can be found in the literature, for example in Monatshefte Chem. 1968, 99(3), 1009-1013, Coll. Czech. Chem. Comm 1979, 44(8), 2438-2442 and Pharmazie 1980, 35(12), 744-745, all by J. Slouka. Examples of reaction conditions for hydrolyses of the carbamates in (I-A-Ia-carbam) or nitriles in (I-A-Ia-CN) can be found in WO 9800072 or U.S. Pat. No. 7,015,230.

For preparation of the 6-azauracils of the formula (I-A-Ia-H), carboxylic acids (I-A-I-COOH) can be decarboxylated, for example while heating in an inert high-boiling solvent, for example diphenyl ether according to Heterocycles 1978, 9(10), 1387-1390, or mercaptoacetic acid according to J. Med. Chem. 1979, 22(12), 1483-1487.

The inventive 3-substituted 6-azauracils of the formula (I-A-Ia) can be prepared from the unsubstituted (I-A-Ia-H) by reaction with suitable agents. For example, for the N-alkylation, it is possible to use alkylating agents of the formula $R^1$-LG in the presence of a suitable base, optionally in an inert solvent or diluent. Numerous methods can be found in the literature, for example in WO 9800072 for alkyl halides (LG=halogen), in WO 2003/042191 with diazomethyltrimethylsilane when $R^1$=methyl, or in WO 2003/011841 for alcohols (LG=OH) in a Mitsunobu reaction.

By oxidation of the thioethers of the general formula (I-A-Ia) or (I-A-Ia-H) by methods known from the literature, it is possible to obtain the sulphoxides of the general formula (I-A-Ib) or (I-A-Ib-H).

Process Pa2 (I-A-II)

The 1,3,5-triazine-2,4(1H,3H)-(di)(thi)ones of the general formula (I-A-II) can be divided into (I-A-IIa) (n=0) and (I-A-IIb) (n=1) and can be prepared, for example, by Process Pa2, as shown in the following scheme:

PROCESS Pa2

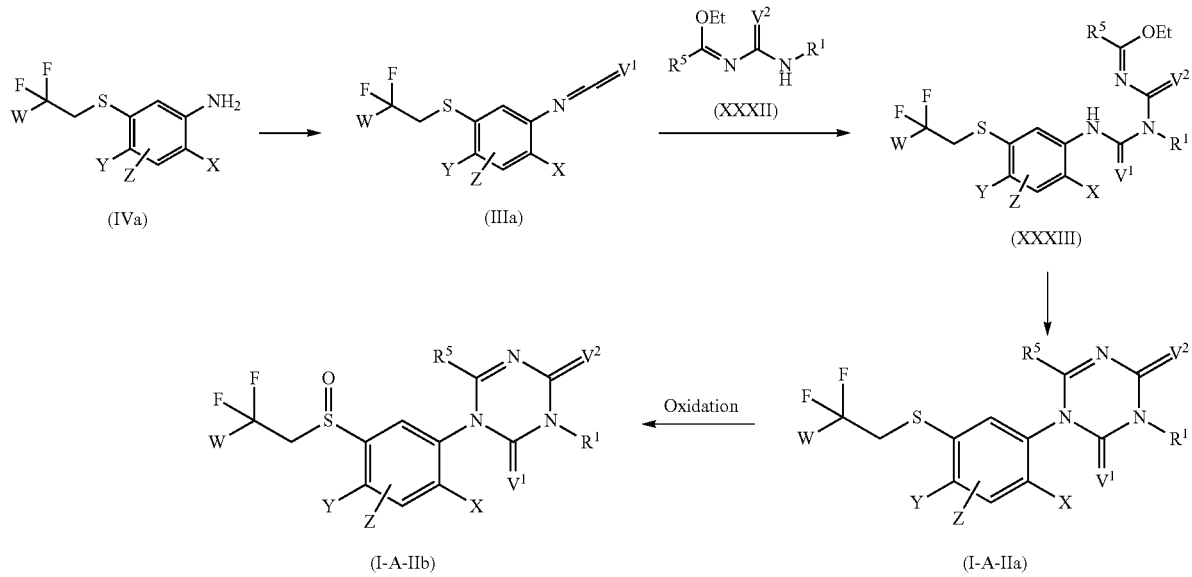

where X, Y, Z, W, $V^1$, $V^2$, $R^1$ and $R^5$ are as defined above.

Isocyanates ($V^1$=O) or isothiocyanates ($V^1$=S) of the general formula (IIIa) can be prepared by methods known from the literature from the anilines of the formula (IVa). They can be converted by reaction with imidoates of the formula (XXXII), alkylcarbamoyl imidoates when $V^2$=O or alkylcarbamothioyl imidoates when $V^2$=S, to compounds of the formula (XXXIII). These can then be cyclized to the inventive triazine(di)(thi)ones of the formula (I-A-IIa).

The ethyl N-(alkylcarbamo(thio)yl)imidoates of the formula (XXXII) required can be prepared from iso(thio)cyanates by methods known from the literature, for example by the addition of ethyl alkanimidoates at 50° C., as described in Comptes Rend. Seanc. Acad. Serie C 1977, 285(8), 285-288.

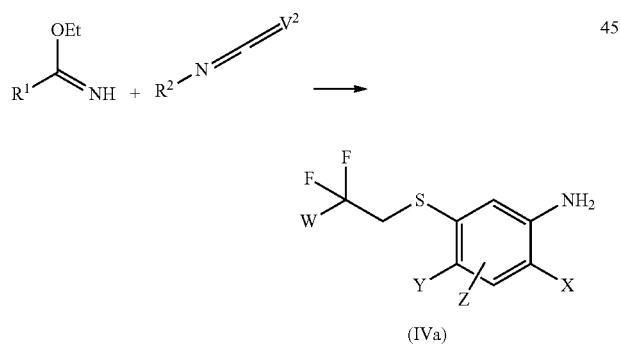

-continued

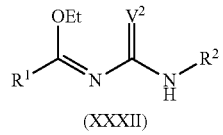

(XXXII)

The process described here—reaction of iso(thio)cyanates with imidoates to give triazine(di)(thi)ones of the formula (I-A-IIa)—optionally with the prior isolation of open-chain intermediates (XXXIII) and cyclization thereof—is described in Comptes Rend. Seanc. Acad. Serie C 1977, 285(8), 285-288, and 33-36.

By oxidation of the thioethers of the general formula (I-A-IIa) by methods known from the literature, it is possible to obtain the inventive sulphoxides of the general formula (I-A-IIb).

Process Pa3 (for I-A-III)

The inventive pyrimidine-2,4(1H,3H)-(di)(thi)ones (also called (thio)uracils) of the general formula (I) can be divided into (I-A-IIIc) (n=0) and (I-A-IIIb) (n=1), and can be obtained, for example, by Process Pa3 shown in the following scheme:

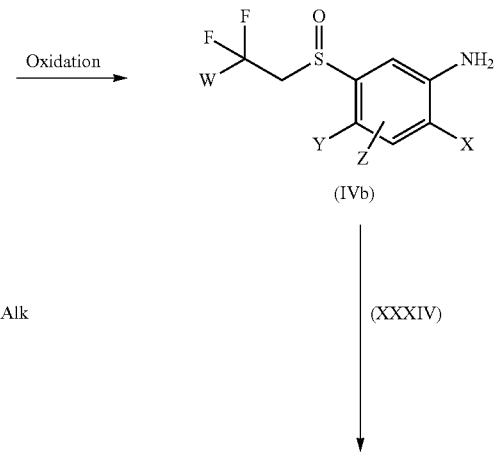

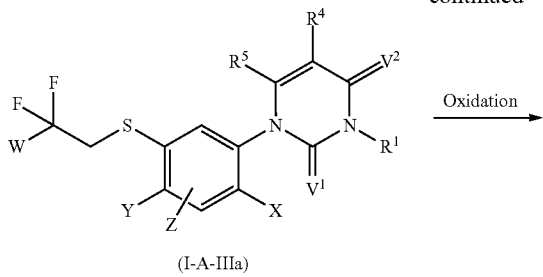

(I-A-IIIa) → Oxidation → (I-A-IIIb)

where $R^1$, $R^4$, $R^5$, $V^1$, $V^2$, W, X, Y and Z are as defined above and Alk is a small alkyl group (especially methyl or ethyl).

Anilines of the formula (IVa) can be reacted with carbamates of the general formula (XXXIV), without isolating the 3-anilino-2-cyanalk-2-enoyl (thio)carbamates formed as intermediates, to give the inventive compounds of the formula (I-A-IIIc).

By oxidation of the thioethers of the general formula (I-A-IIIc) by methods known from the literature, it is possible to obtain the inventive sulphoxides of the general formula (I-A-IIIb).

Alternatively, the anilines of the general formula (IVb), which can be prepared from their thioether precursors (IVa) by known oxidation methods, can be converted by the reaction with carbamates of the general formula (III) to the inventive compounds of the formula (I-A-IIIb).

The synthesis concept utilized in Process Pa3—the reaction of amines with carbamates to give substituted uracils—optionally with the prior isolation of open-chain intermediates and the cyclization thereof—has been described before in numerous publications, for example in GB 2021098 or DE 19536842. Liebigs Ann. Chem. 1982, 1, 182-185 describes a process which describes the simultaneous reaction of anilines with (cyanoacetyl)urea and carboxylic orthoesters for preparation of acryloylureas, and the subsequent thermal cyclization thereof gives uracils.

The compounds of the formula (III) required as starting materials, in which $V^1$ is oxygen and $V^2$ is oxygen or sulphur, are commercially available or can be prepared by literature methods, for example analogously to US 20040072746 or Tetrahedron Lett. 1970, 45, 3957-3960.

The reaction of the anilines of the formula (IVa) or (IVb) with carbamates of the general formula (III) can be conducted in substance or preferably in a solvent which is inert under the prevailing reaction conditions, optionally in the presence of an acid. Preference is given to aliphatic alcohols, for example methanol, ethanol, isopropanol, pentanol; ethers, for example diisopropyl ether, dioxane, tetrahydrofuran, 1,2-dimethoxyethane; nitriles, for example acetonitrile or propionitrile; or amides, for example N,N-dimethylformamide (DMF), N,N-dimethylacetamide or N-methylpyrrolidone; or mixtures of these with water; or aromatic hydrocarbons such as toluene, chlorobenzene, dichlorobenzenes, xylenes; or dimethyl sulphoxide. The reaction can be carried out under reduced pressure, at standard pressure or under elevated pressure and at temperatures of −20 to 250° C.; preferably, the reaction is effected at standard pressure and temperatures of 30 to 180° C.

Process Pa4 (for I-A-III with $V^1=V^2=O$)

The inventive pyrimidine-2,4(1H,3H)-diones (also called uracils) of the general formula (I) can be divided into (I-A-9a) (n=0) and (I-A-9b) (n=1), and can be obtained, for example, by Process Pa4 shown in the following scheme:

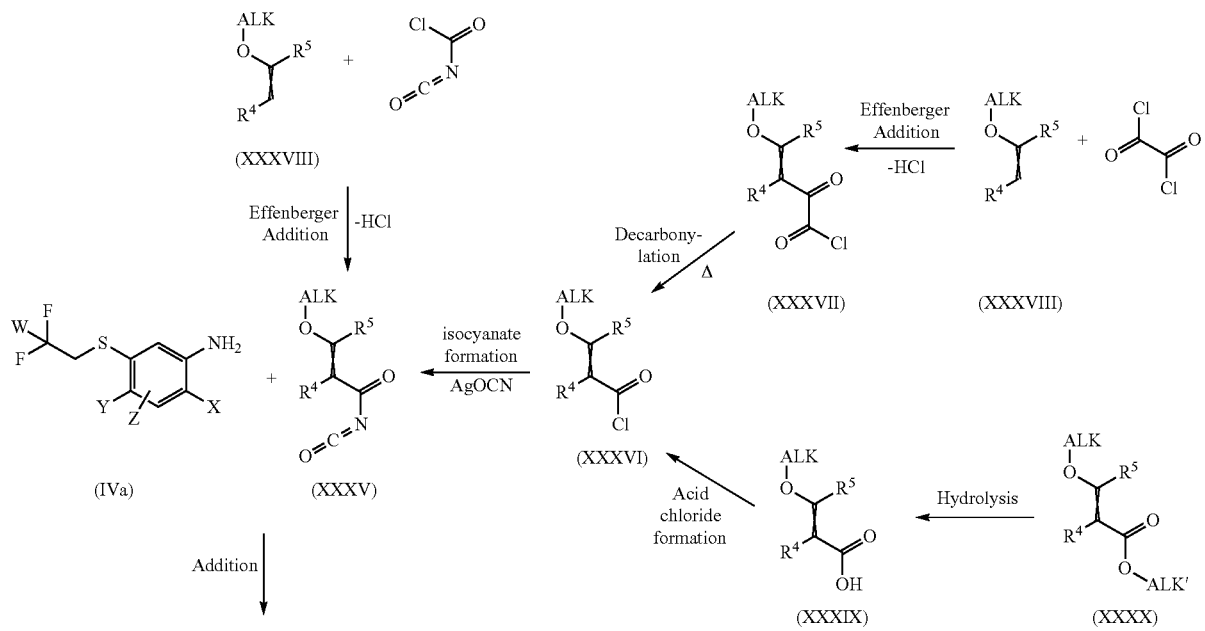

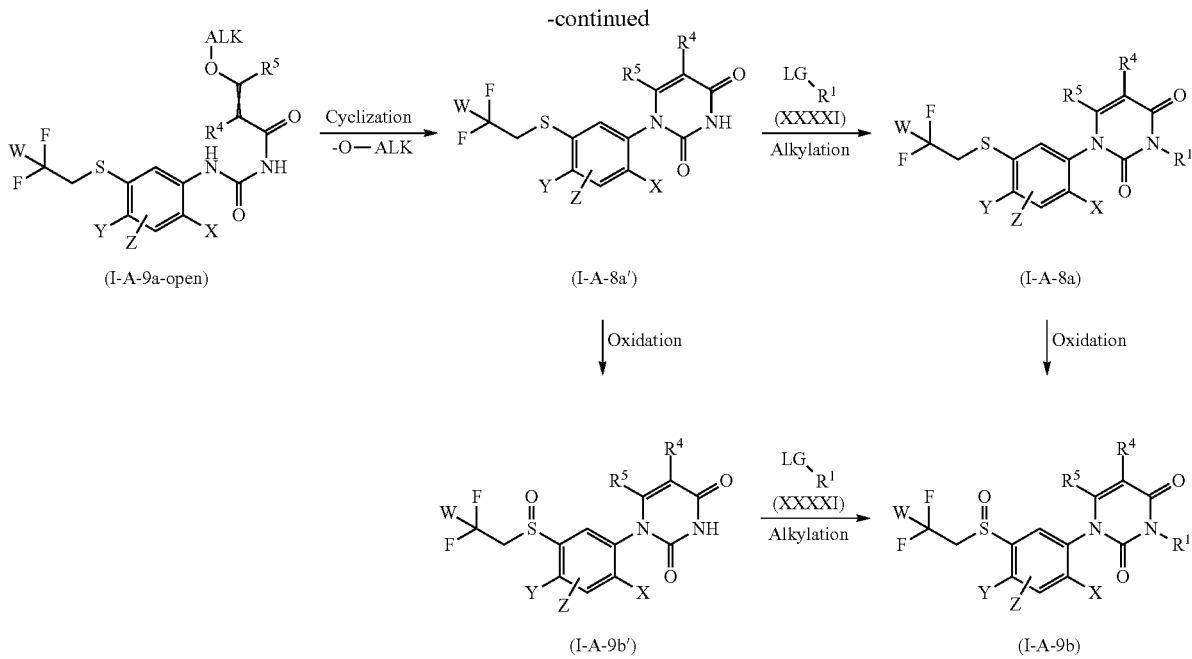

where $R^1$, $R^4$, $R^5$, W, X, Y and Z are as defined above and ALK is an alkyl group (especially methyl or ethyl).

Anilines of the formula (IVa) can be reacted with optionally substituted 3-alkoxyacryloyl isocyanates of the general formula (XXXV) to give the corresponding optionally substituted 3-alkoxy-N-(arylcarbamoyl)acrylamides of the general formula (I-A-9a-open). The optionally substituted 3-alkoxyacryloyl isocyanates of the general formula (XXXV) are obtainable by various synthesis routes known in the literature: for example, optionally substituted 3-alkoxyacryloyl chlorides of the general formula (XXXVI) can be reacted with silver cyanate, as described, for instance, in Synthesis 2001, 2, 239-242. The preparation of such optionally substituted 3-alkoxyacryloyl chlorides of the general formula (XXXVI) can be achieved, for example, by reaction of optionally substituted alkyl vinyl ethers of the general formula (XXXVIII), which are commercially available or known from the literature, with oxalyl chloride to give the corresponding α-keto acid chlorides of the general formula (XXXVII) and subsequent decarboxylation at elevated temperatures (see, for example, Synthesis 1993, 1079-1080 or J. Amer. Chem. Soc. 2011, 133, 41, 16418-16421). A further means of preparing optionally substituted 3-alkoxyacryloyl chlorides of the general formula (XXXVI) is the hydrolysis of 3-alkoxyacrylic esters of the general formula (XXXX), which are commercially available or known from the literature, to give the corresponding 3-alkoxyacrylic acids of the general formula (XXXIX) and subsequent acid chloride formation, for example with oxalyl chloride or thionyl chloride, as described, for instance, in J. Heterocyclic Chem. 1999, 36, 293-295.

Alternatively, optionally substituted 3-alkoxyacryloyl isocyanates of the general formula (XXXV) can be prepared by direct reaction of N-(chlorocarbonyl) isocyanate (see, for example, Angew. Chem. 1977, 89, 789-796) with optionally substituted alkyl vinyl ethers of the general formula (XXXVIII), which are commercially available or known from the literature, with addition of base, as described, for example, in Tetrahedron 2006, 62, 906-914 or in Nucleosides Nucleotides 1995, 14, 2039-2049. Preferably, the 3-alkoxyacryloyl isocyanates of the general formula (XXXV) shown are not isolated, but rather reacted directly with anilines of the formula (IVa) to give 3-alkoxy-N-(arylcarbamoyl)acrylamides of the general formula (I-A-9a-open).

Optionally substituted 3-alkoxy-N-(arylcarbamoyl)acrylamides of the general formula (I-A-9a-open) can either be isolated or cyclized without intermediate isolation to the corresponding 1-arylpyrimidine-2,4(1H,3H)-diones of the general formula (I-A-9a') under the action of acid or base (see, for example, WO2009/039127 or J. Org. Chem. 2005, 70, 20, 7925-7335), preferably under acidic reaction conditions with heating.

Subsequent N-alkylation with conventional alkylating agents of the general formula (XXXXI) where LG represents conventional leaving groups, for example chlorides, bromides, iodides, tosylates, triflates or mesylates, optionally in the presence of a suitable base and optionally using inert solvents, gives the corresponding pyrimidine-2,4(1H,3H)-diones of the general formula (I-A-9a) (see, for example, Tetrahedron 2007, 63, 2859-2864).

By oxidation of the thioethers of the general formula (I-A-9a) by methods known from the literature, it is possible to obtain the inventive sulphoxides of the general formula (I-A-9b).

Alternatively, the arylpyrimidine-2,4(1H,3H)-dione thioethers of the general formula (I-A-9a') can first be oxidized by methods known from the literature to give the inventive arylpyrimidine-2,4(1H,3H) sulphoxides of the general formula (I-A-9b') and then alkylated to the inventive arylpyrimidine-2,4(1H,3H)-dione of the general formula (I-A-9b).

Process Pa5 (for I-A-III with $V^1$=O or S and $V^2$=O)

The inventive compounds of the general formula (I) can be divided into (I-A-9a) (n=0) and (I-A-9b) (n=1), and can be obtained, for example, by Process Pa5 shown in the following scheme:

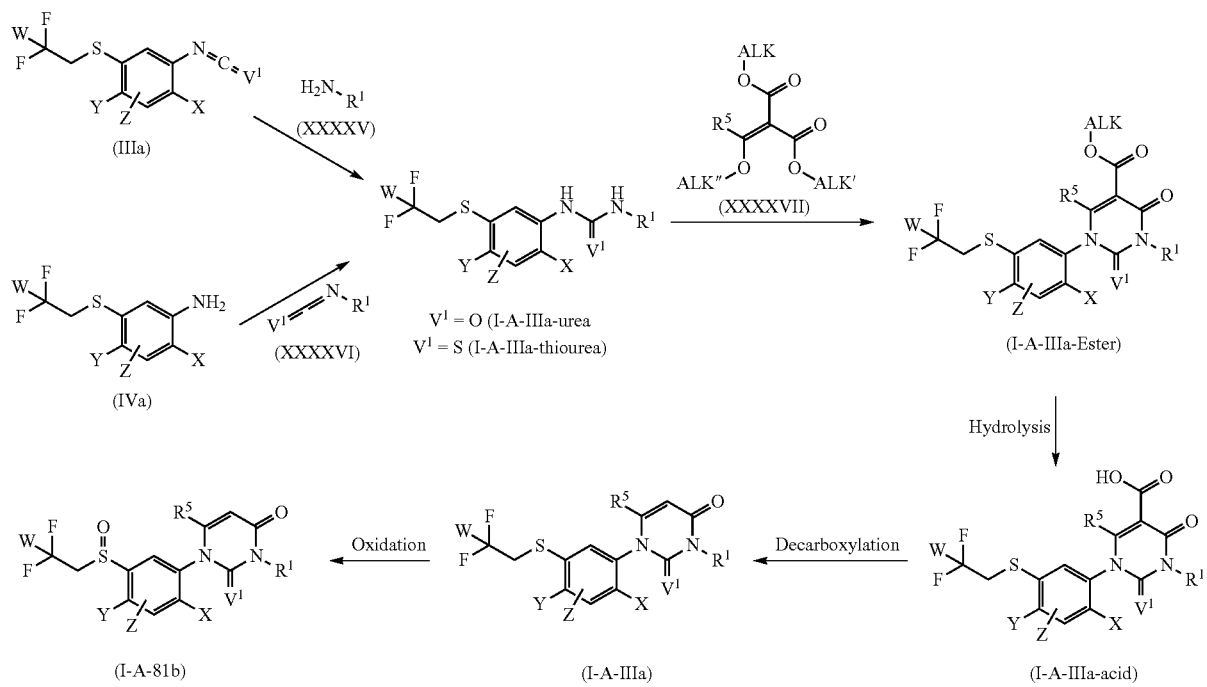

where $V^1$, $R^1$, $R^5$, W, X, Y and Z are as defined above and ALK, ALK' and ALK" are alkyl groups (especially methyl or ethyl).

Ureas of the general formula (I-A-IIIc-urea) or thioureas of the general formula (I-A-IIIa-thiourea) can firstly be synthesized from isocyanates or isothiocyanates of the general formula (IIIa) ($V^1$=O or S) by reaction with amines of the general formula (XXXXV), and secondly by reaction of anilines (IVa) with appropriate iso(thio)cyanates of the general formula (XXXXVI). Cyclization of the ureas or thioureas (I-A-IIIc-urea or -thiourea) by reaction of (alkoxymethylene)malonic esters of the general formula (XXXXVII), which are commercially available or known from the literature, leads to optionally substituted 1-aryl-2,4-dioxo- or 1-aryl-4-oxo-2-thioxo-1,2,3,4-tetrahydropyrimidine-5-carboxylic esters of the general formula (I-A-IIIc-ester); subsequent hydrolysis gives the corresponding carboxylic acid derivatives of the general formula (I-A-9a-acid), as described, for example, in WO2013/074633.

To prepare the uracils of the formula (I-A-IIIc) without substituent in the 5 position, carboxylic acids of the general formula (I-A-IIIc-acid) can be decarboxylated, for example with heating in an inert, high-boiling solvent, for example diphenyl ether or mercaptoacetic acid, in analogy to the methods described in Heterocycles 1978, 9(10), 1387-1390 or J. Med. Chem. 1979, 22(12), 1483-1487.

By oxidation of the thioethers of the general formula (I-A-IIIc) by methods known from the literature, it is possible to obtain the inventive sulphoxides of the general formula (I-A-IIIb).

Thionation:

A further general process for preparing the inventive compounds of the general formula (Ia) or (Ib) in which V or $V^1$ and $V^2$ may independently be sulphur involves the conversion of the carbonyl group(s) in corresponding precursors to the thiocarbonyl group with the aid of suitable thionating reagents, for example phosphorus pentasulphide or Lawesson's reagent in a suitable solvent, for example pyridine, xylene or cumene. This variant is described in numerous publications, for example in J. Amer. Chem. Soc. 1956, 1938-1941, Chem. Pharm. Bull. 1962, 10, 647-652, U.S. Pat. No. 3,007,927 (for 1,2,4-triazine(di)thiones), DE 2554866 or WO 2000026194 (for pyrimidinethiones).

Oxidation:

Compounds of the general formula (Ib) can be prepared through oxidation by processes known from the literature from compounds of the general formula (Ia), for example by means of an oxidizing agent in a suitable solvent and diluent. Suitable oxidizing agents are, for example, dilute nitric acid, hydrogen peroxide and peroxycarboxylic acids, for example meta-chloroperbenzoic acid. Suitable solvents are inert organic solvents, typically acetonitrile and halogenated solvents such as dichloromethane, chloroform or dichloroethane.

A variety of methods are suitable for production of enantiomerically enriched sulphoxides, as described by A. R. Maguire in ARKIVOC, 2011(i), 1-110: metal-catalysed asymmetric oxidations of thioethers, for example with titanium and vanadium as the most commonly used catalyst sources, in the form of Ti(O$^i$Pr$_4$) and VO(acac)$_2$, together with a chiral ligand and an oxidizing agent such as tert-butyl hydroperoxide (TBHP), 2-phenylpropan-2-yl hydroperoxide (CHP) or hydrogen peroxide; nonmetal-catalysed asymmetric oxidations through use of chiral oxidizing agents or chiral catalysts; electrochemical or biological asymmetric oxidations and kinetic resolution of sulphoxides and nucleophilic shift (by Andersen's method).

The enantiomers can also be obtained from the racemate by separating them preparatively, for example, on a chiral HPLC column.

Alternatively, compounds of the general formula (Ib) can be prepared by methods similar to those specified here in another sequence.

Elucidation of the Starting Materials and Intermediates
Anilines of the General Formula (IVa) and (IVb)

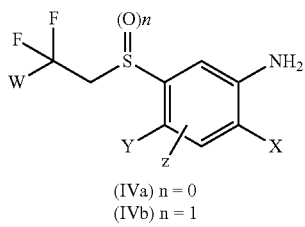

(IVa) n = 0
(IVb) n = 1

Some of the anilines of the formula (IVa) are known from the literature, for example from JP 2007/284356, or they can be synthesized by processes known from the literature, especially under the conditions specified in the preparation examples.

The compounds of the formula (IVb) are novel and can be prepared by oxidation, especially under the conditions specified in the preparation examples.

The anilines of the general formula (IVa) can preferably be prepared as in the following scheme:

presence of acids, acid anhydrides or acid chlorides, for example, the anilines (XIV) can be converted to the corresponding anilides (XIII). The chlorosulphonation of the protected anilines (XIII) with chlorosulphonic acid gives the corresponding sulphonyl chlorides (XII).

The reduction of the sulphonyl chlorides (XII) to the disulphides (XI) is possible by methods known from the literature, for example iron in hydrochloric acid or iodide. The reaction of the disulphides (XI) with haloalkyl electrophiles of the formula (XXVI) where AG is a leaving group, for example chlorine, bromine, tosylate, mesylate or triflate, gives the sulphides (X). The protecting group can be removed by suitable methods known from the literature, so as to obtain anilines of the formula (IVa).

Instead of the reduction to the disulphide (XI), the sulphonyl chloride (XII) can be reduced with a suitable reducing agent, for example iodine/phosphorus, to give the alkyl thioate (XVII), and then deprotected by a suitable method, for example the reaction with potassium hydroxide solution, to give thiols of the formula (XVI). The reaction of the thiols (XVI) with haloalkyl electrophiles of the formula (XXVI) gives the sulphides (IVa).

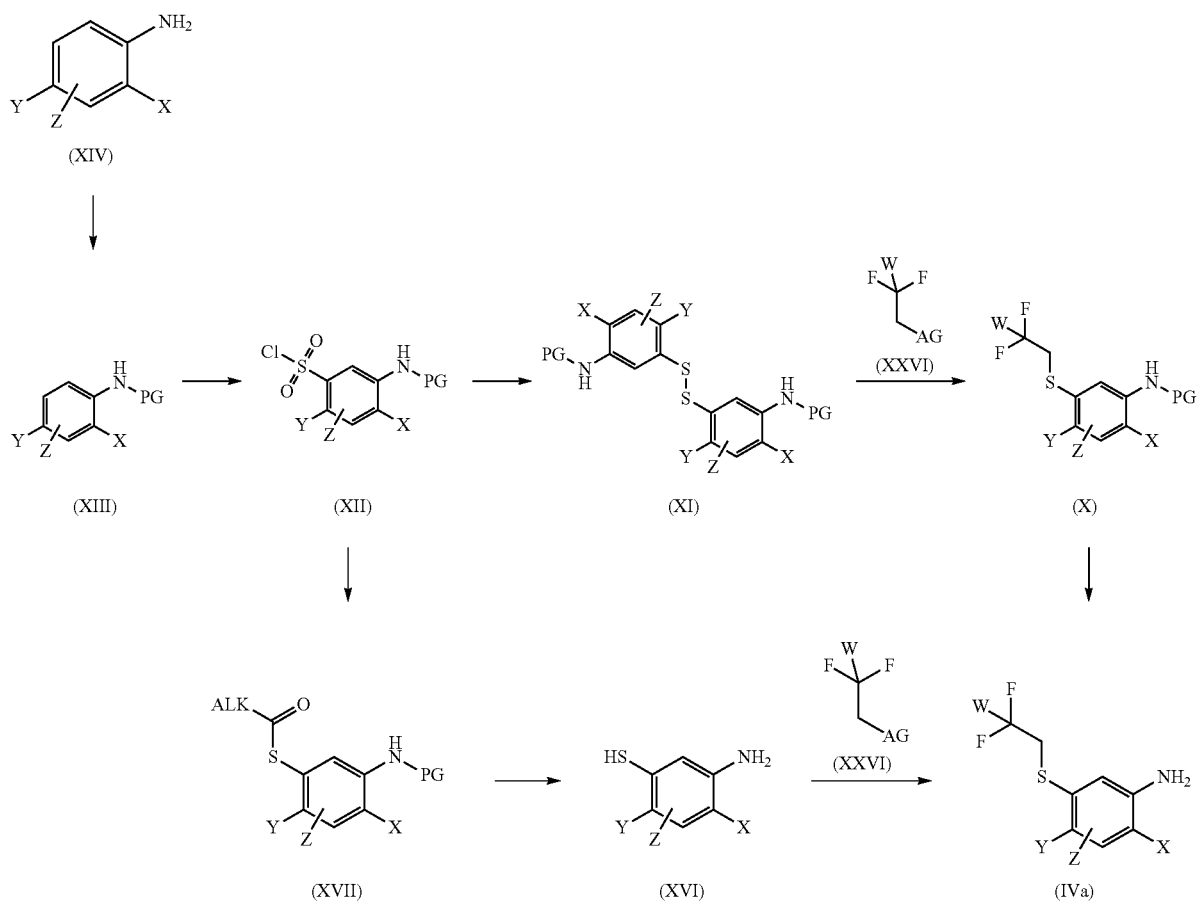

where X, Y, Z and W are as defined above, AG is a leaving group and PG is a protecting group.

Anilines of the formula (XIV) are either commercially available or can be prepared by known methods. They can be protected with a suitable protective group, for example an acetyl group, to give compounds of the formula (XIII). In the The compounds of the formulae (X), (XI), (XII), (XIII), (XVI) and (XVII) are novel and can be prepared particularly under the conditions specified in the preparation examples.

Likewise preferably, the thioethers of the formula (IVa) can alternatively be prepared according to the following scheme:

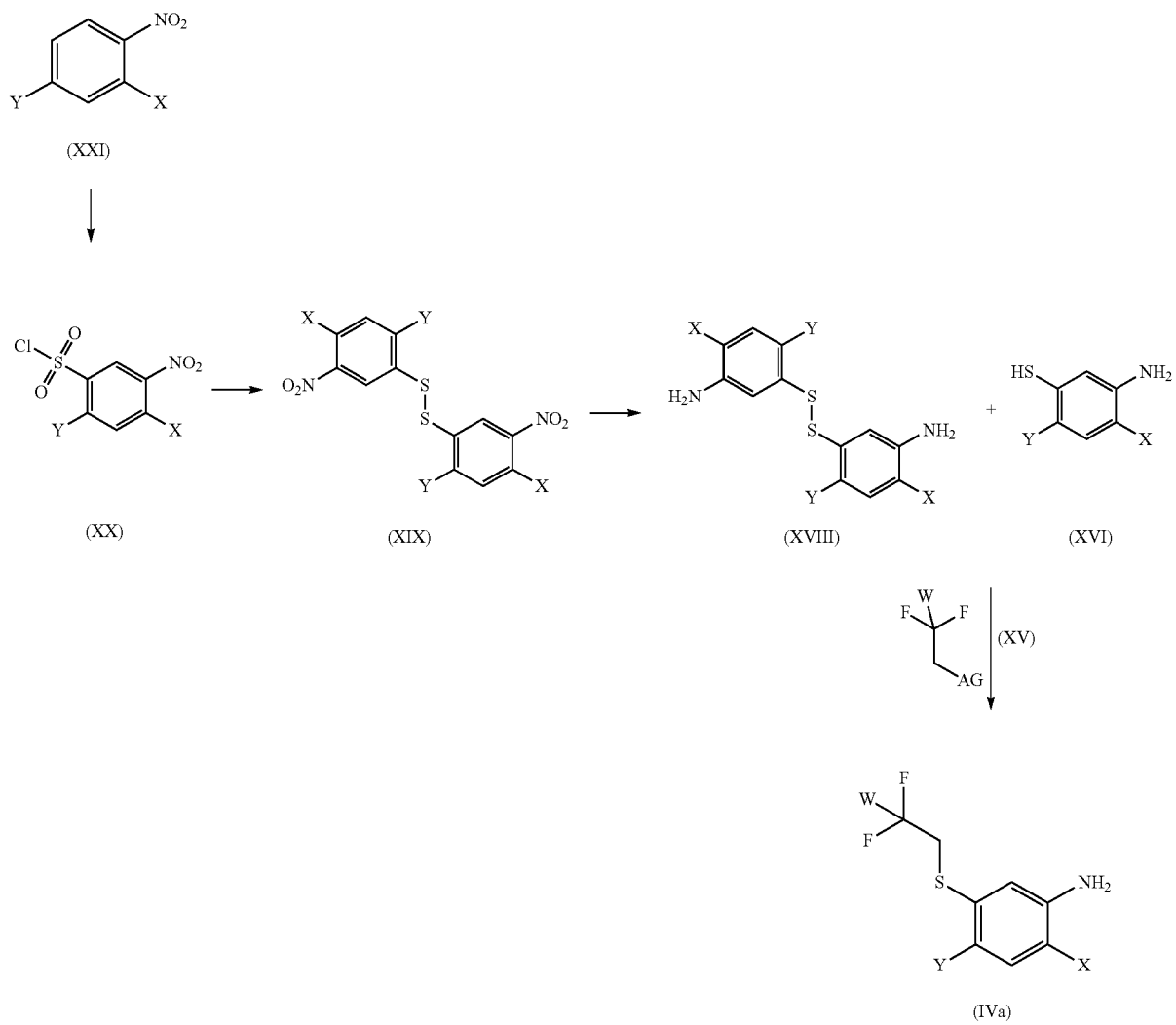

where X, Y, Z and W are as defined above, AG is a leaving group and PG is a protecting group.

The chlorosulphonation of the nitroaromatics of the formula (XXI) with chlorosulphonic acid gives the corresponding sulphonyl chlorides (XX). The reduction of the sulphonyl chlorides (XX) to the bis(nitroaryl) disulphides (XIX) is possible by methods known from the literature, for example iodide. The reduction of the disulphides (XXI) to the disulphanediyldianilines (XIX), some of which are formed as a mixture with the corresponding aminoarylthiols (XVI), is possible with commonly known reducing agents, for example hydrogen, optionally with the aid of heterogeneous catalysts, for example, Raney nickel, platinum on activated carbon or palladium on activated carbon. Reaction of the disulphides (XVIII) or thiophenols (XVI) with haloalkyl electrophiles of the formula (XV) where AG represents a leaving group such as, for example, chlorine, bromine, iodine, tosylate, mesylate or triflate affords the 3-[(2,2,2-trifluoroethyl)sulphanyl]anilines of the formula (IVa).

The compounds of the formulae (XVI), (XVIII), (XIX) and (XX) are novel and can be prepared in particular under the conditions mentioned in the Preparation Examples.

Isocyanates (V=O) and Isothiocyanates (V=S) of the General Formula (IIIa)

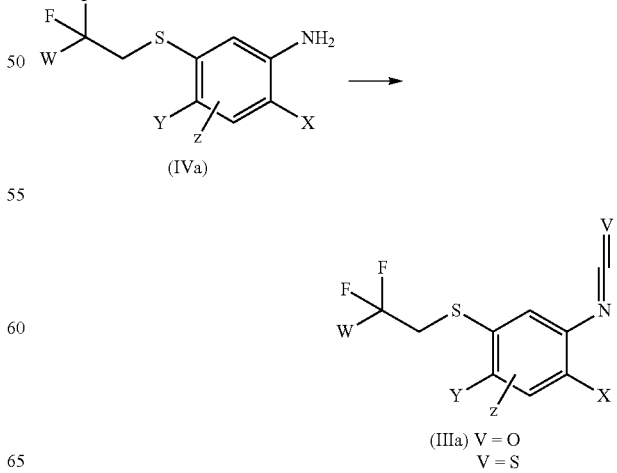

The synthesis intermediates (IIIa) (isocyanates when V=O, isothiocyanates when V=S) are known from the literature or can be prepared from the anilines of the general formula (IVa) by methods known from the literature. Isocyanates and isothiocyanates of the general formula (IIIa) are known from JP2011/042611 or can be prepared by methods known from the literature, especially under the conditions specified in the preparation examples.

Halides of the General Formula (VIIa)

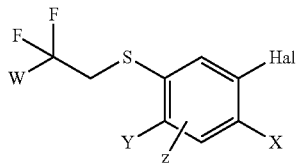

(VIIa)

in which X, Y, Z and W are as defined above and Hal is chlorine, bromine or iodine are known from the literature, from WO 2007/034755, JP 2007/081019, JP 2007/284385, JP 2008/260706, JP 2008/308448, JP 2009/023910 or WO 2012/176856, or can be synthesized by processes known from the literature, which may optionally be slightly modified, especially as described in the specific synthesis examples.

Suitable starting materials for the synthesis of the iodides of the general formula (VIIa) are bromides of the same formula, for example in halogen exchange reactions by methods known from the literature, optionally with metal catalysis (see H. Suzuki, Chem. Let. 1985, 3, 411-412; S. L. Buchwald, J. Amer. Chem. Soc. 2002, 124 (50), 14844-14845), especially under the conditions specified in the synthesis examples. Synthesis is likewise possible proceeding from anilines of the formula (IVa) under Sandmeyer reaction conditions, as described by E. B. Merkushev in Synthesis 1988, 12, 923-937.

Boronic Acids of the General Formula (VIIIa) and (VIIIb)

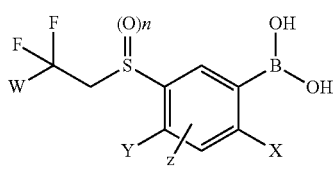

(VIIIa) n = 0
(VIIb) n = 1 in which X, Y, Z and W are as defined above are known from the literature, for example from WO2007/034755, JP2007/284385, JP2009/023910 and WO2012/176856, or can be synthesized by processes known from the literature, especially as in the specific synthesis examples.

Hydrazines of the General Formula (Va)

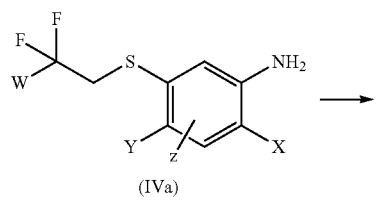

(IVa)

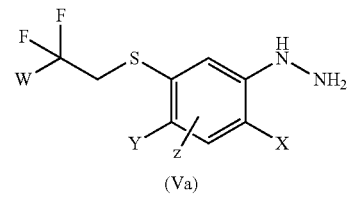

(Va)

Some hydrazines of the general formula (Va) are known from the literature, for example from EP 1803712 A1 and WO 2006043635, or they can be synthesized by processes known from the literature, as described, for example, in J. Med. Chem. 2003, 46, 4405-4418.

Heterocyclic Compounds of the Formula (XXII)

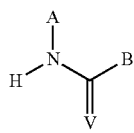

(XXII)

in which A and B are as defined above are commercially available or known from the literature, or they can be synthesized by processes known from the literature. As examples, the different heterocyclic compounds are divided into and specified in their subclasses.

1,2,4-Triazin(edi)(ethi)ones of the Formula (XXII-A-I)

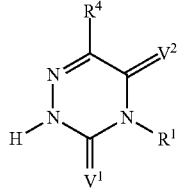

(XXII-A-I)

1,2,4-Triazin(edi)(ethi)ones of the formula (XXII-A-I) are commercially available or known from the literature, or they can be synthesized by processes known from the literature (analogously to the references cited below). Examples include the following compounds: 1,2,4-triazine-3,5(2H,4H)-dione (commercially available, Chem. Berichte 1947, 180, 494-502), 4-methyl-1,2,4-triazine-3,5(2H,4H)-dione (commercially available, Bull. Soc. Chim Fr. 1959, 1793-1798), 4-ethyl-1,2,4-triazine-3,5(2H,4H)-dione (Coll. Czech. Chem. Comm 1961, 26, 986-997), 3,4-dihydro-3-thioxo-1,2,4-triazin-5(2H)-one (commercially available, J. Amer. Chem. Soc. 1938-1941), 3,4-dihydro-4-methyl-3-thioxo-1,2,4-triazin-5(2H)-one (Coll. Czech. Chem. Comm 1961, 26, 986-997), 1,2,4-triazine-3,5(2H,4H)dithione (commercially available, U.S. Pat. No. 3,007,927), 4-methyl-1,2,4-triazine-3,5(2H,4H)dithione (commercially available, Coll. Czech. Chem. Comm 1961, 26, 986-997), 4,5-dihydro-5-thioxo-1,2,4-triazin-3(2H)-one (commercially available, Chem. Pharm. Bull 1962, 10, 647-652), 4,5-dihydro-4-methyl-5-thioxo-1,2,4-triazin-3(2H)-one (Coll. Czech. Chem. Comm 1961, 26, 986-997).

1,3,5-Triazin(edi)(ethi)ones of the General Formula (XXII-A-II)

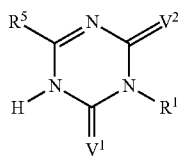

(XXII-A-II)

1,3,5-Triazin(edi)(ethi)ones of the formula (XXII-A-II) are commercially available or known from the literature, or they can be synthesized by processes known from the literature (analogously to the references cited below). Examples include the following compounds: 1,3,5-triazine-2,4(1H,3H)-dione (commercially available, Helv. Chim Acta 1959, 42, 485-489), 3-methyl-1,3,5-triazine-2,4(1H,3H)-dione (commercially available, Coll. Czech. Chem. Comm 1961, 26, 2519-2528), 1,3,4-triazine-2,4(1H,3H)-dithione (FR 697599), 4-hydroxy-6-methyl-1,3,5-triazin-2(1H)-one (commercially available, Coll. Czech. Chem. Comm 1963, 28, 1681-1690), 3,6-dimethyl-1,3,5-triazine-2,4(1H,3H)-dione (Comptes Rend. Seanc. Acad. Serie C 1978, 287(7), 285-288), 6-methyl-1,3,5-triazine-2,4(1H,3H)-dithione (J. Het. Chem. 1972, 9(5), 1013-1016).

Pyrimidine-2,4(1H,3H)-(di)(thi)ones (XXII-A-III)

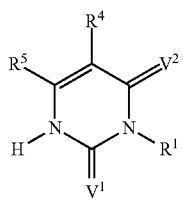

(XXII-A-III)

Uracils of the general formula (U-NH) are commercially available or can be prepared by methods known from the literature, for example analogously to J. Biol. Chem. 1925, 65, 469-477, Compt. Rend. 1959, 248, 3444-3446, DE 1248665, WO 9401102, J. Org. Chem. 1972, 11, 11738-11742, J. Org. Chem. 1977, 12, 2185-2187, J. Heterocycl. Chem. 1972, 9(5), 1175-1176, J. Heterocycl. Chem. 1972, 9(6), 1423, Can. J. Chem. 1978, 56(5), 725-729.

Compounds of the General Formula (XXIII) and (XXIII')

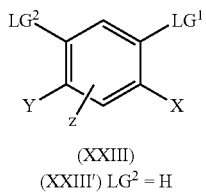

(XXIII)
(XXIII') LG² = H in which Z is as defined above, X is hydrogen or an electron-withdrawing group (especially nitro, chlorine, fluorine, cyano), Y represents electron-withdrawing substituents (especially nitro, chlorine, fluorine, cyano), LG¹ represents typical leaving groups in nucleophilic substitution reactions (especially fluoride, chloride) and LG² may be hydrogen or represent typical leaving groups in nucleophilic substitution reactions (especially fluoride, chloride) are commercially available or known from the literature, or can be synthesized by processes known from the literature.

Examples include the following commercially available compounds: 2,4,5-trifluorobenzonitrile (Y=CN, X=LG¹=LG²=F, Z=H), 2,4-difluorobenzonitrile (Y=CN, X=Z=H, LG¹=LG²=F), 3,4-difluorobenzonitrile (Y=CN, X=LG¹=F, LG²=Z=H).

Compounds of the General Formula (XXIV) and (XXIV')

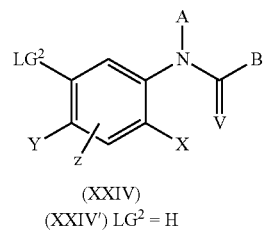

(XXIV)
(XXIV') LG² = H in which A, B, V and Z are as defined above, X is hydrogen or an electron-withdrawing group (especially nitro, chloride, fluoride, cyano), Y represents electron-withdrawing substituents (especially nitro, chloride, fluoride, cyano) and LG² may be hydrogen or represent typical leaving groups in nucleophilic substitution reactions (especially fluoride, chloride) are commercially available or known from the literature, or can be prepared by methods known from the literature, especially as described in the specific synthesis examples.

Examples include the following compounds: 4-[4-cyclopropyl-5-oxo-3-(trifluoromethyl)-4,5-dihydro-1H-1,2,4-triazol-1-yl]-2,5-difluorobenzonitrile (Y=CN, X=LG²=F, Z=H) (see synthesis examples), ethyl 4-methyl-5-oxo-1-phenyl-4,5-dihydro-1H-1,2,4-triazole-3-carboxylate (Y=CN, X=F, LG²=Z=H) (commercially available), methyl 1-(2-fluoro-4-methylphenyl)-4-isopropyl-5-oxo-4,5-dihydro-1H-1,2,4-triazole-3-carboxylate (synthesis according to DE 2725148).

Thiols of the General Formula (XXV)

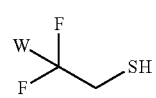

(XXV)

in which W is as defined above are commercially available or known from the literature, or are synthesized by processes known from the literature.

Examples include the following thiols: 2,2,2-trifluoroethanethiol (W=F) (commercially available), 2,2-difluoroethanethiol (W=H) (synthesis according to J. Amer. Chem. Soc. 1963, 85, 749-754), 2-chloro-2,2-difluoroethanethiol (W=Cl) (synthesis according to Phosp., Sulf., Sil. and rel. Elem. 1996, 119, 161-168).

Electrophiles of the General Formula (XXVI)

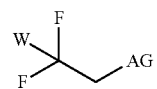

(XXVI)

in which W is as defined above and AG is halogen (especially chlorine, iodine) are commercially available or known from the literature, or are synthesized by processes known from the literature.

Examples include the following commercially available electrophiles: 2-chloro-1,1,1-trifluoroethane (W=F, AG=Cl), 2-chloro-1,1-difluoroethane (W=H, AG=Cl), 2-bromo-1,1,1-trifluoroethane (W=F, AG=Br), 2-bromo-1,1-difluoroethane (W=H, AG=Br), 2-iodo-1,1,1-trifluoroethane (W=F, AG=I), 2-iodo-1,1-difluoroethane (W=H, AG=I), 2,2,2-trifluoroethyl methanesulphonate (W=F, AG=—SO$_2$Me), 2,2,2-trifluoroethyl triflate (W=F, AG=—SO$_2$CF$_3$), 2,2,2-trifluoroethyl tosylate (W=F, AG=-SO$_2$(4-CH$_3$C$_6$H$_4$)).

The inventive active ingredients, or those to be used in accordance with the invention, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are active against normally sensitive and resistant species and against all or some stages of development. The abovementioned pests include:

pests from the phylum of the Arthropoda, more particularly from the class of the Arachnida, for example *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., *Epitrimerus pyri, Eutetranychus* spp., *Eriophyes* spp., *Glycyphagus domesticus, Halotydeus destructor, Hemitarsonemus* spp., *Hyalomma* spp., *Ixodes* spp., *Latrodectus* spp., *Loxosceles* spp., *Metatetranychus* spp., *Neutrombicula autumnalis, Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., *Tetranychus* spp., *Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus;* from the class of the Diplopoda, for example *Blaniulus guttulatus;* from the class of the Insecta, for example from the order of the Blattodea, for example *Blattella asahinai, Blattella germanica, Blatta orientalis, Leucophaea maderae, Panchlora* spp., *Parcoblatta* spp., *Periplaneta* spp., *Supella longipalpa;* from the order of the Coleoptera, for example *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptolestes ferrugineus, Cryptorhynchus lapathi, Cylindrocopturus* spp., *Dermestes* spp., *Diabrotica* spp., *Dichocrocis* spp., *Dicladispa armigera, Diloboderus* spp., *Epilachna* spp., *Epitrix* spp., *Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., *Lachnosterna consanguinea, Lasioderma serricorne, Latheticus oryzae, Lathridius* spp., *Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllophaga helleri, Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sitophilus oryzae, Sphenophorus* spp., *Stegobium paniceum, Sternechus* spp., *Symphyletes* spp., *Tanymecus* spp., *Tenebrio molitor, Tenebrioides mauretanicus, Tribolium* spp., *Trogoderma* spp., *Tychius* spp., *Xylotrechus* spp., *Zabrus* spp.;

from the order of the Diptera, for example *Aedes* spp., *Agromyza* spp., *Anastrepha* spp., *Anopheles* spp., *Asphondylia* spp., *Bactrocera* spp., *Bibio hortulanus, Calliphora erythrocephala, Calliphora vicina, Ceratitis capitata, Chironomus* spp., *Chrysomyia* spp., *Chrysops* spp., *Chrysozona pluvialis, Cochliomyia* spp., *Contarinia* spp., *Cordylobia anthropophaga, Cricotopus sylvestris, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit, Paratanytarsus* spp., *Paralauterborniella subcincta, Pegomyia* spp., *Phlebotomus* spp., *Phorbia* spp., *Phormia* spp., *Piophila casei, Prodiplosis* spp., *Psila rosae, Rhagoletis* spp., *Sarcophaga* spp., *Simulium* spp., *Stomoxys* spp., *Tabanus* spp., *Tetanops* spp., *Tipula* spp.;

from the order of the Heteroptera, for example *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptocorisa varicornis, Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Homoptera, e.g. *Acizzia acaciaebaileyanae, Acizzia dodonaeae, Acizzia uncatoides, Acrida turrita, Acyrthosipon* spp., *Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., *Anuraphis cardui, Aonidiella* spp., *Aphanostigma pini, Aphis* spp., *Arboridia apicalis, Arytainilla* spp., *Aspidiella* spp., *Aspidiotus* spp., *Atanus* spp., *Aulacorthum solani, Bemisia tabaci, Blastopsylla occidentalis, Boreioglycaspis melaleucae, Brachycaudus helichrysi, Brachycolus spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., *Psyllopsis* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoideus titanus*, *Schizaphis graminum*, *Selenaspidus articulatus*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*, *Zygina* spp.;

from the order of the Hymenoptera, for example *Acromyrmex* spp., *Athalia* spp., *Atta* spp., *Diprion* spp., *Hoplocampa* spp., *Lasius* spp., *Monomorium pharaonis*, *Sirex* spp., *Solenopsis invicta*, *Tapinoma* spp., *Urocerus* spp., *Vespa* spp., *Xeris* spp.;

from the order of the Isopoda, for example *Armadillidium vulgare*, *Oniscus asellus*, *Porcellio scaber*;

from the order of the Isoptera, for example *Coptotermes* spp., *Cornitermes cumulans*, *Cryptotermes* spp., *Incisitermes* spp., *Microtermes obesi*, *Odontotermes* spp., *Reticulitermes* spp.;

from the order of the Lepidoptera, e.g. *Achroia grisella*, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamstra brassicae*, *Melanitis leda*, *Mocis* spp., *Monopis obviella*, *Mythimna separata*, *Nemapogon cloacellus*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., *Hieroglyphus* spp., *Locusta* spp., *Melanoplus* spp., *Schistocerca gregaria*;

from the order of the Phthiraptera, for example *Damalinia* spp., *Haematopinus* spp., *Linognathus* spp., *Pediculus* spp., *Phylloera vastatrix*, *Phtirus pubis*, *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., *Pulex irritans*, *Tunga penetrans*, *Xenopsylla cheopsis*;

from the order of the Thysanoptera, for example *Anaphothrips obscurus*, *Baliothrips biformis*, *Drepanothrips reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamomi*, *Thrips* spp.;

from the order of the Zygentoma (=Thysanura), for example *Ctenolepisma* spp., *Lepisma saccharina*, *Lepismodes inquilinus*, *Thermobia domestica*;

from the class of the Symphyla, for example *Scutigerella* spp.;

pests from the phylum of the Mollusca, more particularly from the class of the Bivalvia, for example *Dreissena* spp., and also from the class of the Gastropoda, e.g. *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal parasites from the phyla of the Plathelminthes and Nematoda, for example *Ancylostoma duodenale*, *Ancylostoma ceylanicum*, *Ancylostoma braziliensis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Strongyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichiura*, *Wuchereria bancrofti*;

plant pests from the phylum of the Nematoda, i.e. plant-parasitic nematodes, more particularly *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp.

In addition, it is possible to control, from the sub-kingdom of the Protozoa, the order of the Coccidia, for example *Eimeria* spp.

The present invention further relates to formulations and use forms prepared therefrom as crop protection compositions and/or pesticides, for example drench, drip and spray liquors, comprising at least one of the inventive active ingredients. The use forms optionally comprise further crop protection agents and/or pesticides and/or action-improving adjuvants, such as penetrants, e.g. vegetable oils, for example rapeseed oil, sunflower oil, mineral oils, for example paraffin oils, alkyl esters of vegetable fatty acids, for example rapeseed oil methyl ester or soybean oil methyl ester, or alkanol alkoxylates, and/or spreaders, for example alkylsiloxanes, and/or salts, for example organic or inorganic ammonium or phosphonium salts, for example ammonium sulphate or diammonium hydrogenphosphate, and/or retention promoters, for example dioctyl sulphosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations optionally comprise, as well as one or more inventive active ingredients, further active agrochemical ingredients.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable facilities or else before or during application.

The auxiliaries used may be substances suitable for imparting special properties, such as certain physical, technical and/or biological properties, to the formulation of the active ingredient, or to the use forms prepared from these formulations (for example ready-to-use crop protection compositions such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkypyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons such as xylene, toluene or alkylnaphthalenes, chlorinated aromatic or aliphatic hydrocarbons such as chlorobenzene, chloroethylene or methylene chloride, aliphatic hydrocarbons such as cyclohexane, paraffins, petroleum fractions, mineral and vegetable oils, alcohols such as methanol, ethanol, isopropanol, butanol or glycol and their ethers and esters, ketones such as acetone, methyl ethyl ketone, methyl isobutyl ketone or cyclohexanone, strongly polar solvents such as dimethyl sulphoxide, and water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous when one of the active ingredients and/or one of the inert carriers is insoluble in water and when application is effected in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam formers or antifoams may also be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the active ingredients can be combined with any solid or liquid additive which is commonly used for formulation purposes.

Useful retention promoters include all those substances which reduce the dynamic surface tension, for example dioctyl sulphosuccinate, or increase the viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and thereby increase the mobility of active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations contain preferably between 0.00000001% and 98% by weight of active ingredient or more preferably between 0.01% and 95% by weight of active ingredient, more preferably between 0.5% and 90% by weight of active ingredient, based on the weight of the formulation.

The active ingredient content of the use forms (crop protection compositions) prepared from the formulations can vary within wide limits. The active ingredient concentration of the use forms may typically be between 0.00000001% and 95% by weight of active ingredient, preferably between 0.00001% and 1% by weight, based on the weight of the use form. The compounds are applied in a customary manner appropriate for the use forms.

The inventive active ingredients, or those for use in accordance with the invention, can be used as such or in formulations thereof, including in a mixture with one or more suitable fungicides, bactericides, acaricides, molluscicides, nematicides, insecticides, microbiologicals, beneficial species, fertilizers, bird repellents, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products. Combination of the inventive active ingredients, or those for use in accordance with the invention, with mixing partners gives synergistic effects, meaning that the efficacy of the particular mixture is greater than expected on the basis of the efficacies of the individual components. It is generally possible to use the combinations in premixes, tankmixes or readymixes, and also in seed applications.

The active ingredients identified here by their common name are known and are described, for example, in the pesticide handbook ("The Pesticide Manual" 14th Ed., British Crop Protection Council 2006) or can be found on the Internet (e.g. http://www.alanwood.net/pesticides).

Insecticides/acaricides/nematicides suitable as mixing components are:

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists, for example
cyclodiene organochlorines, e.g. chlordane and endosulfan; or
phenylpyrazoles (fiproles), e.g. ethiprole and fipronil.

(3) Sodium channel modulators/voltage-dependent sodium channel blockers, for example
pyrethroids, for example acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrine (pyrethrum), resmethrin, silafluofen, tefluthrin, tetramethrin, tetramethrin [(1R) isomers], tralomethrin and transfluthrin; or
DDT; or methoxychlor.

(4) Nicotinergic acetylcholine receptor (nAChR) agonists, for example
neonicotinoids, for example acetamiprid, clothianidin, dinotefuran, imidacloprid, nitenpyram, thiacloprid and thiamethoxam; or
nicotine; or
sulfoxaflor.

(5) Nicotinergic acetylcholine receptor (nAChR) allosteric activators, for example
spinosyns, for example spinetoram and spinosad.

(6) Chloride channel activators, for example
avermectins/milbemycins, for example abamectin, emamectin benzoate, lepimectin and milbemectin.

(7) Juvenile hormone imitators, for example
juvenile hormone analogs, for example hydroprene, kinoprene and methoprene; or
fenoxycarb; or pyriproxyfen.

(8) Active ingredients with unknown or nonspecific mechanisms of action, for example
alkyl halides, for example methyl bromide and other alkyl halides; or
chloropicrin; or sulphuryl fluoride; or borax; or tartar emetic.

(9) Selective antifeedants, for example pymetrozine; or flonicamid.

(10) Mite growth inhibitors, for example clofentezine, hexythiazox and diflovidazin; or etoxazole.

(11) Microbial disruptors of the insect gut membrane, e.g. *Bacillus thuringiensis* subspecies *israelensis*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, Vip3A, mCry3A, Cry3Ab, Cry3Bb, Cry34 Ab1/35Ab1; or
*Bacillus sphaericus*.

(12) Oxidative phosphorylation inhibitors, ATP disruptors, for example diafenthiuron; or
organotin compounds, e.g. azocyclotin, cyhexatin and fenbutatin oxide; or
propargite; or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, dipteran, for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon; or acequinocyl; or fluacrypyrim.

(21) Complex-I electron transport inhibitors, for example METI acaricides, for example fenazaquin, fenpyroximate, pyrimidifen, pyridaben, tebufenpyrad and tolfenpyrad; or rotenone (Derris).

(22) Voltage-dependent sodium channel blockers, for example indoxacarb; or metaflumizone.

(23) Inhibitors of acetyl-CoA carboxylase, for example tetronic and tetramic acid derivatives, for example spirodiclofen, spiromesifen and spirotetramat.

(24) Complex-IV electron transport inhibitors, for example
phosphines, for example aluminium phosphide, calcium phosphide, phosphine and zinc phosphide; or cyanide.

(25) Complex-II electron transport inhibitors, for example cyenopyrafen and cyflumetofen.

(28) Ryanodine receptor effectors, for example
diamides, e.g. chlorantraniliprole, cyantraniliprole and flubendiamide.

Further active ingredients, for example amidoflumet, azadirachtin, benclothiaz, benzoximate, bifenazate, bromopropylate, chinomethionat, cryolite, dicofol, diflovidazin, fluensulfone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM I-1582, for example VOTiVO™, BioNem), and the following compounds:
3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), flupyradifurone, 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP A 0 539 588), 4-{[(6-chloropyrid-3-yl)methyl](methyl)amino}furan-2(5H)-one (known from EP A 0 539 588), {1-(6-chloropyridin-3-yl)ethyl](methyl)oxido-$\lambda^4$-sulphanylidene}cyanamide (known from WO2007/149134) and its diastereomers {[(1R)-1-(6-chloropyridin-3-yl)ethyl](methyl)oxido-$\lambda^4$-sulphanylidene}cyanamide (A) and {[(1S)-1-(6-chloropyridin-3-yl)ethyl](methyl)oxido-$\lambda^4$-sulphanylidene}cyanamide (B) (likewise known from WO 2007/149134) and diastereomers [(R)-methyl(oxido) {(1R)-1-[6-(trifluoromethyl)pyridin-3-yl]ethyl}-$\lambda^4$-sulphanylidene]cyanamide (A1) and [(S)-methyl(oxido) {(1S)-1-[6-(trifluoromethyl)pyridin-3-yl]ethyl}-$\lambda^4$-sulphanylidene] cyanamide (A2), referred to as diastereomer group A (known from WO 2010/074747, WO 2010/074751), [(R)-methyl (oxido) {(1S)-1-[6-(trifluoromethyl)pyridin-3-yl]ethyl}-$\lambda^4$-sulphanylidene]cyanamide (B1) and [(S)-methyl(oxido) {(1R)-1-[6-(trifluoromethyl)pyridin-3-yl]ethyl}-$\lambda^4$-sulphanylidene]cyanamide (B2), referred to as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-{2-fluoro-4-methyl-5-[(2,2,2-trifluoroethyl)sulphinyl]phenyl}-3-(trifluoromethyl)-1H-1,2,4-triazol-5-amine (known from WO 2006/043635), afidopyropen (known from WO 2008/066153), 2-cyano-3-(difluoromethoxy)-N,N-dimethylbenzenesulphonamide (known from WO 2006/056433), 2-cyano-3-(difluoromethoxy)-N-methylbenzenesulphonamide (known from WO 2006/100288), 2-cyano-3-(difluoromethoxy)-N-ethylbenzenesulphonamide (known from WO 2005/035486), 4-(difluoromethoxy)-N-ethyl-N-methyl-1,2-benzothiazol-3-amine-1,1-dioxide (known from WO 2007/057407), N-[1-(2,3-dimethylphenyl)-2-(3,5-dimethylphenyl)ethyl]-4,5-dihydro-1,3-thiazol-2-amine (known from WO 2008/104503), {1'-[(2E)-3-(4-chlorophenyl)prop-2-en-1-yl]-5-fluorospiro[indol-3,4'-piperidine]-1(2H)-yl}(2-chloropyridin-4-yl)methanone (known from WO 2003/106457), 3-(2,5-dimethylphenyl)-4-hydroxy-8-methoxy-1,8-diazaspiro[4.5]dec-3-en-2-one (known from WO 2009/049851), 3-(2,5-dimethylphenyl)-8-methoxy-2-oxo-1,8-diazaspiro[4.5]dec-3-en-4-yl ethyl carbonate (known from WO 2009/049851), 4-(but-2-yn-1-yloxy)-6-(3,5-dimethylpiperidin-1-yl)-5-fluoropyrimidine (known from WO 2004/099160), (2,2,3,3,4,4,5,5-octafluoropentyl)(3,3,3-trifluoropropyl)malononitrile (known from WO 2005/063094), (2,2,3,3,4,4,5,5-octafluoropentyl)(3,3,4,4,4-pentafluorobutyl)malononitrile (known from WO 2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO 2007/040280), flometoquin, PF1364 (CAS Reg. No. 1204776-60-2) (known from JP 2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO 2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO 2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO 2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2 (5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO 2010/005692), pyflubumide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO 2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO 2007/101369), 2-{6-[2-(5-fluoropyridin-3-yl)-1,3-thiazol-5-yl]pyridin-2-yl}pyrimidine (known from WO 2010/006713), 2-{6-[2-(pyridin-3-yl)-1,3-thiazol-5-yl]pyridin-2-yl}pyrimidine (known from WO 2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO 2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO 2010/069502), (1E)-N-[(6-chloropyridin-3-yl)methyl]-N'-cyano-N-(2,2-difluoroethyl)ethanimidamide (known from WO 2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN 102057925), methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO 2011/049233), heptafluthrin, pyriminostrobin, flufenoxystrobin and 3-chloro-N$^2$-(2-cyanopropan-2-yl)-N$^1$-[4-(1,1,1,2,3,3,3-heptafluorpropan-2-yl)-2-methylphenyl]phthalamide (known from WO2012/034472).

Fungicides suitable as mixing partners are:

(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl] 1H-imidazole-1-carbothioate.

(2) Respiration inhibitors (respiratory chain inhibitors), for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2, 2-tetrafluoroethoxy)phenyl]-3-(trifluoromethyl)-1H-pyrazole-4-carboxamide, 3-(difluoromethyl)-1-methyl-N-[2-(1, 1,2,2-tetrafluoroethoxy)phenyl]-1H-pyrazole-4-carboxamide, 3-(difluoromethyl)-N-[4-fluoro-2-(1,1,2,3,3, 3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl] quinazoline-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl) ethanamide, (2E)-2-(methoxyimino)-N-methyl-2-{2-[(E)-({1-[3-(trifluoromethyl)phenyl]ethoxy}imino)methyl] phenyl}ethanamide, (2E)-2-{2-[({[(1E)-1-(3-{[(E)-1-fluoro-2-phenylethenyl]oxy}phenyl)ethylidene]amino}oxy) methyl]phenyl}-2-(methoxyimino)-N-methylethan amide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl] ethylidene}amino)oxy]methyl}phenyl)-2,4-dihydro-3H-1, 2,4-triazol-3-one, methyl (2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl] phenyl}-2-methoxy-N-methylacetamide and (2R)-2-{2-[(2, 5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4] triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper formulations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations, for example calcium polysulphide, thiram, tolylfluanid, zineb and ziram.

(6) Resistance inductors, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) ATP production inhibitors, for example fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, fthalide, pyroquilon, tricyclazole and 2,2,2-trifluoroethyl {3-methyl-1-[(4-methylbenzoyl)amino]butan-2-yl}carbamate.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulphamide, dazomet, debacarb, dichlorophen, diclomezine, difenzoquat, difenzoquat methylsulphate, diphenylamine, ecomat, fenpyrazamine, flumetover, fluoromide, flusulphamide, flutianil, fosetyl-aluminium, fosetyl-calcium, fosetyl-sodium, hexachlorobenzene, irumamycin, methasulphocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrin, tebufloquin, tecloftalam, tolnifanid, triazoxide, trichlamide, zarilamide, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2, 6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6- tetrachloro-4-(methylsulphonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl) quinoline, 3,4,5-trichloropyridine-2,6-dicarbonitrile, 3-[5-(4-chlorophenyl)-2,3-dimethyl-1,2-oxazolidin-3-yl] pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-fluoro-2-[(4-fluorobenzyl)oxy]pyrimidine-4-amine, 5-fluoro-2-[(4-methylbenzyl)oxy]pyrimidine-4-amine, 5-methyl-6-octyl[1,2,4]triazolo[1,5-a]pyrimidine-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N—{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulphate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulphonyl)valinamide, 4-oxo-4-[(2-phenylethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate.

All the mixing partners mentioned in classes (1) to (16), as the case may be, may form salts with suitable bases or acids if they are capable of doing do on the basis of their functional groups.

All plants and parts of plants can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example seedlings, tubers, rhizomes, cuttings and seeds.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They may be cultivars, varieties, biotypes or genotypes.

The treatment of the plants and parts of plants with the inventive active ingredients, active ingredient combinations or compositions, or with those to be used in accordance with the invention, is effected directly or by action on their surroundings, habitat or storage space by the customary treatment methods, for example by dipping, spraying, atomizing, irrigating, evaporating, dusting, fogging, broadcasting, foaming, painting, spreading-on, injecting, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

One preferred direct treatment of the plants is foliar application, meaning that the active ingredients, active ingredient combinations or compositions are applied to the foliage, where the frequency of treatment and the application rate may be adjusted for the infestation pressure of the particular pathogen, pest or weed.

In the case of systemically active ingredients, the active ingredients, active ingredient combinations or compositions access the plants via the root system. The treatment of the plants then proceeds through the action of the active ingredients, active ingredient combinations or compositions on the habitat of the plant. This can be done, for example, by drenching, or by mixing into the soil or the nutrient solution, meaning that the locus of the plant (e.g. soil or hydroponic systems) is impregnated with a liquid form of the active ingredients, active ingredient combinations or compositions, or by soil application, i.e. the inventive active ingredients, active ingredient combinations or compositions are introduced in solid form (e.g. in the form of granules) into the locus of the plants. In the case of paddy rice crops, this can also be done by metering the invention in a solid application form (for example as granules) into a flooded paddy field.

The control of animal pests by the treatment of the seed of plants has long been known and is the subject of constant improvement. Nevertheless, the treatment of seed gives rise to a series of problems which cannot always be solved in a satisfactory manner. For instance, it is desirable to develop methods for protecting the seed and the germinating plant which make unnecessary, or at least reduce considerably, the additional deployment of crop protection compositions in the course of storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates particularly to a method for protection of seed and germinating plants from attack by pests, by treating the seed with an inventive active ingredient or active ingredient for use in accordance with the invention. The method of the invention for protection of seed and germinating plants against attack by pests comprises a method in which the seed is treated simultaneously in one operation with an active ingredient of the formula I and a mixing partner. It also comprises a method where the seed is treated at different times with an active ingredient of the formula I and a mixing partner.

The invention likewise relates to the use of the inventive active ingredients for the treatment of seed for protecting the seed and the resulting plant from animal pests.

Furthermore, the invention relates to seed which has been treated with an inventive active ingredient for protection from animal pests. The invention also relates to seed which has been treated simultaneously with an active ingredient of the formula I and a mixing partner. The invention further relates to seed which has been treated at different times with an active ingredient of the formula (I) and a mixing partner. In the case of seed which has been treated at different times with an active ingredient of the formula (I) and a mixing partner, the individual active ingredients in the inventive composition may be present on the seed in different layers. In this case, the layers comprising an active ingredient of the formula I and a mixing partner may optionally be separated by an intermediate layer. The invention also relates to seed where an active ingredient of the formula I and a mixing partner have been applied as a component of a coating or as a further layer or further layers in addition to a coating.

The invention further relates to seed which, after the treatment with the active ingredient of the formula (I) or an active ingredient combination comprising the active ingredient of the formula (I), has been subjected to a film-coating process to prevent dust abrasion on the seed.

One of the advantages of the present invention is that the particular systemic properties of the inventive compositions mean that treatment of the seed with these compositions protects not only the seed itself but also the resulting plants after emergence from animal pests. In this way, the immediate treatment of the crop at the time of sowing or shortly thereafter can be dispensed with.

A further advantage is considered to be that the treatment of the seed with active ingredient of the formula (I) or active ingredient combination comprising the active ingredient of the formula (I) can promote germination and emergence of the treated seed.

It is likewise to be considered to be advantageous that the active ingredients of the formula (I) and the active ingredient combinations mentioned can also be used for transgenic seed in particular.

It should also be mentioned that the active ingredients of the formula (I) can be used in combination with signalling technology compositions, which results, for example, in better colonization by symbionts, for example rhizobia, mycorrhizae and/or endophytic bacteria, and/or leads to optimized nitrogen fixation.

The inventive compositions are suitable for protection of seed of any plant variety which is used in agriculture, in greenhouses, in forests or in horticulture. More particularly, this is the seed of cereals (for example wheat, barley, rye, millet and oats), corn, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya, cotton, canola, oilseed rape and rice.

As already mentioned above, the treatment of transgenic seed with active ingredients of the formula (I) or an active ingredient combination is also of particular significance. This involves the seed of plants which generally contain at least one heterologous gene which controls the expression of a polypeptide having insecticidal and/or nematicidal properties in particular. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The gene involved is more preferably a heterologous gene which originates from *Bacillus thuringiensis*.

Within the context of the present invention, the active ingredient of the formula (I) is applied to the seed alone (or as an active ingredient combination) or in a suitable formulation. Preferably, the seed is treated in a state in which it is stable enough to avoid damage during treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

In general, in the treatment of the seed, it has to be ensured that the amount of the inventive composition and/or further additives applied to the seed is selected such that the germination of the seed is not impaired and the plant which arises therefrom is not damaged. This should be ensured particularly in the case of active ingredients which can exhibit phytotoxic effects at particular application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active ingredients/active ingredient combinations usable in accordance with the invention can be converted to the customary seed-dressing formulations, such as solutions, emulsions, suspensions, powders, foams, slurries or other coating compositions for seed, and also ULV formulations.

These formulations are prepared in a known manner, by mixing the active ingredients/active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples which may be mentioned are the colorants known by the names Rhodamin B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Nonionic or anionic dispersants or mixtures of nonionic or anionic dispersants are usable with preference. Suitable nonionic dispersants include especially ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Useful adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel" [Chemistry of Crop Protection Agents and Pesticides], vol. 2, Springer Verlag, 1970, p. 401-412).

The seed dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, and beets, or else a wide variety of different vegetable seed. The seed dressing formulations usable in accordance with the invention, or the dilute preparations thereof, can also be used to dress seed of transgenic plants. In this context, additional synergistic effects may also occur in cooperation with the substances formed by expression.

For treatment of seed with the seed dressing formulations usable in accordance with the invention, or the preparations prepared therefrom by adding water, all mixing units usable customarily for the seed dressing are useful. Specifically, the seed dressing procedure is to place the seed into a mixer, to add the particular desired amount of seed dressing formulations, either as such or after prior dilution with water, and to mix them until the formulation is distributed homogeneously on the seed. If appropriate, this is followed by a drying operation.

The application rate of the seed dressing formulations usable in accordance with the invention can be varied within a relatively wide range. It is guided by the particular content of the active ingredient(s) in the formulations and on the seed. The application rates in the case of active ingredients/active ingredient combinations are generally between 0.001 and 50 g per kilogram of seed, preferably between 0.01 and 15 g per kilogram of seed.

The prior art does not disclose whether the active ingredients of the formula (I) are effective against biotic stress factors and/or abiotic stress of plants or with respect to plant growth.

It has now been found that the inventive active ingredients of the formula (I) are suitable for enhancing the defences of the plant (pathogen control in plants).

It is known that plants react to natural stress conditions, for example cold, heat, drought, injury, attack by pathogens (viruses, bacteria, fungi), insects etc., but also to herbicides, with specific or unspecific defence mechanisms (Pflanzenbiochemie [Plant Biochemistry], pp. 393-462, Spektrum Akademischer Verlag, Heidelberg, Berlin, Oxford, Hans W. Heldt, 1996; Biochemistry and Molecular Biology of Plants, pp. 1102-1203, American Society of Plant Physiologists, Rockville, Md., eds. Buchanan, Gruissem, Jones, 2000). In this case, for example, cell wall components formed through injury or specific signal substances originating from the pathogen serve as inductors of plant signal transduction chains which ultimately lead to the formation of defensive molecules directed against the stress factor. These may be, for example, (a) low molecular weight substances, for example phytoalexins, (b) non-enzymatic proteins such as pathogenesis-related proteins (PR proteins), (c) enzymatic proteins such as chitinases, glucanases, or (d) specific inhibitors of essential proteins such as protease inhibitors, xylanase inhibitors, which attack the pathogen directly or hinder its proliferation (Dangl and Jones, Nature 411, 826-833, 2001; Kessler and Baldwin, Annual Review of Plant Biology, 53, 299-328, 2003).

An additional defence mechanism is called the hypersensitivity reaction (HR), which is mediated via oxidative stress and causes death of plant tissue in the region of a centre of infection, which prevents the spread of plant pathogens which are dependent on living cells (Pennazio, New Microbiol. 18, 229-240, 1995).

Later in the progression of an infection, the plant's messenger substances transmit signals to unaffected tissues, which leads to triggering of defence reactions in these tissues too and prevents secondary infections (Systemic acquired resistance, SAR) (Ryals et al., The Plant Cell 8, 1809-1819, 1996).

A number of signalling substances which are endogenous to plants and are involved in stress tolerance or pathogenic defence are already known. Examples here include salicylic acid, benzoic acid, jasmonic acid or ethylene (Biochemistry and Molecular Biology of Plants, p. 850-929, American Society of Plant Physiologists, Rockville, Md., eds. Buchanan, Gruissem, Jones, 2000). Some of these substances or the stable synthetic derivatives and derived structures thereof are also effective on external application to plants or in seed dressing, and activate defence reactions which cause elevated stress tolerance or pathogen tolerance of the plant (Sembdner, Parthier, Ann. Rev. Plant Physiol. Plant Mol. Biol. 44, 569-589, 1993). Salicylate-mediated defence is directed particularly against phytopathogenic fungi, bacteria and viruses (Ryals et al., The Plant Cell 8, 1809-1819, 1996).

A known synthetic product which has a function similar to that of salicylic acid and can mediate a protective effect against phytopathogenic fungi, bacteria and viruses is benzothiadiazole (CGA 245704; common name: acibenzolar-S-methyl; trade name: Bion®) (Achuo et al., Plant Pathology 53 (1), 65-72, 2004; Tamblyn et al., Pesticide Science 55 (6), 676-677, 1999; EP-A 0 313 512).

Other compounds which belong to the group of the oxylipins, for example jasmonic acid, and the protective mechanisms that they trigger are particularly effective against harmful insects (Walling, J. Plant Growth Regul. 19, 195-216, 2000).

It is additionally known that treatment of plants with insecticides from the group of the neonicotinoids (chloronicotinyls) leads to increased resistance of the plant to abiotic stress. This is especially true of imidacloprid (Brown et al., Beltwide Cotton Conference Proceedings 2231-2237, 2004). This protection results from modification of physiological and biochemical properties of the plant cells, for example improvement of membrane stability, increasing the carbohydrate concentration, increasing the polyol concentration and antioxidant activity (Gonias et al., Beltwide Cotton Conference Proceedings 2225-2229, 2004).

Also known is the effect of chloronicotinyls on biotic stress factors (Crop Protection 19 (5), 349-354, 2000; Journal of Entomological Science 37(1), 101-112, 2002; Annals of Biology (Hisar, India) 19 (2), 179-181, 2003). For example, insecticides from the group of the neonicotinoids (chloronicotinyls) lead to increased expression of genes from the group of the pathogenesis-related proteins (PR proteins). PR proteins support plants primarily in defence against biotic stressors, for example phytopathogenic fungi, bacteria and viruses (DE 10 2005 045 174 A; DE 10 2005 022 994 A and WO 2006/122662 A; Thielert Pflanzenschutz-Nachrichten Bayer, 59 (1), 73-86, 2006; Francis et al., European Journal of Plant Pathology, publ. online 23.1.2009).

It is additionally known that treatment of genetically modified plants with insecticides from the group of the neonicotinoids (chloronicotinyls) leads to improved stress tolerance of the plant (EP 1 731 037 A), for example with respect to the herbicide glyphosate too (WO 2006/015697 A).

It is thus known that plants possess several endogenous reaction mechanisms which can bring about effective defence against a wide variety of harmful organisms (biotic stress) and/or abiotic stress.

The growing of healthy young plants with uniform growth forms an essential prerequisite for cultivation of large areas and economical crop management of agricultural, horticultural and forestry crop plants.

Numerous methods for growing young plants are established in agriculture, forestry and horticulture. In this context, the growing substrates used, as well as steamed soil, are also special substrates based, inter alia, on peat mosses, coconut fibres, rockwool such as Grodan®, pumice, expanded clay such as Lecaton® or Lecadan®, clay granules such as Seramis®, foams such as Baystrat®, vermiculite, perlite, synthetic soil such as Hygromull®, or combinations of these substrates, into which seed, either undressed or dressed with fungicides and/or insecticides, is sown.

In specific crops such as tobacco, young plants are increasingly grown by the float method or floating method (Leal, R. S., The use of Confidor S in the float, a new tobacco seedlings production system in the South of Brazil, Pflanzenschutz-Nachrichten Bayer (German edition) (2001), 54(3), pages 337 to 352; Rudolph, R. D.; Rogers, W. D.; The efficacy of imidacloprid treatment for reduction in the severity of insect vectored virus diseases of tobacco, Pflanzenschutz-Nachrichten Bayer (German edition) (2001), 54(3), pages 311 to 336). In this method, the seed is sown in special containers, for example Styropor tablets with holes, in special growing soil based on peat culture substrate, and then cultivated in containers with suitable nutrient solution until the desired transplantation size is reached (FIG. 1). The containers are allowed to float on the nutrient solution, from which the name of the growing method derives (Leal, 2001, see above). In floating methods, sucking pests have been controlled for a number of years using insecticides from the class of the neonicotinoids (chloronicotinyls). Typically, the plants in the float method are sprayed with neonicotinoid (chloronicotinyls) insecticides shortly before transplantation, or they are watered with neonicotinoid (chloronicotinyls) insecticides immediately before or during transplantation, which is referred to as drenching (Leal, 2001, see above; Rudolph and Rogers, 2001, see above). Both application methods are technically relatively complex.

To protect the emerging seed or planting stock from fungal pathogens and pests, fungicides and insecticides are used here until transplantation. The choice of crop protection compositions, the location and the timing of the application and the application rate of the compositions depends here particularly on the kind of fungal diseases and pests that occur, on the specific mode of action and duration of action of the compositions and on their compatibility with plants, and can therefore be adapted directly to the specific requirements of different crops and regions.

Irrespective of any insect control, the active ingredients of the formula (I) lead to good protection of the plants from damage by fungal, bacterial or viral pathogens.

Without wishing to be tied to a theory, it is currently assumed that the defence against the pathogens results from the induction of PR proteins as a consequence of treatment with at least one active ingredient of the formula (I).

More particularly, the inventive use shows the advantages described in the treatment of seed, in soil treatment, in specific growing and cultivation methods (for example floating box, rockwool, hydroponic), but also in stem and foliar treatment. Combinations of an active ingredient of the formula (I) with insecticides, fungicides and bactericides, inter alia, show synergistic action in the control of plant diseases. The combined use of the active ingredients of the formula (I) with cultivars genetically modified with a view to increased abiotic stress tolerance additionally leads to a synergistic improvement in growth.

Finally, it has also been found in accordance with the invention that the active ingredients of the formula (I) are suitable not only for enhancing pathogen defence in plants but also for improving plant growth and/or for enhancing the resistance of plants to plant diseases caused by fungi, bacteria, viruses, MLO (*Mycoplasma*-like organisms) and/or RLO (*Rickettsia*-like organisms), especially to soil-borne fungal diseases, and/or for increasing the resistance of plants to abiotic stress factors.

Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or lack of shade.

The present invention therefore firstly provides for the use of at least one active ingredient of the formula (I) for enhancing the defences of plants and/or for improving plant growth and/or for enhancing the resistance of plants to plant diseases caused by fungi, bacteria, viruses, MLO (*Mycoplasma*-like organisms) and/or RLO (*Rickettsia*-like organisms), especially to soil-borne fungal diseases, and/or for enhancing the resistance of plants to abiotic stress factors.

In the context of the present invention, the term "plant growth" is understood to mean various benefits for plants that are not directly associated with the known pesticidal activity, preferably insecticidal activity, of the active ingredient of the formula (I). Such beneficial properties are, for example, the following improved plant characteristics: accelerated germination and emergence of seed and planting stock, improved root growth with regard to surface area and depth, increased stolon or tiller formation, stronger and more productive stolons and tillers, improvement in shoot growth, increased lodging resistance, increased shoot base diameter, increased leaf area, greener leaf colour, higher yields of nutrients and constituents, for example carbohydrates, fats, oils, proteins, vitamins, minerals, essential oils, dyes, fibres, better fibre quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soils and water, enhanced tolerance to UV radiation, enhanced tolerance to ozone stress, improved compatibility with respect to herbicides and other plant treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

As is known, the further various benefits for plants mentioned above can be combined in component form, and generally applicable terms can be used to describe them. Such terms are, for example, the following names: phytotonic effect, resistance to stress factors, less plant stress, plant health, healthy plants, plant fitness, plant wellness, plant concept, vigour effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is entirely familiar.

It has also been found that active ingredients of the formula (I) lead to increased expression of genes from the group of the pathogenesis-related proteins (PR proteins). PR proteins support the plants primarily in the defence against biotic stressors, for example phytopathogenic fungi, bacteria and viruses. The result of this is that plants, after application of active ingredients of the formula (I), are better protected against infections by phytopathogenic fungi, bacteria and viruses. In the event that it is necessary to use insecticides, fungicides and bactericides in a mixture with active ingredients of the formula (I), including in sequential application, the action of the latter is promoted.

It has additionally been found in accordance with the invention that the application of the active ingredients of the formula (I) in combination with a fertilizer as defined below to plants or in the environment thereof has a synergistic growth-enhancing effect.

Fertilizers which can be used in accordance with the invention together with the active ingredients or compositions which have been elucidated in detail above are generally organic and inorganic nitrogen compounds, for example ureas, urea/formaldehyde condensates, amino acids, ammonium salts and ammonium nitrates, potassium salts (preferably chlorides, sulphates, nitrates), salts of phosphoric acid and/or salts of phosphorous acid (preferably potassium salts and ammonium salts). Particular mention should be made in this connection of the NPK fertilizers, i.e. fertilizers which comprise nitrogen, phosphorus and potassium, calcium ammonium nitrate, i.e. fertilizers which also contain calcium, ammonium sulphate nitrate (general formula $(NH_4)_2SO_4NH_4NO_3$), ammonium phosphate and ammonium sulphate. These fertilizers are common knowledge to those skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may also contain salts of micronutrients (preferably calcium, sulphur, boron, manganese, magnesium, iron, boron, copper, zinc, molybdenum and cobalt) and phytohormones (for example vitamin B1 and indole-3-acetic acid (IAA)) or mixtures thereof. Fertilizers used in accordance with the invention may also contain other salts such as monoammonium phosphate (MAP), diammonium phosphate (DAP), potassium sulphate, potassium chloride or magnesium sulphate. Suitable amounts for the secondary nutrients or trace elements are amounts of 0.5 to 5% by weight, based on the overall fertilizer. Further possible ingredients are crop protection agents, insecticides or fungicides, growth regulators or mixtures thereof. Further details of these are given below.

The fertilizers can be used, for example, in the form of powders, granules, prills or compactates. However, the fertilizers can also be used in liquid form, dissolved in an aqueous medium. In this case, dilute aqueous ammonia can also be used as a nitrogen fertilizer. Further possible ingredients for fertilizers are described, for example, in Ullmann's Encyclopedia of Industrial Chemistry, 5th edition, 1987, volume A 10, pages 363 to 401, DE-A 41 28 828, DE-A 19 05 834 and DE-A 196 31 764.

The general composition of the fertilizers, which, in the context of the present invention, may take the form of straight and/or compound fertilizers, for example composed of nitrogen, potassium or phosphorus, may vary within a wide range. In general, a content of 1 to 30% by weight of nitrogen (preferably 5 to 20% by weight), 1 to 20% by weight of potassium (preferably 3 to 15% by weight) and a content of 1 to 20% by weight of phosphorus (preferably 3 to 10% by weight) is advantageous. The content of microelements is usually in the ppm range, preferably in the range from 1 to 1000 ppm.

In the context of the present invention, the fertilizer and the active ingredient of the formula (I) can be administered simultaneously, i.e. synchronously. However, it is also possible first to apply the fertilizer and then the active ingredient of the formula (I), or first to apply the active ingredient of the formula (I) and then the fertilizer. In the case of nonsynchronous application of the active ingredient of the formula (I) and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, the inventive active ingredients of the general formula (I) and the fertilizer are applied within a time frame of less than 1 hour, preferably less than 30 minutes, more preferably less than 15 minutes.

In addition, it is possible to produce dimensionally stable mixtures, for example in the form of rods, granules, tablets etc., proceeding from at least one active ingredient for use in accordance with the invention and at least one fertilizer. In order to produce a corresponding dimensionally stable mixture, the appropriate components can be mixed with one another and optionally extruded, or the at least one active ingredient of the formula (I) for use in accordance with the invention can be applied to the fertilizer. If appropriate, it is also possible to use formulation auxiliaries in the dimensionally stable mixtures, for example extenders or adhesives, to achieve dimensional stability of the resulting mixture. By virtue of the corresponding dimensional stability, corresponding mixtures are particularly suitable for use in the home & garden sector, i.e. for a domestic user or amateur gardener, who is able to use the dimensionally stable mixture or the components thereof in a predetermined, clearly defined amount and without any particular aids.

Irrespective of this, the mixtures comprising at least one of the active ingredients for use in accordance with the invention and the at least one fertilizer may also be in liquid form, such that—for example in the case of a professional user in the field of agriculture—the resulting mixture may be deployed as a tankmix.

Through the use of at least one of the active ingredients for use in accordance with the invention and at least one fertilizer, it is possible to achieve increased root growth which, in turn, enables higher nutrient uptake and hence promotes plant growth.

The active ingredients for use in accordance with the invention, optionally in combination with fertilizers, can preferably be employed in the following plants, although the enumeration which follows is not limiting.

Preferred plants are those from the group of the useful plants, ornamental plants, turfgrass types, commonly used trees which are employed as ornamentals in public and domestic areas, and forestry trees. Forestry trees include trees for the production of timber, cellulose, paper and products made from parts of the trees.

The term "useful plants" as used here refers to crop plants which are used as plants for obtaining foods, animal feeds, fuels or for industrial purposes.

The useful plants include, for example, the following types of plants: turf, vines, cereals, for example wheat, barley, rye, oats, triticale, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soya beans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, Cinnamomum, camphor, or also plants such as tobacco, nuts, coffee, aubergine, sugar cane, tea, pepper, grapevines, hops, bananas, latex plants and ornamentals, for example flowers, shrubs, deciduous trees and coniferous trees such as conifers. This enumeration does not constitute a limitation.

Particularly suitable target crops are considered to be the following plants: cotton, aubergine, turf, pome fruit, stone fruit, soft fruit, maize, wheat, barley, cucumber, tobacco, vines, rice, cereals, pear, beans, soya beans, oilseed rape, tomato, bell pepper, melons, cabbage, potatoes and apples.

Examples of trees include: *Abies* sp., *Eucalyptus* sp., *Picea* sp., *Pinus* sp., *Aesculus* sp., *Platanus* sp., *Tilia* sp.,

*Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees include: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus*.

Particularly preferred trees include: from the tree species *Pinus: P. radiate, P. ponderosa, P. contorta, P. sylvestre, P. strobes*; from the tree species *Eucalyptus: E. grandis, E. globulus, E. camadentis*.

Very particularly preferred trees include: horse chestnut, Platanaceae, linden tree, maple tree.

The present invention can also be applied to any turfgrass types, including cool-season turfgrasses and warm-season turfgrasses. Examples of cool-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchard grass (*Dactylis glomerata* L.), weeping alkaligrass (*Puccinellia distans* (L.) Parl.) and crested dog's-tail (*Cynosurus cristatus* L.).

Examples of warm-season turfgrasses are Bermuda grass (*Cynodon* spp. L. C. Rich), zoysia grass (*Zoysia* spp. Willd.), St. Augustine grass (*Stenotaphrum secundatum* Walt Kuntze), centipede grass (*Eremochloa ophiuroides* Munro Hack.), carpet grass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), Blue grama (*Bouteloua gracilis* (H.B.K.) Lag. ex Griffiths), seashore paspalum (*Paspalum vaginatum* Swartz) and sideoats grama (*Bouteloua curtipendula* (Michx. Torr.)). Cool-season turfgrasses are generally preferred for the inventive use. Especially preferred are bluegrass, bentgrass and redtop, fescues and ryegrasses. Bentgrass is especially preferred.

The active ingredients of the formula (I) and compositions thereof are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For control of animal pests, the active ingredients or compositions are used alone or in combination with other active ingredients and/or auxiliaries. They are preferably used in domestic insecticide products. The inventive active ingredients are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

In addition, the active ingredients of the formula (I) can be used to control a multitude of different pests, including, for example, harmful sucking insects, biting insects and other pests which are plant parasites, stored material pests, pests which destroy industrial material, and hygiene pests including parasites in the animal health sector, and for the control thereof, for example the elimination and eradication thereof. The present invention thus also includes a method for controlling pests.

In the animal health field, i.e. in the field of veterinary medicine, the inventive active ingredients are active against animal parasites, especially ectoparasites or endoparasites. The term "endoparasites" includes especially helminths and protozoa, such as coccidia. Ectoparasites are typically and preferably arthropods, especially insects and acarids.

In the field of veterinary medicine, the inventive compounds having favourable homeotherm toxicity are suitable for the control of parasites encountered in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets or especially dogs, cats; cage birds; reptiles; amphibians or aquarium fish.

In a preferred embodiment, the inventive compounds are administered to mammals.

In another preferred embodiment, the inventive compounds are administered to birds, namely cage birds or especially poultry.

The use of the inventive active ingredients for the control of animal parasites is intended to reduce or prevent illness, cases of deaths and performance losses (in the case of meat, milk, wool, hides, eggs, honey and the like), so that more economical and simpler animal keeping is enabled and better animal well-being is achievable.

In relation to the field of animal health, the term "control" or "controlling" means that the active ingredients can effectively reduce the incidence of the respective parasite in an animal infected with such parasites to a harmless degree. More specifically, "controlling" as used herein means that the active ingredient can kill the respective parasite, inhibit its growth, or inhibit its proliferation.

Examples of arthropods include, but without any limitation:
from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.; from the order of the Heteropterida, for example *Cimex* spp., *Triatoma* spp., *Rhodnius* spp., *Panstrongylus* spp.; as well as nuisance and hygiene pests from the order of the Blattarida.

In addition, among the arthropods, examples of Acari include the following, but without any limitation:
from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus (Boophilus)* spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Examples of parasitic protozoa include, but without any limitation:
Mastigophora (*Flagellata*), for example Trypanosomatidae, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, for example Trichomonadidae, for example, *Giardia lamblia, G. canis*.

Sarcomastigophora (Rhizopoda) such as Entamoebidae, for example, *Entamoeba histolytica*, Hartmanellidae, for example, *Acanthamoeba* sp., *Harmanella* sp.

Apicomplexa (Sporozoa) such as Eimeridae, for example, *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii*, *Globidium* spec., *Isospora belli, I. canis, I. felis, I. ohioensis, I. rivolta, I. spec., I. suis, Cystisospora* spec., *Cryptosporidium* spec., in particular *C. parvum*; such as Toxoplasmadiae, for example, *Toxoplasma gondii, Hammondia heydornii, Neospora caninum, Besnoitia besnoitii*; such as Sarcocystidae, for example, *Sarcocystis bovicanis, S. bovihominis, S. ovicanis, S. ovifelis, S. neurona, S. spec., S. suihominis*, such as Leucozoidae, for example, *Leucozytozoon simondi*, such as Plasmodiidae, for example, *Plasmodium berghei, P. falciparum, P. malariae, P. ovale, P. vivax*, P. spec., such as Piroplasmea, for example, *Babesia argentina, B. bovis, B. canis, B. spec., Theileria parva, Theileria* spec., such as Adeleina, for example, *Hepatozoon canis, H. spec*.

Examples of pathogenic endoparasites, which are helminths, include platyhelmintha (e.g. monogenea, cestodes and trematodes), nematodes, acanthocephala, and pentastoma. Further helminths include, but without any limitation:
Monogenea: e.g.: *Gyrodactylus* spp., *Dactylogyrus* spp., *Polystoma* spp.

Cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.

From the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.

Nematodes: Trichinellida, for example: *Trichuris* spp., *Capillaria* spp., *Trichomosoides* spp., *Trichinella* spp.

From the order of the Tylenchida, for example: *Micronema* spp., *Strongyloides* spp.

From the order of the Rhabditina for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp., From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal keeping, the inventive active ingredients are adminstered by methods commonly known in the art, such as enterally, parenterally, dermally or nasally, in the form of suitable preparations. Administration may be prophylactic or therapeutic.

Thus, one embodiment of the present invention refers to inventive compounds for use as a medicament.

A further aspect relates to inventive compounds for use as an antiendoparasitic agent, in particular a helminthicidal agent or antiprotozoic agent. For example, the inventive compounds are suitable for use as an antiendoparasitic agent, in particular a helmithincidal agent or antiprotozoic agent, for example in animal husbandry, in animal breeding, in animal housing and in the hygiene sector.

Yet a further aspect relates to inventive compounds for use as an antiectoparasitic agent, in particular an arthropodicidal agent, such as an insecticide or acaricide. For example, inventive compounds are suitable for use as an antiectoparasitic agent, especially an arthropodicidal agent such as an insecticide or acaricide, for example in animal husbandry, in animal breeding, in animal housing and in the hygiene sector.

The active ingredients of the formula (I) and compositions comprising them are suitable for protection of industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In one embodiment of the invention, the inventive compositions also comprise at least one further insecticide and/or at least one fungicide.

In a further embodiment, this inventive composition is a ready-to-use composition, meaning that it can be applied to the material in question without further modifications. Useful further insecticides or fungicides include those mentioned above.

It has also been found that, surprisingly, the inventive active ingredients and compositions can be used to protect objects which come into contact with saltwater or brackish water, especially hulls, screens, nets, buildings, moorings and signalling systems, against fouling. The inventive active ingredients and compositions can again be used alone or in combinations with other active ingredients as antifouling compositions.

Elucidation of the Processes and Intermediates

The preparation and use examples which follow illustrate the invention without limiting it. The products were characterized by means of 1H NMR spectroscopy and/or LC-MS (liquid chromatography-mass spectrometry) and/or GC-MS (gas chromatography-mass spectrometry).

The log P values were determined analogously to OECD Guideline 117 (EC Directive 92/69/EEC) by HPLC (high-performance liquid chromatography) using reversed-phase columns (C 18), by the following methods:

[a] LC-MS determination in the acidic range is effected at pH 2.7 with 0.1% aqueous formic acid and acetonitrile (containing 0.1% formic acid) as eluents with a linear gradient from 10% acetonitrile to 95% acetonitrile; or with 0.025% aqueous trifluoroacetic acid and acetonitrile (containing 0.025% trifluoroacetic acid) as eluents with a linear gradient from 50% acetonitrile to 80% acetonitrile.

[b] LC-MS determination in the neutral range is effected at pH 7.8 with 0.001 molar aqueous ammonium hydrogencarbonate solution and acetonitrile as eluents; linear gradient from 10% acetonitrile to 95% acetonitrile.

Calibration is effected with solutions of a homologous series of unbranched alkan-2-ones (having 3 to 16 carbon atoms) with known log P values (log P values determined on the basis of the retention times by linear interpolation between two successive alkanones).

The NMR spectra were measured with a Bruker II Avance 400, in some cases equipped with a 1.7 mm TCI probe head. In isolated cases, the NMR spectra were determined using a Bruker Avance II 600.

The NMR data for selected examples are listed in conventional form (δ values, multiplet splitting, number of hydrogen atoms). The splitting of the signals was described as follows: s (singlet), d (doublet), t (triplet), q (quartet), m (multiplet), broad (for broad signals). Solvents used were $CD_3CN$, $CDCl_3$ or D6-DMSO, and tetramethylsilane (0.00 ppm) was used as reference.

PREPARATION EXAMPLES

Preparation Example 1: 2-{2-Fluoro-4-methyl-5-[(2,2,2-trifluoroethyl)sulphinyl]phenyl}-1,2,4-triazine-3,5(2H,4H)-dione (Ex. No. 1)

Stage 1: Diethyl [2-(2-{2-fluoro-4-methyl-5-[(2,2,2-trifluoroethyl)sulphanyl]phenyl}hydrazinylidene)-1,3-dioxopropane-1,3-diyl]biscarbamate

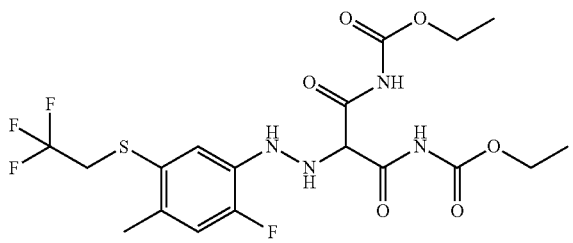 [SMILES: CCOC(=O)NC(=O)C(NNc1cc(SCC(F)(F)F)c(C)cc1F)C(=O)NC(=O)OCC]

10.0 g (41.7 mmol) of 2-fluoro-4-methyl-5-[(2,2,2-trifluoroethyl)sulphanyl]aniline were initially charged at 0° C. in 100 ml of acetic acid, and 12 ml of concentrated hydrochloric acid were added. After the addition of 2.90 g (41.7 mmol) of sodium nitrite and 10.8 g (41.7 mmol) of diethyl (1,3-dioxopropane-1,3-diyl)biscarbamate, the reaction mixture was stirred for 1 hour. Subsequently, 10.3 g (125.1 mmol) of sodium acetate were added at 0° C. and the mixture was stirred at room temperature overnight. The reaction mixture was poured onto ice-water and the precipitate formed was filtered off with suction, washed with diethyl ether and dried under reduced pressure. This gave 7.00 g (94% purity by LC/MS, 34% of theory) of product as a brown solid.

log P[a]: 4.07; 1H NMR (D6-DMSO, 400 MHz) δ ppm: 13.03 (bs, 1H), 11.31 (bs, 1H), 10.49 (bs, 1H), 8.07 (d, 1H), 7.32 (d, 1H), 4.21-4.04 (m, 6H), 2.35 (s, 3H), 1.27-1.22 (m, 6H)

Stage 2: Ethyl [(2-{2-fluoro-4-methyl-5-[(2,2,2-trifluoroethyl)sulphanyl]phenyl}-3,5-dioxo-2,3,4,5-tetrahydro-1,2,4-triazin-6-yl)carbonyl]arbamate

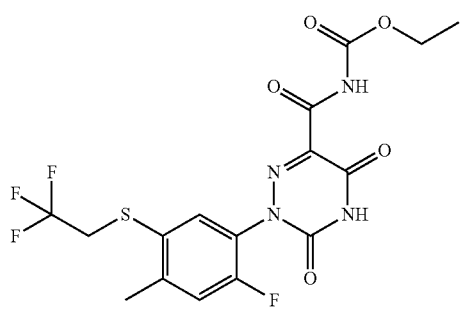 [SMILES: CCOC(=O)NC(=O)c1nn(-c2cc(SCC(F)(F)F)c(C)cc2F)c(=O)[nH]c1=O]

To a solution of 7.00 g (13.7 mmol) of diethyl [2-(2-{2-fluoro-4-methyl-5-[(2,2,2-trifluoroethyl)sulphanyl]phenyl}hydrazinylidene)-1,3-dioxopropane-1,3-diyl]biscarbamate in 70 ml of acetic acid were added, at room temperature, 1.12 g (13.7 mmol) of sodium acetate. The reaction mixture was refluxed for 6 hours, cooled and then poured onto ice-water. The precipitate was filtered off with suction, washed with diethyl ether and dried under reduced pressure. In this way, 5.00 g (93% purity by LC/MS, 79% of theory) of product were obtained as a pale brownish solid.

log P[a]: 2.50; 1H NMR (D6-DMSO, 400 MHz) δ ppm: 12.90 (bs, 1H), 11.52 (bs, 1H), 7.78 (d, 1H), 7.44 (d, 1H), 4.15 (q, 2H), 3.94 (q, 2H), 2.45 (s, 3H), 1.21 (t, 3H)

Stage 3: 2-{2-Fluoro-4-methyl-5-[(2,2,2-trifluoroethyl)sulphanyl]phenyl}-3,5-dioxo-2,3,4,5-tetrahydro-1,2,4-triazine-6-carboxylic acid

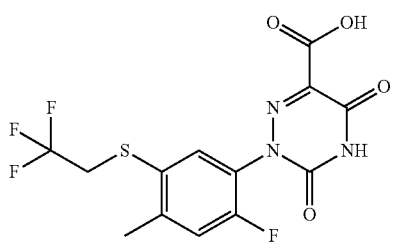 [SMILES: Cc1cc(F)c(-n2nc(C(=O)O)c(=O)[nH]c2=O)cc1SCC(F)(F)F]

A solution of 5.00 g (11.1 mmol) of ethyl [(2-{2-fluoro-4-methyl-5-[(2,2,2-trifluoroethyl)sulphanyl]phenyl}-3,5-dioxo-2,3,4,5-tetrahydro-1,2,4-triazin-6-yl)carbonyl]carbamate in 50 ml of concentrated hydrochloric acid was stirred at reflux for 4 hours and then at room temperature overnight. After cooling, the reaction mixture was poured onto ice-water. The precipitate was filtered off with suction, washed with diethyl ether and dried under reduced pressure. 2.30 g (98% purity by LC/MS, 55% of theory) of product were isolated in solid form.

log P[a]: 1.79; 1H NMR (D6-DMSO, 400 MHz) δ ppm: 12.75 (bs, 1H), 7.79 (d, 1H), 7.43 (d, 1H), 3.91 (q, 2H), 2.45 (s, 3H)

Stage 4: 2-{2-Fluoro-4-methyl-5-[(2,2,2-trifluoroethyl)sulphanyl]phenyl}-1,2,4-triazine-3,5(2H,4H)-dione

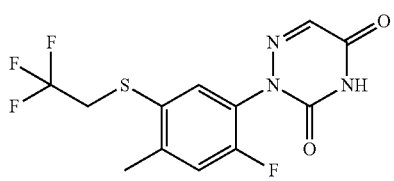

2.30 g (6.06 mmol) of 2-{2-fluoro-4-methyl-5-[(2,2,2-trifluoroethyl)sulphanyl]phenyl}-3,5-dioxo-2,3,4,5-tetrahydro-1,2,4-triazine-6-carboxylic acid were initially charged in 20 ml of diphenyl ether and stirred at 220° C. for 6 hours. After cooling, the crude mixture was purified by means of MPLC using silica gel (100-200 mesh) with 20% ethyl acetate in petroleum ether. 1.20 g (99% purity by LC/MS, 59% of theory) of the title compound were isolated as a yellowish solid.

log P[a]: 2.45; 1H NMR (D6-DMSO, 400 MHz) δ ppm: 12.50 (bs, 1H), 7.76 (d, 1H), 7.70 (s, 1H), 7.41 (d, 1H), 3.93 (q, 2H), 2.44 (s, 3H)

Stage 5: 2-{2-Fluoro-4-methyl-5-[(2,2,2-trifluoro-ethyl)sulphinyl]phenyl}-1,2,4-triazine-3,5(2H,4H)-dione (Ex. No. 1)

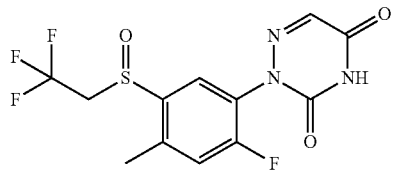

To a solution of 200 mg (0.60 mmol) of 2-{2-fluoro-4-methyl-5-[(2,2,2-trifluoroethyl)sulphanyl]phenyl}-1,2,4-triazine-3,5(2H,4H)-dione in acetone/water (1:1) were added 91 mg (0.60 mmol) of Oxone®. The reaction mixture was stirred at room temperature for 2 hours, then diluted with water and extracted repeatedly with ethyl acetate. The combined organic phases were washed with water and saturated sodium chloride solution, dried over sodium sulphate and filtered. The solvent was removed under reduced pressure. 150 mg (98% purity by LC/MS, 72% of theory) of the title compound were isolated as a yellowish solid.

log P[a]: 1.58; 1H NMR (D6-DMSO, 400 MHz) δ ppm: 12.45 (bs, 1H), 8.02 (d, 1H), 7.71 (s, 1H), 7.52 (d, 1H), 4.34-4.22 (m, 1H), 4.04-3.93 (m, 1H), 2.43 (s, 3H)

Preparation Example 2: 2-{2-Fluoro-4-methyl-5-[(2,2,2-trifluoroethyl)sulphanyl]phenyl}-4-methyl-1,2,4-triazine-3,5(2H,4H)-dione (Ex. No. 3)

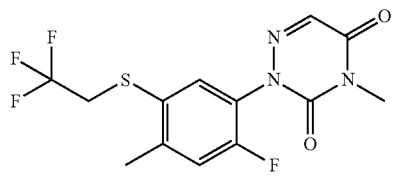 [SMILES: Cc1cc(F)c(-n2ncc(=O)n(C)c2=O)cc1SCC(F)(F)F]

To a stirred solution of 500 mg (1.41 mmol) of 2-{2-fluoro-4-methyl-5-[(2,2,2-trifluoroethyl)sulphanyl]phenyl}-1,2,4-triazine-3,5(2H,4H)-dione in 5 ml of N,N-dimethylformamide were added, at 0° C., 176 μl (400 mg, 2.82 mmol) of methyl iodide and 390 mg (2.82 mmol) of potassium carbonate. The reaction mixture was stirred at room temperature for 3 hours, then diluted with water and extracted repeatedly with ethyl acetate. The combined organic phases were washed with water and saturated sodium chloride solution, dried over sodium sulphate and filtered. The solvent was removed under reduced pressure and the crude product was purified by means of MPLC using silica gel (100-200 mesh) with 26% ethyl acetate in petroleum ether. 350 mg (100% purity by LC/MS, 67% of theory) of the title compound were isolated as a yellowish solid.

log P[a]: 2.94; 1H NMR (CDCl₃, 400 MHz) δ ppm: 7.58-7.56 (m, 2H), 7.14 (d, 1H), 3.41 (s, 3H), 3.35 (q, 2H), 2.54 (s, 3H)

Preparation Example 3: 2-{2-Fluoro-4-methyl-5-[(2,2,2-trifluoroethyl)sulphinyl]phenyl}-4-methyl-1,2,4-triazine-3,5(2H,4H)-dione (Ex. No. 2)

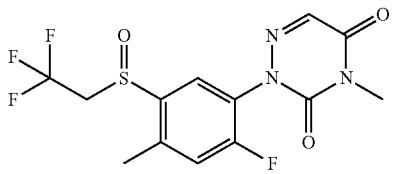 [SMILES: Cc1cc(F)c(-n2ncc(=O)n(C)c2=O)cc1S(=O)CC(F)(F)F]

To a solution of 200 mg (0.57 mmol) of 2-{2-fluoro-4-methyl-5-[(2,2,2-trifluoroethyl)sulphanyl]phenyl}-4-methyl-1,2,4-triazine-3,5(2H,4H)-dione in acetone/water (1:1) were added 87 mg (0.56 mmol) of Oxone®. The reaction mixture was stirred at room temperature for 2 hours, then diluted with water and extracted repeatedly with ethyl acetate. The combined organic phases were washed with water and saturated sodium chloride solution, dried over sodium sulphate and filtered. The solvent was removed under reduced pressure and the crude product was washed with n-pentane. 170 mg (98% purity by LC/MS, 81% of theory) of the title compound were isolated as a yellowish solid.

log P[a]: 1.94; 1H NMR (CDCl₃, 400 MHz) δ ppm: 8.06 (d, 1H), 7.58 (s, 1H), 7.18 (d, 1H), 3.49-3.42 (m, 5H), 2.46 (3H)

Preparation Example 4: 1-{2-Fluoro-4-methyl-5-[(2,2,2-trifluoroethyl)sulphanyl]phenyl}-6-methyl-2,4-dioxo-1,2,3,4-tetrahydropyrimidine-5-carbonitrile (Ex. No. 17)

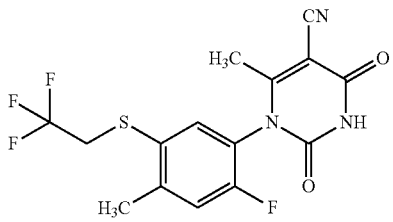 [SMILES: Cc1cc(F)c(-n2c(C)c(C#N)c(=O)[nH]c2=O)cc1SCC(F)(F)F]

200 mg (0.84 mmol) of 2-fluoro-4-methyl-5-[(2,2,2-trifluoroethyl)sulphanyl]aniline were heated under reflux in 3 ml of dimethylformamide with 190 mg (0.84 mmol) of ethyl [(2Z)-2-cyano-3-ethoxybut-2-enoyl]carbamate for 18 h. After removing the solvent under reduced pressure, the remaining residue was purified by column chromatography by means of MPLC using RP(C-18) with water/acetonitrile. This gave 35 mg (92% purity by LC/MS, 11% of theory) of product.

log P[a]: 2.43; 1H NMR (D6-DMSO, 400 MHz) δ ppm: 12.33 (s, 1H), 7.83-7.82 (m, 1H), 7.49-7.47 (m, 1H), 4.06-3.93 (m, 2H), 2.43 (s, 3H), 2.13 (s, 3H)

Preparation Example 5: 1-{2-Fluoro-4-methyl-5-[(2,2,2-trifluoroethyl)sulphinyl]phenyl}-6-methyl-2,4-dioxo-1,2,3,4-tetrahydropyrimidine-5-carbonitrile (Ex. No. 16)

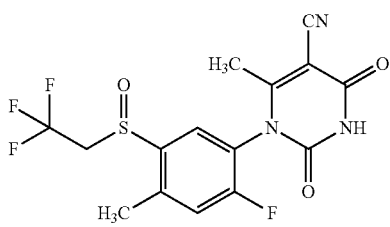 [SMILES: Cc1cc(F)c(-n2c(C)c(C#N)c(=O)[nH]c2=O)cc1S(=O)CC(F)(F)F]

100 mg (0.392 mmol) of 2-fluoro-4-methyl-5-[(2,2,2-trifluoroethyl)sulphinyl]aniline are heated under reflux in 10 ml of ethanol and a catalytic amount of acetic acid with 80 mg (0.354 mmol) of ethyl [(2Z)-2-cyano-3-ethoxybut-2-enoyl]carbamate [CAS-RN 925982-34-9] for 18 h. After cooling, the mixture is concentrated under reduced pressure. The remaining residue is taken up in 5 ml of dimethylformamide and stirred at 140° C. for a further 18 h. After removing the solvent under reduced pressure, the remaining residue is purified by column chromatography by means of MPLC using RP(C-18) with water/acetonitrile. This gives 18.8 mg (83% purity by LC/MS, 10% of theory) of product as a diastereomer mixture.

1H NMR (D6-DMSO, 400 MHz) δ ppm: 12.31 (s, 1H), 8.14-8.12 (m, 1H), 7.61-7.58 (m, 1H), 4.36-3.88 (m, 2H), 2.45 (s, 3H), 2.20 (s, 3H)

Preparation Example 6: 1-{2,4-Diethyl-5-[(2,2,2-trifluoroethyl)sulphanyl]phenyl}-6-methyl-2,4-dioxo-1,2,3,4-tetrahydropyrimidine-5-carbonitrile (Ex. No. 18)

Stage 1: 1-{2,4-Diethyl-5-[(2,2,2-trifluoroethyl)sulphinyl]phenyl}-6-methyl-2,4-dioxo-1,2,3,4-tetrahydropyrimidine-5-carbonitrile

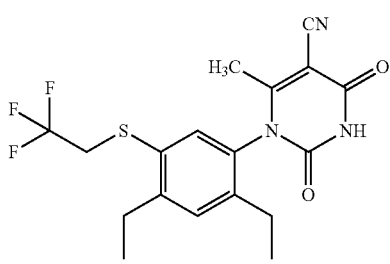 [SMILES: CCc1cc(CC)c(-n2c(C)c(C#N)c(=O)[nH]c2=O)cc1SCC(F)(F)F]

250 mg (0.95 mmol) of 2,4-diethyl-5-[(2,2,2-trifluoroethyl)sulphanyl]aniline were heated under reflux in 10 ml of ethanol and a catalytic amount of acetic acid with 195 mg (0.862 mmol) of ethyl [(2Z)-2-cyano-3-ethoxybut-2-enoyl]carbamate for 18 h. After cooling, the reaction mixture was concentrated under reduced pressure. The remaining residue was taken up in 5 ml of dimethylformamide and heated under reflux for a further 18 h. After removing the solvent under reduced pressure, the remaining residue was purified by column chromatography by means of MPLC using RP(C-18) with water/acetonitrile. This gave 80 mg (94% purity by LC/MS, 20% of theory) of product.

log P[a]: 3.16; 1H NMR (D6-DMSO, 400 MHz) δ ppm: 12.19 (s, 1H), 7.62 (s, 1H), 7.33 (s, 1H), 4.05-3.91 (m, 2H), 2.79-2.73 (m, 2H), 2.53-2.33 (m, 2H), 2.01 (s, 3H), 1.21 (t, 3H), 1.10 (t, 3H).

Stage 2: 1-{2,4-Diethyl-5-[(2,2,2-trifluoroethyl)sulphinyl]phenyl}-6-methyl-2,4-dioxo-1,2,3,4-tetrahydropyrimidine-5-carbonitrile (Ex. No. 18)

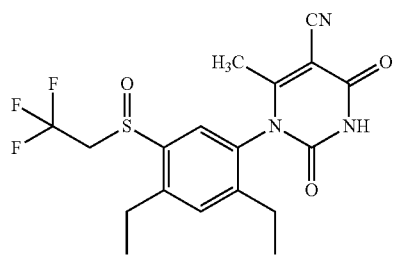 [SMILES: CCc1cc(CC)c(S(=O)CC(F)(F)F)cc1-n1c(C)c(C#N)c(=O)[nH]c1=O]

50 mg (0.13 mmol) of 1-{2,4-diethyl-5-[(2,2,2-trifluoroethyl)sulphanyl]phenyl}-6-methyl-2,4-dioxo-1,2,3,4-tetrahydropyrimidine-5-carbonitrile was initially charged at 0° C. in 3 ml of acetic acid. After the addition of catalytic amounts of sodium tungstate at 0° C., 155 mg (0.137 mmol) of 3% aqueous hydrogen peroxide solution were added thereto in portions and the reaction mixture was stirred at room temperature for 24 h. After the addition of a 33% aqueous bisulphite solution, the mixture was extracted with dichloromethane. The combined organic phases were washed with water, dried over sodium sulphate and filtered. After removing the solvent under reduced pressure, the residue was purified by column chromatography by means of MPLC using RP(C-18). With water/acetonitrile, 36 mg of product were obtained as a pale yellow solid (89% purity by LC/MS, 62% of theory).

log P[a]: 2.15; log P[b]: 1.55; 1H NMR (D6-DMSO, 400 MHz) δ ppm: 12.18 (s, 1H), 7.96 (s, 1H), 7.51 (s, 1H), 4.29-3.84 (m, 2H), 2.76 (m, 2H), 2.51 (m, 2H), 2.00 (s, 3H), 1.27 (t, 3H), 1.15 (t, 3H).

Preparation Example 7: Chiral oxidation to (−)- and (+)-2-[2-fluoro-4-methyl-5-(2,2,2-trifluoroethylsulphinyl)phenyl]-4-methyl-1,2,4-triazine-3,5-diones (Ex. Nos. 28 and 29)

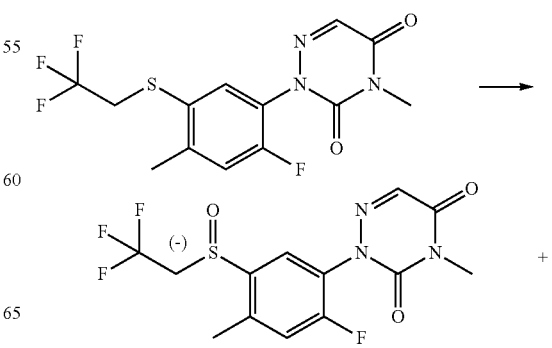

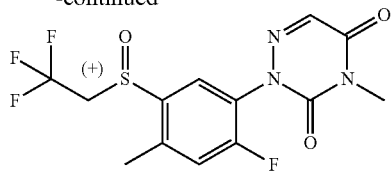

16.0 mg (0.06 mmol) of vanadium acetylacetonate and 28.6 mg (0.09 mmol) of (S)-(2,4-di-tert-butyl-6-{(E)-[(1-hydroxy-3,3-dimethylbutan-2-yl)imino]methyl}phenol were initially charged in 1 ml of chloroform and stirred at room temperature for 1 h. 200.0 mg (0.57 mmol) of 2-[2-fluoro-4-methyl-5-(2,2,2-trifluoroethylsulphanyl)phenyl]-4-methyl-1,2,4-triazine-3,5-dione (Ex. No. 3) were dissolved in 1 ml of chloroform and added thereto. The solution was stirred at room temperature for a further 5 minutes. A solution of 66.8 mg (59 ml, 0.68 mmol) of 35% $H_2O_2$ and 101 mg (100 ml) of pH 7 buffer solution ($KH_2PO_4$/$Na_2HPO_4$) was metered in over the course of 2 hours. Subsequently, the mixture was stirred at room temperature for a further 2 hours and left to stir at room temperature overnight. The course of the reaction was monitored by means of TLC: reactant still present, about 50% conversion. Addition of another 159 ml of $H_2O_2$/pH 7 buffer solution over a period of 2 hours. TLC monitoring showed no change, so the reaction was stopped and diluted with 2 ml of chloroform, and a couple of ml of 1M sodium thiosulphate solution were added. The phases were separated and the solvent was removed under reduced pressure. This gave 199 mg of a mixture which, by LC/MS, consisted of 34% 2-[2-fluoro-4-methyl-5-(2,2,2-trifluoroethylsulphanyl)phenyl]-4-methyl-1,2,4-triazine-3,5-dione (Ex. No. 3) and 56% 2-[2-fluoro-4-methyl-5-(2,2,2-trifluoroethylsulphinyl)phenyl]-4-methyl-1,2,4-triazine-3,5-dione (Ex. No. 2).

The enantiomeric excess was determined by HPLC on a chiral phase (Chiracel OD-RH 150) with a ratio of (−) to (+) enantiomer of 26.1:73.9.

(−)-2-[2-fluoro-4-methyl-5-(2,2,2-trifluoroethylsulphinyl)phenyl]-4-methyl-1,2,4-triazine-3,5-dione (Ex. No. 28), specific rotation: −34.7 in acetonitrile (c=0.009)

(+)-2-[2-fluoro-4-methyl-5-(2,2,2-trifluoroethylsulphinyl)phenyl]-4-methyl-1,2,4-triazine-3,5-dione (Ex. No. 29), specific rotation: 33.7 in acetonitrile (c=0.009)

Preparation Example 8: 1-{2-fluoro-4-methyl-5-[(2,2,2-trifluoroethyl)sulphanyl]phenyl}pyrimidine-2,4(1H,3H)-dione (Ex. No. 55)

Stage 1: (2E)-3-Ethoxyacryloyl chloride

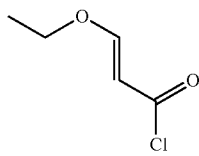

To 228 g (1.8 mol) of oxalyl chloride were added dropwise, at 0° C., 86.5 g (1.2 mol) of ethyl vinyl ether, at a sufficiently slow rate that the internal temperature did not rise above 5° C. The reaction mixture was stirred at 0° C. for 2 h and at room temperature overnight, then freed of excess oxalyl chloride under reduced pressure. The black liquid residue obtained contained 179 g of 4-ethoxy-2-oxobut-3-enoyl chloride (about 83% yield at about 90% purity).

$^1$H NMR (CDCl$_3$, 400 MHz) δ ppm: 7.89 (d, 1H), 6.05 (d, 1H), 4.12 (q, 2H), 1.40 (t, 3H). $^{13}$C NMR (CDCl$_3$, 400 MHz) δ ppm: 176.9; 169.0; 168.9; 98.9; 69.0; 14.3.

The 4-ethoxy-2-oxobut-3-enoyl chloride was heated to 120° C. on a reflux condenser for 30 min. The black liquid reaction mixture was purified by means of distillation (0.9-1.3 mbar, main fraction at 40-44° C.); 88.6 g (90% purity, 49% of theory) of the title compound were obtained as a pale yellow liquid.

$^1$H NMR (CDCl$_3$, 400 MHz) δ ppm: 7.78 (d, 1H), 5.51 (d, 1H), 4.05 (q, 2H), 1.40 (t, 3H). $^{13}$C NMR (CDCl$_3$, 400 MHz) δ ppm: 168.1; 164.7; 102.9; 68.7; 14.4.

Stage 2: (2E)-3-Ethoxyacryloyl isocyanate

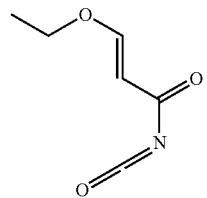

Under an argon atmosphere, 26.49 g (149.9 mmol) of silver cyanate were heated to reflux in dry toluene (120 ml) for 30 min, then, at 100° C., a solution of 11.65 g (86.8 mmol) of (2E)-3-ethoxyacryloyl chloride in dry toluene (30 ml) was added. The reaction mixture was heated to reflux for 30 min, then cooled first to room temperature and then to 0° C. The supernatant solution of the title compound was decanted off and removed from the silver chloride precipitate with the aid of a syringe, and converted further without further purification; a sample was concentrated and then analysed by NMR spectroscopy.

$^1$H NMR (CDCl$_3$, 400 MHz) δ ppm: 7.70 (d, 1H), 5.29 (d, 1H), 4.00 (q, 2H), 1.38 (t, 3H). $^{13}$C NMR (CDCl$_3$, 400 MHz) δ ppm: 166.8; 164.3; 139.4; 100.7; 68.0; 14.3.

Stage 3: (2E)-3-Ethoxy-N-({2-fluoro-4-methyl-5-[(2,2,2-trifluoroethyl)sulphanyl]phenyl}carbamoyl)-acrylamide

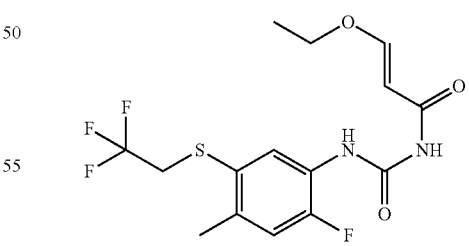

Under an argon atmosphere, 12.22 g (86.6 mmol) of 2-fluoro-4-methyl-5-[(2,2,2-trifluoroethyl)sulphanyl]aniline in dry N,N-dimethylformamide (50 ml) were initially charged together with 11.8 g of activated 4 Å molecular sieve, the mixture was cooled to −20° C., and the toluenic solution of (2E)-3-ethoxyacryloyl isocyanate obtained in stage 2 was added dropwise at such a rate that the internal temperature did not rise above −15° C. The reaction mixture was stirred at room temperature overnight, then filtered and concentrated under reduced pressure. The yellow solid obtained was triturated with cyclohexane, filtered and washed with a little cyclohexane. This gave 10.6 g (95% pure, 46% of theory) of the title compound as a yellowish solid.

log P[a]: 3.78; log P[b]: 3.70; $^1$H NMR (D$^6$-DMSO, 400 MHz) δ ppm: 11.11 (s, 1H), 10.60 (s, 1H), 8.37 (d, 1H), 7.72 (d, 1H), 7.29 (d, 1H), 5.59 (d, 1H), 4.01 (q, 2H), 3.79 (q, 2H), 2.38 (s, 3H), 1.27 (t, 3H)

Stage 4: 1-{2-Fluoro-4-methyl-5-[(2,2,2-trifluoro-ethyl)sulphanyl]phenyl}pyrimidine-2,4(1H,3H)-dione (Ex. No. 55)

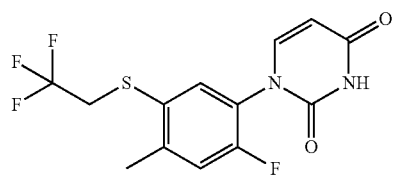 [SMILES: Cc1cc(F)c(-n2ccc(=O)[nH]c2=O)cc1SCC(F)(F)F]

To a solution of 10.0 g (26.3 mmol) of (2E)-3-ethoxy-N-({2-fluoro-4-methyl-5-[(2,2,2-trifluoroethyl)sulphanyl]phenyl}carbamoyl)acrylamide in ethanol (37 ml) were added 117 ml (233 mmol) of 2M sulphuric acid, and the reaction mixture was heated to reflux with stirring overnight. After cooling to room temperature, ethanol was removed on a rotary evaporator under reduced pressure and the sulphuric acid phase was admixed with dichloromethane. The solid that was insoluble here was filtered off with suction and dried. This gave 7.50 g (100% pure, 85% of theory) of the title compound as a light brown solid. The dried and concentrated dichloromethane phase contained only a little product and was discarded.

log P[a]: 2.13; log P[b]: 2.06; $^1$H NMR (D$^6$-DMSO, 400 MHz) δ ppm: 11.58 (s, 1H), 7.76 (d, 1H), 7.68 (d, 1H), 7.39 (d, 1H), 5.74-5.71 (m, 1H), 3.99 (q, 2H), 2.41 (s, 3H)

Preparation Example 9: 1-{2-Fluoro-4-methyl-5-[(2,2,2-trifluoroethyl)sulphinyl]phenyl}pyrimidine-2,4(1H,3H)-dione (Ex. No. 56)

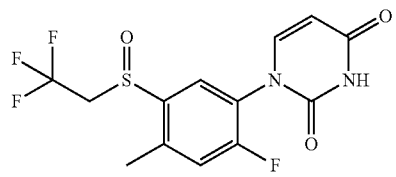 [SMILES: Cc1cc(F)c(-n2ccc(=O)[nH]c2=O)cc1S(=O)CC(F)(F)F]

To a solution of 1.76 g (5.27 mmol) of 1-{2-fluoro-4-methyl-5-[(2,2,2-trifluoroethyl)sulphanyl]phenyl}pyrimidine-2,4(1H,3H)-dione in acetonitrile (35 ml) were added, at 0° C., 43.4 mg (0.13 mmol) of sodium tungstate(VI) dihydrate and, dropwise, 6.27 g (5.53 mmol) of a 3% aqueous hydrogen peroxide solution. The reaction mixture was stirred at room temperature overnight, then another 2.98 g (2.63 mmol) of a 3% aqueous hydrogen peroxide solution were added and the mixture was stirred at room temperature overnight again. Sodium bisulphite solution (40% in water) and dichloromethane were added, and the mixture was extracted with dichloromethane. The combined organic phases were washed with saturated aqueous ammonium chloride solution, dried over magnesium sulphate, filtered and freed of the solvent under reduced pressure. Purification by column chromatography on silica gel by means of MPLC with cyclohexane/ethyl acetate as eluent gave 1.43 g (97% pure, 75% of theory) of the title compound as a yellowish solid.

log P[a]: 1.30; log P[b]: 1.24; $^1$H NMR (D$^6$-DMSO, 400 MHz) δ ppm: 11.62 (s, 1H), 7.98 (d, 1H), 7.74 (d, 1H), 7.52 (d, 1H), 5.79-5.76 (m, 1H), 4.29-4.16 (m, 1H), 4.13-4.01 (m, 1H), 2.44 (s, 3H)

Preparation Example 10: 1-{2-Fluoro-4-methyl-5-[(2,2,2-trifluoroethyl)sulphinyl]phenyl}-3-methylpyrimidine-2,4(1H,3H)-dione (Ex. No. 54)

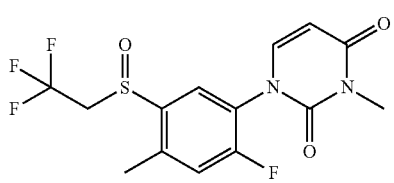 [SMILES: Cc1cc(F)c(-n2ccc(=O)n(C)c2=O)cc1S(=O)CC(F)(F)F]

To a solution of 200 mg (0.57 mmol) of 1-{2-fluoro-4-methyl-5-[(2,2,2-trifluoroethyl)sulphinyl]phenyl}pyrimidine-2,4(1H,3H)-dione in dry N,N-dimethylformamide (3 ml) were added, under an argon atmosphere at 0° C., first 243 mg (1.71 mmol) of methyl iodide, then 28.5 mg (0.71 mmol) of sodium hydride (60% suspension in mineral oil). The reaction mixture was stirred at 0° C. for 2 h, then poured onto ice-water and extracted with ethyl acetate. The combined organic phases were washed with water, saturated aqueous sodium chloride solution, dried over magnesium sulphate, filtered and freed of the solvent under reduced pressure. Purification by column chromatography on silica gel by means of MPLC with cyclohexane/ethyl acetate as eluent gave 124 mg (100% pure, 60% of theory) of the title compound as a colourless solid.

log P[a]: 1.66; log P[b]: 1.61; $^1$H NMR (D$^6$-DMSO, 400 MHz) δ ppm: 7.99 (d, 1H), 7.78 (d, 1H), 7.54 (d, 1H), 5.92 (d, 1H), 4.30-4.16 (m, 1H), 4.12-3.98 (m, 1H), 3.21 (s, 3H), 2.45 (s, 3H)

Preparation Example 11: 1-{2-Fluoro-4-methyl-5-[(2,2,2-trifluoroethyl)sulphanyl]phenyl}-3-methyl-pyrimidine-2,4(1H,3H)-dione (Ex. No. 53)

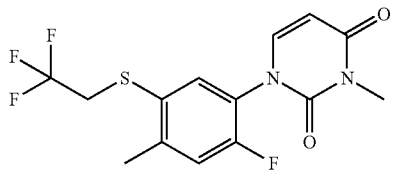 [SMILES: Cc1cc(F)c(-n2ccc(=O)n(C)c2=O)cc1SCC(F)(F)F]

To a solution of 1.67 g (5.0 mmol) of 1-{2-fluoro-4-methyl-5-[(2,2,2-trifluoroethyl)sulphanyl]phenyl}pyrimidine-2,4(1H,3H)-dione in dry N,N-dimethylformamide (15 ml) were added, under an argon atmosphere at 0° C., first 2.13 g (15.0 mmol) of methyl iodide, then 300 mg (7.5 mmol) of sodium hydride (60% suspension in mineral oil). The reaction mixture was stirred at 0° C. to room temperature for 2 h, then poured onto ice-water and extracted with ethyl acetate. The combined organic phases were washed with water, saturated aqueous sodium chloride solution, dried over magnesium sulphate, filtered and freed of the solvent under reduced pressure. Purification by column chromatography on silica gel by means of MPLC with cyclohexane/ethyl acetate as eluent gave 1.58 g (100% pure, 91% of theory) of the title compound as a yellow solid.

log P[a]: 2.59; log P[b]: 2.53; $^1$H NMR (D$^6$-DMSO, 400 MHz) δ ppm: 7.77 (d, 1H), 7.74 (d, 1H), 7.41 (d, 1H), 5.88 (d, 1H), 3.98 (q, 2H), 3.21 (s, 3H), 2.43 (s, 3H)

Preparation Example 12: 3-Ethyl-1-{2-fluoro-4-methyl-5-[(2,2,2-trifluoroethyl)sulphanyl]phenyl}pyrimidine-2,4(1H,3H)-dione (Ex. No. 71)

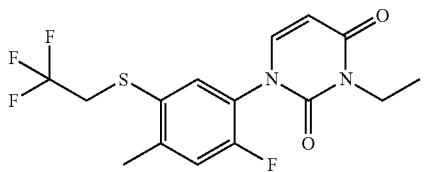 [SMILES: CCn1c(=O)ccn(-c2cc(SCC(F)(F)F)c(C)cc2F)c1=O]

To a solution of 186 mg (0.56 mmol) of 1-{2-fluoro-4-methyl-5-[(2,2,2-trifluoroethyl)sulphanyl]phenyl}pyrimidine-2,4(1H,3H)-dione in dry N,N-dimethylformamide (3 ml) were added 33.4 mg (0.84 mmol) of sodium hydride (60% suspension in mineral oil), the mixture was stirred at room temperature for 15 min, then 174 mg (1.11 mmol) of ethyl iodide were added and the mixture was stirred at room temperature. After 1 h, another 22.3 mg (0.56 mmol) of sodium hydride (60% suspension in mineral oil) and 86.8 mg (0.56 mmol) of ethyl iodide were added and the mixture was stirred at room temperature overnight, then poured onto ice-water and extracted with ethyl acetate. The combined organic phases were washed with water, saturated aqueous sodium chloride solution, dried over magnesium sulphate, filtered and freed of the solvent under reduced pressure. Purification by column chromatography on silica gel by means of MPLC with cyclohexane/ethyl acetate as eluent gave 40.6 mg (97% pure, 20% of theory) of the title compound as a colourless solid.

log P[a]: 2.93; log P[b]: 2.86; $^1$H NMR (D$^6$-DMSO, 400 MHz) δ ppm: 7.78 (d, 1H), 7.72 (d, 1H), 7.41 (d, 1H), 5.86 (d, 1H), 3.99 (q, 2H), 3.86 (q, 2H), 2.42 (s, 3H), 1.12 (t, 3H)

Preparation Example 13: 3-Ethyl-1-{2-fluoro-4-methyl-5-[(2,2,2-trifluoroethyl)sulphinyl]phenyl}pyrimidine-2,4(1H,3H)-dione (Ex. No. 59)

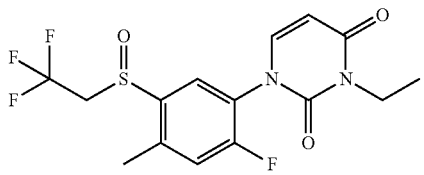 [SMILES: CCn1c(=O)ccn(-c2cc(S(=O)CC(F)(F)F)c(C)cc2F)c1=O]

To a solution of 208 mg (0.57 mmol) of 3-ethyl-1-{2-fluoro-4-methyl-5-[(2,2,2-trifluoroethyl)sulphanyl]phenyl}pyrimidine-2,4(1H,3H)-dione in 5 ml of dichloromethane were added, at 0° C., 135 mg (0.60 mmol) of meta-chloroperbenzoic acid (about 77%). The reaction mixture was stirred at 0° C. for 2 h, washed with 1M sodium hydroxide solution and freed of the solvent under reduced pressure. Purification by column chromatography on silica gel by means of MPLC with cyclohexane/ethyl acetate as eluent gave 145 mg (100% pure, 67% of theory) of the title compound as a colourless solid.

log P[a]: 1.94; log P[b]: 1.88; $^1$H NMR (D$^6$-DMSO, 400 MHz) δ ppm: 8.00 (d, 1H), 7.77 (d, 1H), 7.53 (d, 1H), 5.90 (d, 1H), 4.30-4.12 (m, 1H), 4.12-3.99 (m, 1H), 3.87 (q, 2H), 2.45 (s, 3H), 1.13 (t, 3H)

Preparation Example 14: 3-Methyl-1-{4-methyl-3-[(2,2,2-trifluoroethyl)sulphanyl]phenyl}pyrimidine-2,4(1H,3H)-dione (Ex. No. 58)

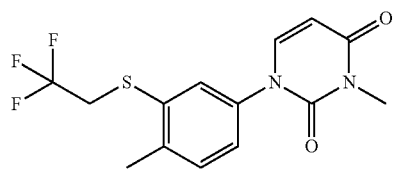 [SMILES: Cc1ccc(-n2ccc(=O)n(C)c2=O)cc1SCC(F)(F)F]

375 mg (1.5 mmol) of {4-methyl-3-[(2,2,2-trifluoroethyl)sulphanyl]phenyl}boric acid, 189 mg (1.5 mmol) of 3-methyluracil, 409 mg (2.25 mmol) of copper(II) acetate, 237 mg (3.0 mmol) of pyridine and 1.0 g of activated 3 Å molecular sieve were stirred in 20 ml of dry dichloromethane at room temperature for 4 d. The reaction mixture was adsorbed on kieselguhr and purified by column chromatography on silica gel by means of MPLC with cyclohexane/ethyl acetate as eluent. This gave 176 mg (93% pure, 33% of theory) of the title compound as a colourless oil.

log P[a]: 2.48; log P[b]: 2.39; $^1$H NMR (D$^6$-DMSO, 400 MHz) δ ppm: 7.71 (d, 1H), 7.61 (d, 1H), 7.37 (d, 1H), 7.27-7.24 (m, 1H), 5.83 (d, 1H), 4.04 (q, 2H), 3.20 (s, 3H), 2.38 (s, 3H)

Preparation Example 15: 3-Methyl-1-{4-methyl-3-[(2,2,2-trifluoroethyl)sulphinyl]phenyl}pyrimidine-2,4(1H,3H)-dione (Ex. No. 57)

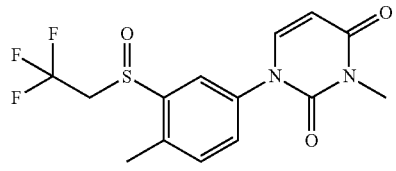 [SMILES: Cc1ccc(-n2ccc(=O)n(C)c2=O)cc1S(=O)CC(F)(F)F]

To a solution of 88.0 mg (0.27 mmol) of 3-methyl-1-{4-methyl-3-[(2,2,2-trifluoroethyl)sulphanyl]phenyl}pyrimidine-2,4(1H,3H)-dione in 10 ml of dichloromethane were added, at 0° C., 62.7 mg (0.28 mmol) of meta-chloroperbenzoic acid (about 77%). The reaction mixture was stirred at 0° C. for 2 h, washed with 1M sodium hydroxide (5 ml) solution and freed of the solvent under reduced pressure. This gave 82 mg (100% pure, 89% of theory) of the title compound as a colourless solid.

log P[a]: 1.50; log P[b]: 1.49; $^1$H NMR (D$^6$-DMSO, 400 MHz) δ ppm: 7.87 (d, 1H), 7.80 (d, 1H), 7.61-7.58 (m, 1H), 7.49 (d, 1H), 5.88 (d, 1H), 4.30-4.12 (m, 1H), 4.09-3.95 (m, 1H), 3.21 (s, 3H), 2.42 (s, 3H)

Synthesis of Anilines of the Formula (IVa)

2,4-Diethyl-5-[(2,2,2-trifluoroethyl)sulphanyl]aniline

Stage 1: 5-N-(2,4-Diethylphenyl)acetamide

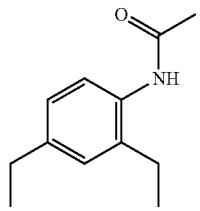

To a solution of 8.40 g (56.3 mmol) of 2,4-diethylaniline in 150 ml of toluene were slowly added dropwise 6.00 g (58.8 mmol) of acetic anhydride, then the mixture was stirred at room temperature for another 18 h. The mixture was freed of the solvent under reduced pressure and the remaining slurry of solids was stirred with water and filtered with suction. This gave 9.50 g of product (100% by 1H NMR, 88% of theory).

1H NMR (D6-DMSO, 400 MHz) δ ppm: 9.20 (broad, 1H), 7.20-7.18 (m, 1H), 7.04 (s, 1H), 6.99-6.97 (m, 1H), 2.55 (m, 4H), 2.02 (s, 3H), 1.16 (t, 3H), 1.10 (t, 3H)

Stage 2: 5-Acetamido-2,4-diethylbenzenesulphonyl chloride

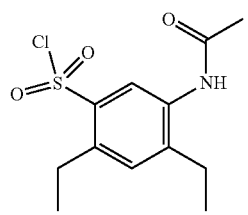 [SMILES: CCc1cc(CC)c(S(=O)(=O)Cl)cc1NC(C)=O]

9.50 g (49.7 mmol) of 5-N-(2,4-diethylphenyl)acetamide were added in portions to 30.0 g (257.5 mmol) of chlorosulphonic acid, and the mixture was stirred at 80° C. for 4 h. After cooling, the mixture was added to ice-water and the solid obtained was filtered off with suction, leaving 10.3 g of product (100% purity by 1H NMR, 72% of theory).

1H NMR (D6-DMSO, 400 MHz) δ ppm: 9.29 (broad, 1H), 7.58 (s, 1H), 7.00 (s, 1H), 2.95 (q, 2H), 2.51 (q, 2H), 2.02 (s, 3H), 1.16 (t, 3H), 1.08 (t, 3H)

Stage 3: N,N'-[Disulphanediylbis(4,6-diethylbenzene-3,1-diyl)]diacetamide

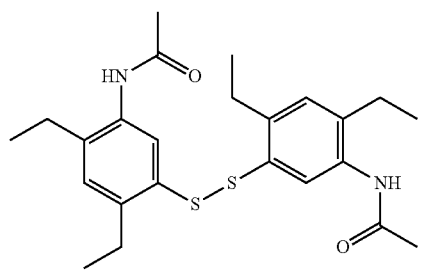 [SMILES: CCc1cc(CC)c(SSc2cc(NC(C)=O)c(CC)cc2CC)cc1NC(C)=O]

13.4 g (46.2 mmol) of 5-acetamido-2,4-diethylbenzenesulphonyl chloride were heated under reflux together with 7.40 g (132.5 mmol) of iron powder in 150 ml of ethanol and 18.7 g of concentrated hydrochloric acid for 12 h. After removing the solvent under reduced pressure, the residue was stirred with water and filtered with suction to obtain 10.3 g of crude product (73% purity by LC-MS, 50% of theory) as a light brown solid.

log P(HCOOH): 4.02

Stage 4: N-{2,4-Diethyl-5-[(2,2,2-trifluoroethyl)sulphanyl]phenyl}acetamide

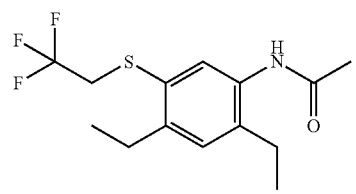 [SMILES: CCc1cc(CC)c(SCC(F)(F)F)cc1NC(C)=O]

10.3 g (23.16 mmol) of N,N'-[disulphanediylbis(4,6-diethylbenzene-3,1-diyl)]diacetamide are initially charged in 60 ml of dimethylformamide, 6.3 g of sodium dithionite, 15.5 g of potassium carbonate and 5.3 g of sodium hydrogenphosphate and 40 ml of water are added, and then the mixture is stirred at 60° C. for 3 h. After cooling, 12 g (57.16 mmol) of 1,1,1-trifluoro-2-iodoethane are added and the mixture is stirred at 80° C. for a further 12 h. After removing the solvent under reduced pressure, the remaining residue is acidified with concentrated hydrochloric acid and the grey precipitate which forms is filtered off with suction. This leaves 11.9 g of product (70% purity by LC-MS, 84% of theory).

log P(HCOOH): 3.07

Stage 5: 2,4-Diethyl-5[(2,2,2-trifluoroethyl)sulphanyl]aniline

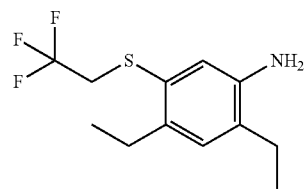 [SMILES: CCc1cc(CC)c(SCC(F)(F)F)cc1N]

11.9 g (39.0 mmol) of N-{2,4-diethyl-5-[(2,2,2-trifluoroethyl)sulfanyl]phenyl}acetamide in 125 ml of 5 molar hydrochloric acid are stirred under reflux for 18 h. The reaction mixture is made alkaline with aqueous sodium hydroxide solution and extracted with dichloromethane. The organic phase is removed, dried over sodium sulphate and freed of the solvent under reduced pressure. This leaves 5.6 g of product as a brown oil (100% purity by 1H NMR, 55% of theory).

1H NMR (D6-DMSO, 400 MHz) δ ppm: 6.81-6.79 (m, 2H), 4.77 (broad, 2H), 3.75-3.67 (q, 2H), 2.63-2.58 (q, 2H), 2.43-2.37 (q, 2H), 1.10 (t, 3H), 1.09 (t, 3H)

Synthesis of Esters of the Formula (I-A-IIIa-Ester)

Ethyl 3-cyclopropyl-1-{2-fluoro-4-methyl-5-[(2,2,2-trifluoroethyl)sulphanyl]phenyl}-2,4-dioxo-1,2,3,4-tetrahydropyrimidine-5-carboxylate

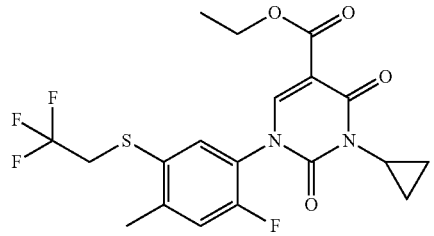 [SMILES: CCOC(=O)c1cn(-c2cc(SCC(F)(F)F)c(C)cc2F)c(=O)n(C2CC2)c1=O]

To a solution of 1.20 g (5.0 mmol) of 2-fluoro-4-methyl-5-[(2,2,2-trifluoroethyl)sulphanyl]aniline in dry tetrahydrofuran (20 ml) were added, at 0° C. under an argon atmosphere, 457 mg (5.0 mmol) of cyclopropyl isocyanate, then the mixture was stirred at 0° C. for 30 min, at room temperature overnight, and at 45° C. for 2 h and at 55° C. for 2 h. After adding another 457 mg (5.0 mmol) of cyclopropyl isocyanate and a few drops of Hünig's base, the reaction mixture was stirred at room temperature overnight, then concentrated under reduced pressure. Reaction monitoring by means of LC-MS indicated formation of the 1-cyclopropyl-3-{2-fluoro-4-methyl-5-[(2,2,2-trifluoroethyl)sulphanyl]phenyl}urea intermediate. The residue was taken up in ethanol (20 ml), 1.14 g (5.25 mmol) of diethyl ethoxymethylenemalonate and 1.70 g (5.35 mmol) of sodium ethoxide solution (21% in ethanol) were added, and the mixture was stirred at room temperature overnight and at 55° C. for 2 h. After cooling to room temperature, the reaction mixture was adjusted to pH 6 with hydrochloric acid, ethanol was removed under reduced pressure and the mixture was extracted with ethyl acetate. The combined organic phases were washed with saturated aqueous sodium chloride solution, dried over magnesium sulphate, filtered and freed of the solvent under reduced pressure. Purification by column chromatography on silica gel by means of MPLC with cyclohexane/ethyl acetate as eluent gave 862 mg (92% pure, 36% of theory) of the title compound as a yellow resinous solid.

log P[a]: 3.07; log P[b]: 3.02; $^1$H NMR (D$^6$-DMSO, 400 MHz) δ ppm: 8.34 (s, 1H), 7.61 (d, 1H), 7.38 (d, 1H), 4.21 (q, 2H), 3.87 (q, 2H), 3.29-3.20 (m, 1H), 2.45 (s, 3H), 1.25 (t, 3H), 1.03-0.90 (m, 4H)

By the above-described processes, the following compounds of the general formula (I) were prepared:

TABLE 1

Compounds of the formula (I) with substructure (I-A-1)

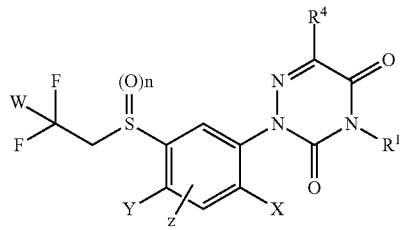

Z = H, W = F and R$^4$ = H

| Ex. No. | n | Y | X | R$^1$ |
|---|---|---|---|---|
| 1 | 1 | CH3 | F | H |
| 2 | 1 | CH3 | F | CH3 |

TABLE 1-continued

Compounds of the formula (I) with substructure (I-A-1)

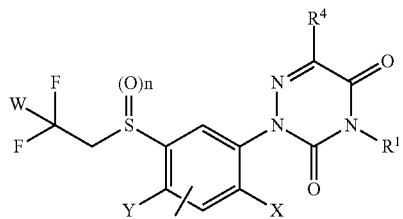

Z = H, W = F and R$^4$ = H

| Ex. No. | n | Y | X | R$^1$ |
|---|---|---|---|---|
| 3 | 0 | CH3 | F | CH3 |
| 4 | 1 | CH3 | CH3 | CH3 |
| 5 | 0 | CH3 | CH3 | CH3 |
| 6 | 1 | CH3 | CH3 | CH2CF3 |
| 7 | 0 | CH3 | CH3 | CH2CF3 |
| 8 | 0 | Cl | Cl | H |
| 9 | 1 | CH3 | F | CH2CF3 |
| 10 | 0 | CH3 | F | CH2CF3 |
| 11 | 1 | Cl | Cl | CH2CF3 |
| 12 | 0 | Cl | Cl | CH$_2$CF$_3$ |
| 13 | 1 | Cl | Cl | CH$_3$ |
| 14 | 0 | Cl | Cl | CH$_3$ |
| 15 | 1 | Cl | Cl | H |
| 19 | 0 | CH$_3$ | F | CH$_2$CH$_3$ |
| 20 | 0 | CH$_3$ | F | CH$_2$CH(CH$_3$)$_2$ |
| 21 | 1 | CH$_3$ | F | CH$_2$CH$_3$ |
| 22 | 1 | CH$_3$ | F | CH$_2$CH(CH$_3$)$_2$ |
| 23 | 0 | CH$_3$ | H | CH$_3$ |
| 24 | 1 | CH$_3$ | H | CH$_3$ |
| 25 | 0 | CH$_3$ | F | cyclopropylmethyl |
| 26 | 0 | CH$_3$ | F | CH(CH$_3$)$_2$ |
| 27 | 1 | CH$_3$ | F | cyclopropylmethyl |
| 28 | 1 | CH$_3$ | F | CH$_3$ |
| 29 | 1 | CH$_3$ | F | CH$_3$ |
| 30 | 1 | CH$_3$ | F | CH(CH$_3$)$_2$ |
| 31 | 0 | Cl | H | CH$_3$ |
| 32 | 0 | Cl | H | CH$_3$ |
| 33 | 0 | CH$_3$ | CH$_3$ | CH$_2$CH$_3$ |
| 34 | 0 | CH$_3$ | CH$_3$ | cyclopropylmethyl |
| 35 | 1 | CH$_3$ | CH$_3$ | CH$_2$CH$_3$ |
| 36 | 0 | CH$_3$ | CH$_3$ | CH(CH$_3$)$_2$ |
| 37 | 1 | CH$_3$ | CH$_3$ | cyclopropylmethyl |
| 38 | 1 | CH$_3$ | CH$_3$ | CH(CH$_3$)$_2$ |
| 39 | 0 | CH$_3$ | F | CH$_2$CN |
| 40 | 0 | CH$_3$ | CH$_3$ | CH$_2$CN |
| 41 | 0 | CH$_3$ | CH$_3$ | CH$_2$CH(CH$_3$)$_2$ |
| 42 | 0 | CH$_3$ | F | benzyl |
| 43 | 0 | CH$_3$ | F | 3-pyridylmethyl |
| 44 | 1 | CH$_3$ | F | CH$_2$CN |
| 45 | 1 | CH$_3$ | F | benzyl |
| 46 | 1 | CH$_3$ | CH$_3$ | CH$_2$CF$_3$ |
| 47 | 1 | CH$_3$ | CH$_3$ | CH$_2$CF$_3$ |
| 48 | 1 | CH$_3$ | F | N-oxide-3-pyridylmethyl |
| 49 | 1 | CH$_3$ | F | 3-pyridylmethyl |
| 50 | 1 | CH$_3$ | F | CH$_2$CF$_3$ |
| 51 | 1 | CH$_3$ | F | CH$_2$CF$_3$ |
| 52 | 1 | CH$_3$ | CH$_3$ | benzyl |

TABLE 2

Compounds of the formula (I) with substructure (I-A-9)

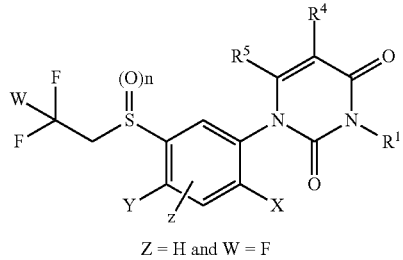

Z = H and W = F

| Ex. No. | n | Y | X | R¹ | R⁴ | R⁵ |
|---|---|---|---|---|---|---|
| 16 | 1 | CH₃ | F | H | CN | CH₃ |
| 17 | 0 | CH₃ | F | H | CN | CH₃ |
| 18 | 1 | CH₂CH₃ | CH₂CH₃ | H | CN | CH₃ |
| 53 | 0 | CH₃ | F | CH₃ | H | H |
| 54 | 1 | CH₃ | F | CH₃ | H | H |
| 55 | 0 | CH₃ | F | H | H | H |
| 56 | 1 | CH₃ | F | H | H | H |
| 57 | 1 | CH₃ | H | CH₃ | H | H |
| 58 | 0 | CH₃ | H | CH₃ | H | H |
| 59 | 1 | CH₃ | F | CH₂CH₃ | H | H |
| 60 | 1 | CH₃ | F | CH₂CF₃ | H | H |
| 61 | 1 | CH₃ | F | CH₂CN | H | H |
| 62 | 1 | CH₃ | F | CH₂-cyclopropyl | H | H |
| 63 | 1 | CH₃ | F | CH(CH₃)₂ | H | H |
| 64 | 1 | CH₃ | F | CH₂-4-fluorophenyl | H | H |
| 65 | 1 | CH₃ | F | CH₂CH=CH₂ | H | H |
| 66 | 1 | CH₃ | F | CH₂CH₂CH₃ | H | H |
| 67 | 1 | CH₃ | F | CH₂CCH | H | H |
| 68 | 1 | CH₃ | F | CH₂OCH₃ | H | H |
| 69 | 1 | CH₃ | F | CH₂CH(CH₃)₂ | H | H |
| 70 | 1 | CH₃ | F | CH₂CHF₂ | H | H |
| 71 | 0 | CH₃ | F | CH₂CH₃ | H | H |
| 72 | 0 | CH₃ | F | CH₂CF₃ | H | H |
| 73 | 0 | CH₃ | F | CH₂CN | H | H |
| 74 | 0 | CH₃ | F | CH₂-cyclopropyl | H | H |
| 75 | 0 | CH₃ | F | CH(CH₃)₂ | H | H |
| 76 | 0 | CH₃ | F | CH₂-4-fluorophenyl | H | H |
| 77 | 0 | CH₃ | F | CH₂CH=CH₂ | H | H |
| 78 | 0 | CH₃ | F | CH₂CH₂CH₃ | H | H |
| 79 | 0 | CH₃ | F | CH₂CCH | H | H |
| 80 | 0 | CH₃ | F | CH₂OCH₃ | H | H |
| 81 | 0 | CH₃ | F | CH₂CH(CH₃)₂ | H | H |
| 82 | 0 | CH₃ | F | CH₂CHF₂ | H | H |
| 83 | 0 | CH₃ | H | CH₂CH₃ | H | H |
| 84 | 0 | CH₃ | H | CH₂CF₃ | H | H |
| 85 | 0 | CH₃ | H | CH₂CN | H | H |
| 86 | 0 | CH₃ | H | CH₂-cyclopropyl | H | H |
| 87 | 0 | CH₃ | H | CH(CH₃)₂ | H | H |
| 88 | 0 | CH₃ | H | H | H | H |
| 89 | 0 | CH₃ | CH₃ | H | H | H |
| 90 | 1 | CH₃ | H | CH₂CF₃ | H | H |
| 91 | 1 | CH₃ | H | H | H | H |
| 92 | 0 | CH₃ | CH₃ | CH₃ | H | H |
| 93 | 1 | CH₃ | CH₃ | CH₃ | H | H |
| 94 | 0 | CH₃ | CH₃ | CH₂CF₃ | H | H |
| 95 | 1 | CH₃ | CH₃ | CH₂CF₃ | H | H |
| 96 | 0 | CH₃ | CH₃ | CH₂CH₃ | H | H |
| 97 | 1 | CH₃ | CH₃ | CH₂CH₃ | H | H |
| 98 | 1 | CH₃ | H | CH₂CH₃ | H | H |
| 99 | 1 | CH₃ | CH₃ | H | H | H |
| 100 | 1 | CH₃ | H | CH₂CN | H | H |

NMR data of the compounds according to Tables 1 and 2:

| Ex. No. | LogP[b] | LogP[a] | 1H NMR δ ppm |
|---|---|---|---|
| 1 | | 1.58 | (D6-DMSO, 400 MHz) 12.45(bs, 1H), 8.02(d, 1H), 7.71(s, 1H), 7.52(d, 1H), 4.34-4.22(m, 1H), 4.04-3.93(m, 1H), 2.43(s, 3H) |
| 2 | | 1.94 | (CDCl₃, 400 MHz) 8.06(d, 1H), 7.58(s, 1H), 7.18(d, 1H), 3.49-3.42(m, 5H), 2.46(s, 3H) |
| 3 | | 2.94 | (CDCl₃, 400 MHz) 7.58-7.56(m, 2H), 7.14(d, 1H), 3.41(s, 3H), 3.35(q, 2H), 2.54(s, 3H) |
| 4 | | 2.01 | (CDCl₃, 400 MHz) 7.88(bs, 1H), 7.56(bs, 1H), 7.25(bs, 1H), 3.48-3.40(m, 5H), 2.41(s, 3H), 2.26(s, 3H) |
| 5 | | 3.08 | (CDCl₃, 400 MHz) 7.55(s, 1H), 7.34(s, 1H), 7.21(s, 1H), 3.42-3.33(m, 5H), 2.49(s, 3H), 2.17(s, 3H) |
| 6 | | 2.73 | (D6-DMSO, 400 MHz) 7.89(s, 2H), 7.40(s, 1H), 4.71-4.64(m, 2H), 4.27-4.21(m, 1H), 3.94-3.87(m, 1H), 2.39(s, 3H), 2.21(s, 3H) |
| 7 | | 3.74 | (CDCl₃, 400 MHz) 7.61(s, 1H), 7.40(s, 1H), 7.22(s, 1H), 4.70(q, 2H), 3.37(q, 2H), 2.49(s, 3H), 2.16(s, 3H) |
| 8 | 1.4 | 2.72 | (CDCl₃, 400 MHz) 8.58(bs, 1H), 7.66(s, 1H), 7.60(s, 1H), 7.57(s, 1H), 3.50(q, 2H) |
| 9 | | 2.65 | (CDCl₃, 400 MHz) 8.08(d, 1H), 7.65(s, 1H), 7.19(d, 1H), 4.68(q, 2H) |
| 10 | | 3.65 | (CDCl₃, 400 MHz) 7.63-7.59(m, 2H), 7.15(d, 1H), 4.68(q, 2H), 3.36(q, 2H), 2.54(s, 3H) |
| 11 | | 3.21 | (CDCl₃, 400 MHz) 8.06(s, 1H), 7.70(s, 1H), 7.66(s, 1H), 4.69(q, 2H), 3.84-3.78(m, 1H), 3.48-3.43(m, 1H) |
| 12 | | 3.93 | (CDCl₃, 400 MHz) 7.66-7.61(m, 3H), 4.68(q, 2H), 3.50(q, 2H) |
| 13 | | 2.48 | (CDCl3, 400 MHz) 8.04(m, 1H), 7.69(m, 1H), 7.59(m, 1H), 3.86-3.75(m, 1H), 3.50-3.39(m, 4H) |
| 14 | | 3.31 | (CDCl₃, 400 MHz) 7.65(s, 1H), 7.59-7.57(m, 2H), 3.49(q, 2H), 3.42(s, 3H) |

-continued

| Ex. No. | LogP[b] | LogP[a] | 1H NMR δ ppm |
|---|---|---|---|
| 15 | 1.1 | 2.02 | (CDCl₃, 400 MHz) 8.66(bs, 1H), 8.06(s, 1H), 7.69(s, 1H), 7.58(s, 1H), 3.86-3.75(m, 1H), 3.52-3.41(m, 1H) |
| 16 | 0.88 | 1.58 | (D6-DMSO, 400 MHz) 12.31(s, 1H), 8.14-8.12(m, 1H), 7.61-7.58(m, 1H), 4.36-3.88(m, 2H), 2.45(s, 3H), 2.20(s, 3H) |
| 17 | | 2.43 | (D6-DMSO, 400 MHz) 12.33(s, 1H), 7.83-7.82(m, 1H), 7.49-7.47(m, 1H), 4.06-3.93(m, 2H), 2.43(s, 3H), 2.13(s, 3H) |
| 18 | 1.55 | 2.15 | (D6-DMSO, 400 MHz) 12.18(s, 1H), 7.96(s, 1H), 7.51(s, 1H), 4.29-3.84(m, 2H), 2.76(m, 2H), 2.51(m, 2H), 2.00(s, 3H), 1.27(t, 3H), 1.15(t, 3H) |
| 19 | 3.27 | 3.31 | (D6-DMSO, 400 MHz) 7.79-7.76(m, 2H), 7.42(d, 1H), 3.96-3.83(m, 4H), 2.45(s, 3H), 1.16(t, 3H) |
| 20 | 4 | 4.03 | (D6-DMSO, 400 MHz) 7.80-7.76(m, 2H), 7.42(d, 1H), 3.92(q, 2H), 3.67(d, 2H), 2.45(s, 3H), 2.07-2.00(m, 1H), 0.89(d, 6H) |
| 21 | 2.22 | 2.24 | (D6-DMSO, 400 MHz) 8.04(d, 1H), 7.80(s, 1H), 7.53(d, 1H), 4.32-4.23(m, 1H), 4.03-3.83(m, 3H), 2.44(s, 3H), 1.67(t, 3H) |
| 22 | 2.9 | 2.92 | (D6-DMSO, 400 MHz) 8.05(d, 1H), 7.81(s, 1H), 7.53(d, 1H), 4.32-4.26(m, 1H), 4.01-3.95(m, 1H), 3.66(d, 2H), 2.43(s, 3H), 2.07-2.01 (m, 1H), 0.89(d, 6H) |
| 23 | 2.83 | 2.9 | (D6-DMSO, 400 MHz) 7.75(s, 1H), 7.67(d, 1H), 7.40-7.32(m, 2H), 3.95(q, 2H), 3.21(s, 3H), 2.41(s, 3H) |
| 24 | 1.83 | 1.84 | (D6-DMSO, 400 MHz) 8.00(d, 1H), 7.79(s, 1H), 7.66(dd, 1H), 7.49(d, 1H), 4.27-4.21(m, 1H), 3.97-3.88(m, 1H), 3.22(s, 3H), 2.41(s, 3H) |
| 25 | 3.76 | 3.79 | (D6-DMSO, 400 MHz) 7.82-7.79(m, 2H), 7.43(d, 1H), 3.93(q, 2H), 3.72(d, 2H), 2.45(s, 3H), 1.19-1.12(m, 1H), 0.50-0.46(m, 2H), 0.36-0.33(m, 2H) |
| 26 | 3.67 | 3.73 | (D6-DMSO, 400 MHz) 7.77(d, 1H), 7.71(s, 1H), 7.41(d, 1H), 4.98-4.91(m, 1H), 3.92(q, 2H), 2.45(s, 3H), 1.41(d, 6H) |
| 27 | 2.65 | 2.72 | (D6-DMSO, 400 MHz) 8.06(d, 1H), 7.83(s, 1H), 7.54(d, 1H), 4.32-4.26(m, 1H), 4.05-3.96(m, 1H), 3.72(d, 2H), 2.44(s, 3H), 1.19-1.13(m, 1H), 0.51-0.46(m, 2H), 0.37-0.33(m, 2H) |
| 28 | 1.9 | 1.95 | (D6-DMSO, 400 MHz) 8.02(d, 1H), 7.81(s, 1H), 7.54(d, 1H), 4.32-3.93(m, m, 2H), 3.21(s, 3H), 2.43(s, 3H) |
| 29 | 1.9 | 1.95 | (D6-DMSO, 400 MHz) 8.02(d, 1H), 7.81(s, 1H), 7.54(d, 1H), 4.32-3.93(m, m, 2H), 3.21(s, 3H), 2.43(s, 3H) |
| 30 | 2.58 | 2.64 | (D6-DMSO, 400 MHz) 8.04(d, 1H), 7.72(s, 1H), 7.52(d, 1H), 4.98-4.91(m, 1H), 4.31-4.25(m, 1H), 4.03-3.94(m, 1H), 2.43(s, 3H), 1.41(d, 6H) |
| 31 | 2.91 | 3 | (D6-DMSO, 400 MHz) 7.82-7.79(m, 2H), 7.67(d, 1H), 7.43(dd, 1H), 4.10(q, 2H), 3.22(s, 3H) |
| 32 | 2.16 | 2.18 | (D6-DMSO, 400 MHz) 8.05(d, 1H), 7.83-7.81(m, 3H), 4.38-4.31(m, 1H), 4.11-4.04(m, 1H), 3.22(s, 3H) |
| 33 | 3.38 | 3.45 | (D6-DMSO, 400 MHz) 7.73(s, 1H), 7.57(s, 1H), 7.28(s, 1H), 3.93-3.83(m, 4H), 2.39(s, 3H), 2.09(s, 3H), 1.17(t, 3H) |
| 34 | 3.87 | 3.94 | (D6-DMSO, 400 MHz) 7.76(s, 1H), 7.59(s, 1H), 7.28(s, 1H), 3.91(q, 2H), 3.72(d, 2H), 2.39(s, 3H), 2.10(s, 3H), 1.19-1.14(m, 1H), 0.50-0.45(m, 2H), 0.37-0.33(m, 2H) |
| 35 | 2.27 | 2.31 | (D6-DMSO, 400 MHz) 7.86(s, 1H), 7.73(s, 1H), 7.38(s, 1H), 4.26-4.10(m, 1H), 3.93-3.83(m, 3H), 2.39(s, 3H), 2.20(s, 3H), 1.24-1.15(m, 3H) |
| 36 | 3.81 | 3.88 | (D6-DMSO, 400 MHz) 7.66(s, 1H), 7.57(s, 1H), 7.27(s, 1H), 5.00-4.93(m, 1H), 3.89(q, 2H), 2.39(s, 3H), 2.09(s, 3H), 1.42(d, 6H) |
| 37 | 2.73 | 2.77 | (D6-DMSO, 400 MHz) 7.87(s, 1H), 7.77(s, 1H), 7.39(s, 1H), 4.25-4.16(m, 1H), 3.95-3.89(m, 1H), 3.72(d, 2H), 2.39(s, 3H), 2.21(s, 3H), 1.20-1.14(m, 1H), 0.50-0.46(m, 2H), 0.37-0.33(m, 2H) |
| 38 | 2.67 | 2.69 | (D6-DMSO, 400 MHz) 7.86(s, 1H), 7.66(s, 1H), 7.37(s, 1H), 4.99-4.92(m, 1H), 4.25-4.18(m, 1H), 3.93-3.87(m, 1H), 2.38(s, 3H), 2.20(s, 3H), 1.42(d, 6H) |
| 39 | 2.9 | 2.96 | (D6-DMSO, 400 MHz) 7.92(s, 1H), 7.77(d, 1H), 7.45(d, 1H); 4.90(s, 2H), 3.90(q, 2H), 3H beneath the DMSO peak |
| 40 | 3.05 | 3.1 | (D6-DMSO, 400 MHz) 7.86(s, 1H), 7.59(s, 1H), 7.30(s, 1H), 4.88(s, 2H), 3.87(q, 2H), 2.33(s, 3H), 2.13(s, 3H) |
| 41 | 4.1 | 4.18 | (D6-DMSO, 400 MHz) 7.75(s, 1H), 7.57(d, 1H); 7.28(d, 1H); 3.93(m, 2H); 3.66(d, 2H); 2.39(s, 3H); 2.09(s, 3H); 2.09(m, 1H); 0.9(d, 6H) |
| 42 | 3.93 | 4.04 | (D6-DMSO, 400 MHz) 7.87(s, 1H), 7.80(d, 1H), 7.42(d, 1H), 7.39-7.27(m, 5H), 5.01(s, 2H), 3.92(q, 2H), 2.45(s, 3H) |
| 43 | 2.87 | 2.36 | (D6-DMSO, 400 MHz) 8.59(s, 1H), 8.51(dd, 1H), 7.87(s, 1H), 7.80-7.76(m, 2H), 7.44-7.36(m, 2H), 5.03(s, 2H), 3.90(q, 2H), 2.45(s, 3H) |

| Ex. No. | LogP[b] | LogP[a] | 1H NMR δ ppm |
|---|---|---|---|
| 44 | 1.96 | 2.02 | (D6-DMSO, 400 MHz) 8.06(d, 1H), 7.93(s, 1H), 7.56(d, 1H), 4.89(s, 2H), 4.34-4.25(m, 1H), 3.99-3.90(m, 1H), 2.44(s, 3H) |
| 45 | 2.9 | 3.00 | (D6-DMSO, 400 MHz) 8.07(d, 1H), 7.88(s, 1H), 7.53(d, 1H), 7.38-7.26(m, 5H), 5.01(s, 2H), 4.31-4.22(m, 1H); 4.06-3.92(m, 1H), 2.43(s, 3H) |
| 46 | 2.66 | 2.72 | (D6-DMSO, 400 MHz) 7.88(d, 2H), 7.40(s, 1H), 4.67(q, 2H), 4.27-4.20(m, 1H), 3.93-3.87(m, 1H), 2.39(s, 3H), 2.21(s, 3H) |
| 47 | 2.66 | 2.72 | (D6-DMSO, 400 MHz) 7.88(d, 2H), 7.40(s, 1H), 4.67(q, 2H), 4.27-4.20(m, 1H), 3.93-3.87(m, 1H), 2.39(s, 3H), 2.21(s, 3H) |
| 48 | 1.45 | 1.51 | (D6-DMSO, 400 MHz) 8.30(s, 1H), 8.14(dd, 1H), 8.07(d, 1H), 7.89(s, 1H), 7.53(d, 1H), 7.41-7.33(m, 2H), 4.97(s, 2H), 4.32-4.23(m, 1H), 4.04-3.89(m, 1H), 2.43(s, 3H) |
| 49 | 2.00 | 1.47 | (D6-DMSO, 400 MHz) 8.61 (d, 1H), 8.49(dd, 1H), 8.07(d, 1H), 7.88(s, 1H); 7.80-7.77(m, 1H), 7.53(d, 1H), 7.37(dd, 1H), 5.03(s, 2H), 4.32-4.22(m, 1H), 4.01-3.95(m, 1H), 2.43(s, 3H) |
| 50 | 2.57 | 2.62 | (D6-DMSO, 400 MHz) 8.06(d, 1H), 7.94(s, 1H), 7.55(d, 1H), 4.68(q, 2H), 4.33-4.24(m, 2H), 4.01-3.95(m, 1H), 2.44(s, 3H) |
| 51 | 2.57 | 2.62 | (D6-DMSO, 400 MHz) 8.06(d, 1H), 7.94(s, 1H), 7.55(d, 1H), 4.68(q, 2H), 4.33-4.24(m, 2H), 4.01-3.95(m, 1H), 2.44(s, 3H) |
| 52 | 3.00 | 3.06 | (D6-DMSO, 400 MHz) 7.89(s, 1H), 7.82(s, 1H), 7.38-7.26(m, 6H), 5.02(s, 2H), 4.25-4.16(m, 1H), 3.93-3.87(m, 1H), 2.38(s, 3H), 2.19(s, 3H) |
| 53 | 2.59 | 2.53 | (D6-DMSO, 400 MHz) 7.77(d, 1H), 7.74(d, 1H), 7.41(d, 1H), 5.88(d, 1H), 3.98(q, 2H), 3.21(s, 3H), 2.43(s, 3H) |
| 54 | 1.66 | 1.61 | (D6-DMSO, 400 MHz) 7.99(d, 1H), 7.78(d, 1H), 7.54(d, 1H), 5.92(d, 1H), 4.30-4.16(m, 1H), 4.12-3.98(m, 1H), 3.21(s, 3H), 2.45(s, 3H) |
| 55 | 2.13 | 2.06 | (D6-DMSO, 400 MHz) 11.58(s, 1H), 7.76(d, 1H), 7.68(d, 1H), 7.39(d, 1H), 5.74-5.71(m, 1H), 3.99(q, 2H), 2.41(s, 3H) |
| 56 | 1.3 | 1.24 | (D6-DMSO, 400 MHz) 11.62(s, 1H), 7.98(d, 1H), 7.74(d, 1H), 7.52(d, 1H), 5.79-5.76(m, 1H), 4.29-4.16(m, 1H), 4.13-4.01(m, 1H), 2.44(s, 3H) |
| 57 | 1.5 | 1.49 | (D6-DMSO, 400 MHz) 7.87(d, 1H), 7.80(d, 1H), 7.61-7.58(m, 1H), 7.49(d, 1H), 5.88(d, 1H), 4.30-4.12(m, 1H), 4.09-3.95(m, 1H), 3.21(s, 3H), 2.42(s, 3H) |
| 58 | 2.48 | 2.39 | (D6-DMSO, 400 MHz) 7.71(d, 1H), 7.61(d, 1H), 7.37(d, 1H), 7.27-7.24(m, 1H), 5.83(d, 1H), 4.04(q, 2H), 3.20(s, 3H), 2.38(s, 3H) |
| 59 | 1.94 | 1.88 | (D6-DMSO, 400 MHz) 8.00(d, 1H), 7.77(d, 1H), 7.53(d, 1H), 5.90(d, 1H), 4.30-4.12(m, 1H), 4.12-3.99(m, 1H), 3.87(q, 2H), 2.45(s, 3H), 1.13(t, 3H) |
| 60 | 2.34 | 2.31 | (D6-DMSO, 400 MHz) 8.04(d, 1H), 7.88(d, 1H), 7.55(d, 1H), 6.02(d, 1H), 4.68(q, 2H), 4.30-4.15(m, 1H), 4.15-4.00(m, 1H), 2.45(s, 3H) |
| 61 | 1.73 | 1.72 | (D6-DMSO, 400 MHz) 8.06(d, 1H), 7.88(d, 1H), 7.56(d, 1H), 6.03(d, 1H), 4.87(s, 2H), 4.32-4.18(m, 1H), 4.10-3.95(m, 1H), 2.45(s, 3H) |
| 62 | 2.37 | 2.29 | (D6-DMSO, 400 MHz) 8.01(d, 1H), 7.79(d, 1H), 7.53(d, 1H), 5.93(d, 1H), 4.30-4.15(m, 1H), 4.15-4.00(m, 1H), 3.73(d, 2H), 2.45(s, 3H), 1.21-1.10(m, 1H), 0.49-0.40(m, 2H), 0.35-0.30(m, 2H) |
| 63 | 2.31 | 2.22 | (D6-DMSO, 400 MHz) 7.99(d, 1H), 7.73(d, 1H), 7.52(d, 1H), 5.85(d, 1H), 5.10-5.00(m, 1H), 4.30-4.15(m, 1H), 4.15-4.00(m, 1H), 2.45(s, 3H), 1.39(d, 6H) |
| 64 | 2.77 | 2.68 | (D6-DMSO, 400 MHz) 8.03(d, 1H), 7.83(d, 1H), 7.53(d, 1H), 7.38-7.35(m, 2H), 7.18-7.13(m, 2H), 5.97(d, 1H), 5.00(s, 2H), 4.30-4.15(m, 1H), 4.15-3.99(m, 1H), 2.44(s, 3H) |
| 65 | 2.08 | 2.01 | (D6-DMSO, 400 MHz) 8.02(d, 1H), 7.81(d, 1H), 7.53(d, 1H), 5.94(d, 1H), 5.90-5.80(m, 1H), 5.18-5.08(m, 2H), 4.44(d, 2H), 4.29-4.15(m, 1H), 4.15-4.00(m, 1H), 2.45(s, 3H) |
| 66 | 2.25 | 2.17 | (D6-DMSO, 400 MHz) 8.00(d, 1H), 7.78(d, 1H), 7.53(d, 1H), 5.91(d, 1H), 4.30-4.15(m, 1H), 4.15-4.00(m, 1H), 3.79(t, 2H), 2.45(s, 3H), 1.62-1.50(m, 2H), 0.87(t, 3H) |
| 67 | 1.92 | 1.86 | (D6-DMSO, 400 MHz) 8.03(d, 1H), 7.84(d, 1H), 7.55(d, 1H), 5.97(d, 1H), 4.57(d, 2H), 4.30-4.15(m, 1H), 4.15-4.00(m, 1H), 3.16(t, 1H), 2.45(s, 3H) |
| 68 | 1.74 | 1.67 | (D6-DMSO, 400 MHz) 8.03(d, 1H), 7.82(d, 1H), 7.54(d, 1H), 5.94(d, 1H), 5.22(s, 2H), 4.31-4.19(m, 1H), 4.15-3.99(m, 1H), 3.31(s, 3H), 2.45(s, 3H) |

| Ex. No. | LogP[b] | LogP[a] | 1H NMR δ ppm |
|---|---|---|---|
| 69 | 2.55 | 2.48 | (D6-DMSO, 400 MHz) 8.01(d, 1H), 7.79(d, 1H), 7.52(d, 1H), 5.91(d, 1H), 4.29-4.15(m, 1H), 4.15-4.00(m, 1H), 3.68(d, 2H), 2.45(s, 3H), 2.10-1.98(m, 1H), 0.86(d, 6H) |
| 70 | 2.11 | 2.06 | (D6-DMSO, 400 MHz) 8.03(d, 1H), 7.85(d, 1H), 7.55(d, 1H), 6.40-6.07(m, 1H), 5.87(d, 1H), 4.30-4.15(m, 3H), 4.11-3.98(m, 1H), 2.45(s, 3H) |
| 71 | 2.93 | 2.86 | (D6-DMSO, 400 MHz) 7.78(d, 1H), 7.72(d, 1H), 7.41(d, 1H), 5.86(d, 1H), 3.99(q, 2H), 3.86(q, 2H), 2.42(s, 3H), 1.12(t, 3H) |
| 72 | 3.29 | 3.16 | (D6-DMSO, 400 MHz) 7.84(d, 1H), 7.80(d, 1H), 7.43(d, 1H), 5.98(d, 1H), 4.68(q, 2H), 4.00(q, 2H), 2.43(s, 3H) |
| 73 | 2.65 | 2.62 | (D6-DMSO, 400 MHz) 7.85(d, 1H), 7.82(d, 1H), 7.45(d, 1H), 6.01(d, 1H), 4.88(s, 2H), 3.98(q, 2H), 2.44(s, 3H) |
| 74 | 3.38 | 3.24 | (D6-DMSO, 400 MHz) 7.80(d, 1H), 7.72(d, 1H), 7.41(d, 1H), 5.88(d, 1H), 4.01(q, 2H), 3.73(d, 2H), 2.42(s, 3H), 1.19-1.10(m, 1H), 0.49-0.40(m, 2H), 0.36-0.28(m, 2H) |
| 75 | 3.35 | 3.21 | (D6-DMSO, 400 MHz) 7.77(d, 1H), 7.68(d, 1H), 7.40(d, 1H), 5.81(d, 1H), 5.11-5.01(m, 1H), 4.00(q, 2H), 2.42(s, 3H), 1.38(d, 6H) |
| 76 | 3.74 | 3.56 | (D6-DMSO, 400 MHz) 7.81(d, 1H), 7.78(d, 1H), 7.43-7.34(m, 3H), 7.19-7.13(m, 2H), 5.93(d, 1H), 5.00(s, 2H), 3.99(q, 2H), 2.42(s, 3H) |
| 77 | 3.06 | 3.08 | (D6-DMSO, 400 MHz) 7.79(d, 1H), 7.76(d, 1H), 7.41(d, 1H), 5.89(d, 1H), 5.88-5.78(m, 1H), 5.15-5.08(m, 2H), 4.43(d, 2H), 4.00(q, 2H), 2.42(s, 3H) |
| 78 | 3.27 | 3.13 | (D6-DMSO, 400 MHz) 7.78(d, 1H), 7.72(d, 1H), 7.41 (d, 1H), 5.87(d, 1H), 3.99(q, 2H), 3.81-3.76(m, 2H), 2.42(s, 3H), 1.61-1.50(m, 2H), 0.87(t, 3H) |
| 79 | 2.81 | 2.78 | (D6-DMSO, 400 MHz) 7.82-7.78(m, 2H), 7.43(d, 1H), 5.93(d, 1H), 4.57(d, 2H), 4.00(q, 2H), 3.17(t, 1H), 2.43(s, 3H) |
| 80 | 2.66 | 2.62 | (D6-DMSO, 400 MHz) 7.80(d, 1H), 7.77(d, 1H), 7.42 (d, 1H), 5.89(d, 1H), 5.22(s, 2H), 4.00(q, 2H), 3.31(s, 3H), 2.43(s, 3H) |
| 81 | 3.62 | 3.56 | (D6-DMSO, 400 MHz) 7.78(d, 1H), 7.73(d, 1H), 7.40(d, 1H), 5.87(d, 1H), 4.00(q, 2H), 3.68(d, 2H), 2.42(s, 3H), 2.07-1.97(m, 1H), 0.86(d, 6H) |
| 82 | 3.06 | 2.99 | (D6-DMSO, 400 MHz) 7.83-7.78(m, 2H), 7.43(d, 1H), 6.38-6.07(m, 1H), 5.95(d, 1H), 4.32-4.23(m, 2H), 3.99(q, 2H), 2.43(s, 3H) |
| 83 | 2.81 | 2.74 | (D6-DMSO, 400 MHz) 7.70(d, 1H), 7.61(d, 1H), 7.37(d, 1H), 7.29-7.25(m, 1H), 5.81(d, 1H), 4.05(q, 2H), 3.87(q, 2H), 1.18(t, 3H), 1.13(t, 3H) |
| 84 | 3.15 | 3.16 | (D6-DMSO, 400 MHz) 7.81(d, 1H), 7.63(d, 1H), 7.39(d, 1H), 7.30-7.26(m, 1H), 5.92(d, 1H), 4.67(q, 2H), 4.05(q, 2H), 2.39(s, 3H) |
| 85 | 2.62 | 2.55 | (D6-DMSO, 400 MHz) 7.82(d, 1H), 7.65(d, 1H), 7.40(d, 1H), 7.31-7.28(m, 1H), 5.94(d, 1H), 4.86(s, 2H), 4.04(q, 2H), 2.39(s, 3H) |
| 86 | 3.31 | 3.21 | (D6-DMSO, 400 MHz) 7.72(d, 1H), 7.62(d, 1H), 7.37(d, 1H), 7.30-7.26(m, 1H), 5.83(d, 1H), 4.05(q, 2H), 3.72(d, 2H), 2.38(s, 3H), 1.19-1.12(m, 1H), 0.50-0.42(m, 2H), 0.40-0.32(m, 2H) |
| 87 | 3.25 | 3.18 | (D6-DMSO, 400 MHz) 7.66(d, 1H), 7.60(d, 1H), 7.36(d, 1H), 7.27-7.23(m, 1H), 5.75(d, 1H), 5.11-5.04(m, 1H), 4.05(q, 2H), 2.38(s, 3H), 1.39(d, 6H) |
| 88 | 2.05 | 1.99 | (D6-DMSO, 400 MHz) 11.45(s, 1H), 7.67(d, 1H), 7.59(d, 1H), 7.36(d, 1H), 7.26-7.23(m, 1H), 5.70-5.66(m, 1H), 4.05(q, 2H), 2.37(s, 3H) |
| 89 | 2.25 | 2.18 | (D6-DMSO, 400 MHz) 11.46(s, 1H), 7.54(d, 1H), 7.52(s, 1H), 7.27(s, 1H), 5.70-5.66(m, 1H), 3.98(q, 2H), 2.36(s, 3H), 2.07(s, 3H) |
| 90 | 2.21 | 2.18 | (D6-DMSO, 400 MHz) 7.90(d, 1H), 7.88(s, 1H), 7.62-7.59(m, 1H), 7.51(d, 1H), 5.97(d, 1H), 4.67(q, 2H), 4.26-4.14(m, 1H), 4.09-3.97(m, 1H), 2.43(s, 3H) |
| 91 | 1.19 | 1.20 | (D6-DMSO, 400 MHz) 11.50(s, 1H), 7.85(d, 1H), 7.77(d, 1H), 7.62-7.57(m, 1H), 7.48(d, 1H), 5.74(d, 1H), 4.23-3.98(m, 2H), 2.42(s, 3H) |
| 92 | 2.72 | 2.66 | (D6-DMSO, 400 MHz) 7.59(d, 1H), 7.53(s, 1H), 7.28(s, 1H), 5.83(d, 1H), 3.96(q, 2H), 3.21(s, 3H), 2.37(s, 3H), 2.07(s, 3H) |
| 93 | 1.7 | 1.68 | (D6-DMSO, 400 MHz) 7.77(d, 1H), 7.64(t, 1H), 7.40, (d, 1H), 5.90-5.84(m, 1H), 4.28-3.89(m, 2H), 3.21(d, 3H), 2.39(s, 3H), 2.17(s, 3H) |
| 94 | 3.49 | 3.39 | (D6-DMSO, 400 MHz) 7.70(d, 1H), 7.56(s, 1H), 7.29(s, 1H), 5.93(d, 1H), 4.76-4.60(m, 2H), 3.97(q, 2H), 2.37(s, 3H), 2.06(s, 3H) |
| 95 | 2.44 | 2.40 | (D6-DMSO, 400 MHz) 7.81(d, 1H), 7.75(t, 1H), 7.42(d, 1H), 6.00-5.93(m, 1H), 4.74-4.61(m, 2H), 4.29-3.90(m, 2H), 2.40(s, 3H), 2.17(s, 3H) |

| Ex. No. | LogP[b] | LogP[a] | 1H NMR δ ppm |
| --- | --- | --- | --- |
| 96 | 3.07 | 2.98 | (D6-DMSO, 400 MHz) 7.58(d, 1H), 7.54(s, 1H), 7.28(s, 1H), 5.81(d, 1H), 4.02-3.91(m, 2H), 3.90-3.81(m, 2H), 2.37(s, 3H), 2.06(s, 3H), 1.13(t, 3H) |
| 97 | 1.99 | 1.96 | (D6-DMSO, 400 MHz) 7.77(d, 1H), 7.65-7.61(m, 1H), 7.40(d, 1H), 5.89-5.82(m, 1H), 4.29-3.82(m, 4H), 2.40(s, 3H), 2.16(s, 3H), 1.18-1.10(m, 3H) |
| 98 | 1.77 | 1.77 | (D6-DMSO, 400 MHz) 7.87(d, 1H), 7.79(d, 1H), 7.62-7.58(m, 1H), 7.49(d, 1H), 5.86(d, 1H), 4.26-4.12(m, 1H), 4.10-3.97(m, 1H), 3.88(q, 2H), 2.42(s, 3H), 1.34(t, 3H) |
| 99 | 1.38 | 1.35 | (D6-DMSO, 400 MHz) 11.52(s, 1H), 7.75(d, 1H), 7.62-7.57(m, 1H), 7.39(d, 1H), 5.76-5.69(m, 1H), 4.28-3.93(m, 2H), 2.39(s, 3H), 2.17(s, 3H) |
| 100 | 1.62 | 1.63 | (D6-DMSO, 400 MHz) 7.93(d, 1H), 7.89(d, 1H), 7.64-7.60(m, 1H), 7.51(d, 1H), 5.98(d, 1H), 4.86(s, 2H), 4.27-4.15(m, 1H), 4.07-3.95(m, 1H), 2.43(s, 3H) |

The optical rotations were determined on a Perkin Elmer 341, serial number 9123, at a wavelength of 589 nm and a temperature of 20° C., by the following formula:

$$(\text{specific optical rotation } \alpha)_D^{\circ C.} = \frac{\text{angle of rotation } \alpha * \text{solution volume (ml)}}{\text{path length (dm)} * \text{sample weight (g)}}$$

The specific optical rotations below should be understood as an average from 5 different measurements:

| | |
| --- | --- |
| 28 | −34.7 in CHCl$_3$ (c = 0.009) |
| 29 | 33.7 in CHCl$_3$ (c = 0.009) |
| 46 | −31.9 in CHCl$_3$ (c = 0.009) |
| 47 | 31.9 in CHCl$_3$ (c = 0.009) |
| 50 | −28.8 in CHCl$_3$ (c = 0.009) |
| 51 | 28.2 in CHCl$_3$ (c = 0.009) |

USE EXAMPLES

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 μl of the solution are distributed homogeneously on the inner walls and base of a 25 ml test tube by turning and rocking on an orbital shaker (rocking rotation at 30 rpm for 2 h). With 900 ppm active ingredient solution and internal surface 44.7 cm$^2$, given homogeneous distribution, an area-based dose of 5 μg/cm$^2$ is achieved.

After the solvent has been evaporated off, the tubes are populated with 5-10 adult cat fleas (*Ctenocephalides felis*), sealed with a perforated plastic lid and incubated in a horizontal position at room temperature and ambient humidity. After 48 h, the efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if an efficacy of at least 80% was achieved at an application rate of 5 μg/cm$^2$ in this test. 100% efficacy means that all the fleas were dead or moribund. 0% efficacy means that no fleas were harmed.

In this test, for example, the following compound from the preparation examples showed an efficacy of 100% at an application rate of 5 μg/cm$^2$ (=500 g/ha): 2

*Boophilus microplus*—Injection Test

Solvent: dimethyl sulphoxide

To produce an appropriate active ingredient formulation, 10 mg of active ingredient are mixed with 0.5 ml of solvent and the concentrate is diluted with solvent to the desired concentration.

1 μl of the active ingredient solution is injected into the abdomen of 5 engorged adult female cattle ticks (*Boophilus microplus*). The animals are transferred into dishes and kept in a climate-controlled room.

The efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples showed an efficacy of 100% at an application rate of 20 μg/animal: 2, 3, 4, 6, 9, 10, 11, 19, 20, 21, 22, 54, 29

*Meloidogyne incognita* Test

Solvent: 125.0 parts by weight of acetone

To produce an appropriate active ingredient formulation, 1 part by weight of active ingredient is mixed with the stated amount of solvent and the concentrate is diluted with water to the desired concentration.

Vessels are filled with sand, active ingredient solution, an egg/larvae suspension of the southern root-knot nematode (*Meloidogyne incognita*) and lettuce seeds. The lettuce seeds germinate and the plants develop. The galls develop on the roots After 14 days, the nematicidal efficacy in % is determined by the formation of galls. 100% means that no galls were found; 0% means that the number of galls on the treated plants corresponds to the untreated control.

In this test, for example, the following compounds from the preparation examples showed an efficacy of 100% at an application rate of 20 ppm: 9, 10, 21, 25, 27, 30, 53, 54, 58, 59, 60, 61, 62, 63, 64, 65, 67, 68, 69, 70, 71, 72, 73, 74, 75, 76, 77, 78, 79, 80, 82, 84, 90, 95, 98, 100

In this test, for example, the following compounds from the preparation examples showed an efficacy of 90% at an application rate of 20 ppm: 2, 3, 8, 11, 12, 14, 15, 19, 20, 22, 39, 56, 57, 85, 86, 87, 92, 97

*Myzus persicae*—Spray Test
  Solvent: 78 parts by weight of acetone
  1.5 parts by weight of dimethylformamide
  Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 6 days, the efficacy in % is determined 100% means that all the aphids have been killed; 0% means that none of the aphids have been killed.

In this test, for example, the following compounds from the preparation examples showed an efficacy of 90% at an application rate of 500 g/ha: 32, 43, 44, 48, 49

*Phaedon cochleariae*—Spray Test
  Solvent: 78.0 parts by weight of acetone
  1.5 parts by weight of dimethylformamide
  Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples showed an efficacy of 100% at an application rate of 500 g/ha: 25, 27, 60, 79

In this test, for example, the following compound from the preparation examples showed an efficacy of 83% at an application rate of 500 g/ha: 10

*Tetranychus urticae*—Spray Test, OP-Resistant
  Solvent: 78.0 parts by weight of acetone
  1.5 parts by weight of dimethylformamide
  Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that none of the spider mites have been killed.

In this test, for example, the following compounds from the preparation examples showed an efficacy of 100% at an application rate of 500 g/ha: 3, 4, 5, 9, 11, 14, 19, 20, 21, 22, 23, 24, 25, 26, 27, 30, 32, 33, 34, 35, 36, 37, 38, 39, 40, 42, 54, 55, 56, 84, 85, 86, 87, 89, 90, 91, 93, 94, 95, 96, 97, 98, 99

In this test, for example, the following compounds from the preparation examples showed an efficacy of 90% at an application rate of 500 g/ha: 2, 6, 7, 10, 12, 13, 16, 17, 18, 41, 43, 53, 58, 59, 61, 62, 63, 66, 68, 70, 71, 72, 73, 74, 76, 77, 78, 79, 81, 88, 92, 100

In this test, for example, the following compounds from the preparation examples showed an efficacy of 100% at an application rate of 100 g/ha: 31

In this test, for example, the following compounds from the preparation examples showed an efficacy of 90% at an application rate of 100 g/ha: 52, 64, 65, 75

In this test, for example, the following compound from the preparation examples showed an efficacy of 90% at an application rate of 20 g/ha: 67

*Meloidogyne incognita* Test
  Solvent: 7 parts by weight of dimethylformamide
  Emulsifier: 2.5 parts by weight of alkylaryl polyglycol ether To produce an appropriate active ingredient formulation, 1 part by weight of active ingredient is mixed with the stated amounts of solvent and emulsifier, and the concentrate is diluted with water to the desired concentration, it being necessary to include the volume of soil which is drenched in the calculation. It should be noted that a concentration of 20 ppm of emulsifier in the soil is not exceeded. To produce further test concentrations, water is used for dilution.

Pots filled with soil (loamy sand) are watered with the active ingredient solution. An egg/larvae suspension of the southern root-knot nematode (*Meloidogyne incognita*) is added, lettuce seeds are scattered over the surface of the soil, and they are covered over with quartz sand. The lettuce seeds germinate and the plants develop. The galls develop on the roots After 21 days, the nematicidal efficacy in % is determined by the formation of galls. 100% means that no galls have been found; 0% means that the number of galls on the treated plants corresponds to the untreated control.

In this test, for example, the following compound from the preparation examples showed an efficacy of 100% at an application rate of 8 ppm: 29

In this test, for example, the following compound from the preparation examples showed an efficacy of 99% at an application rate of 8 ppm: 50

*Myzus persicae*—Spray Test
  Solvent: 7 parts by weight of dimethylformamide
  Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bell pepper plants (*Capsicum annuum*) heavily infested by the green peach aphid (*Myzus persicae*) are treated by spraying with the active ingredient formulation in the desired concentration.

After 6 days, the kill in % is determined. 100% means that all the aphids have been killed; 0% means that no aphids have been killed.

In this test, for example, the following compound from the preparation examples showed an efficacy of 97% at an application rate of 20 ppm: 31

*Tetranychus urticae*—Spray Test, OP-Resistant

Solvent: 7 parts by weight of dimethylformamide
Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bean plants (*Phaseolus vulgaris*) heavily infested by all stages of the greenhouse red spider mite (*Tetranychus urticae*) are treated by spraying with the active ingredient formulation in the desired concentration.

After 7 days, the efficacy in % is determined. 100% means that all the spider mites have been killed; 0% means that none of the spider mites have been killed.

In this test, for example, the following compounds from the preparation examples showed an efficacy of 100% at an application rate of 20 ppm: 29, 47, 50, 60, 80, 82

In this test, for example, the following compound from the preparation examples showed an efficacy of 95% at an application rate of 20 ppm: 44

In this test, for example, the following compound from the preparation examples showed an efficacy of 90% at an application rate of 20 ppm: 45

The invention claimed is:

1. A compound of formula (I)

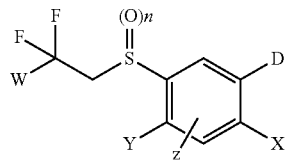

(I)

wherein

D is a substructure of formula (I-A)

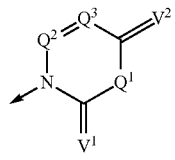

(I-A)

in which the ring nitrogen of substructure D is bonded to the six-membered ring in formula (I) and the arrow represents the bond to the six-membered ring;

$V^1$ and $V^2$ are each independently oxygen or $N-R^{11}$;
$Q^1$ is $N-R^1$;
$Q^3$ is $CR^4$ or nitrogen;
$Q^4$ is $CR^5$ or nitrogen;
$R^1$ is hydrogen;
or is $(C_1-C_6)$alkyl, $(C_3-C_8)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl, phenyl$(C_1-C_3)$alkyl or pyridyl$(C_1-C_3)$alkyl, where the aforementioned radicals are each optionally mono- to trisubstituted by halogen, cyano, nitro, hydroxyl, amino, $(C_1-C_6)$alkyl, halo-$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where the nitrogen atom present in pyridyl$(C_1-C_3)$alkyl is optionally in the form of the N-oxide;

or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyridyl, pyrimidyl, pyridazinyl, pyrazinyl, triazinyl, thiazolyl, thiazadiazolyl, oxazolyl, oxadiazolyl, pyrazolyl, or triazolyl, where the aforementioned radicals are each optionally mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where the nitrogen atom present in pyridyl is optionally in the form of the N-oxide;

$R^4$ and $R^5$ are each independently hydrogen, halogen, $(C_1-C_4)$alkyl, $(C_1-C_4)$haloalkyl, cyano$(C_1-C_6)$alkyl, $(C_3-C_6)$cycloalkyl, cyano or carboxyl;

$R^{11}$ is hydrogen, $(C_1-C_4)$alkyl, $(C_1-C_4)$haloalkyl, cyano $(C_1-C_6)$alkyl or $(C_3-C_6)$cycloalkyl;

W is hydrogen or fluorine;

n is 0 or 1;

X and Y are each independently hydrogen, fluorine, chlorine, bromine, methyl, ethyl, trifluoromethyl, difluoromethyl, difluoromethoxy, trifluoromethoxy, cyclopropyl, cyano, amino, hydroxyl or nitro; and Z is hydrogen.

2. The compound according to claim 1 wherein

D is a substructure of the formula (I-A);
$V^1$ and $V^2$ are each independently oxygen;
$Q^1$ is $N-R^1$;
$Q^3$ is $CR^4$;
$Q^4$ is $CR^5$ or nitrogen;
$R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, $CH_2CCH$, cyclopropylmethyl, trifluoroethyl, 2,2-difluoroethyl, $CH_2CN$, $CH_2OCH_3$, $CH_2CH_2OCH_3$, benzyl, cyclopropyl, cyclobutyl, phenyl, 2-fluorophenylmethyl, 3-fluorophenylmethyl, 4-fluorophenylmethyl, 2-pyridylmethyl, N-oxide-2-pyridylmethyl, 3-pyridylmethyl, N-oxide-3-pyridylmethyl, 4-pyridylmethyl or N-oxide-4-pyridylmethyl;

$R^4$ and $R^5$ are each independently hydrogen, methyl, ethyl, tert-butyl, trifluoromethyl, methoxy, trifluoromethoxy, cyclopropyl, cyano or carboxyl;

W is hydrogen or fluorine;

n is 0 or 1;

X is hydrogen, chlorine, fluorine, methyl or ethyl;

Y is chlorine, bromine, cyano, methyl, ethyl, trifluoromethyl, fluorine or methoxy; and Z is hydrogen.

3. The compound according to claim 1, wherein
D is a substructure which is selected from the group consisting of

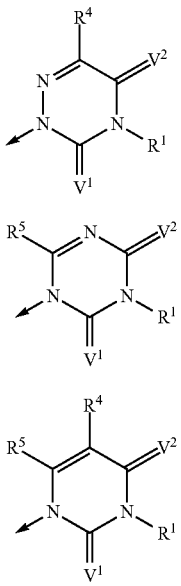

(I-A-I)

(I-A-II)

(I-A-III)

$V^1$ and $V^2$ are each independently oxygen or N—$R^{11}$;
$R^1$ is hydrogen;
  or is $(C_1-C_6)$alkyl, $(C_3-C_8)$cycloalkyl$(C_1-C_3)$alkyl, halo$(C_1-C_6)$alkyl, cyano$(C_1-C_6)$alkyl, hydroxyalkyl, $(C_1-C_6)$alkoxy$(C_1-C_6)$alkyl, phenyl$(C_1-C_3)$alkyl, or pyridyl-$(C_1-C_3)$alkyl, where the aforementioned radicals are optionally mono- to trisubstituted by halogen, cyano, nitro, hydroxyl, amino, $(C_1-C_6)$ alkyl, halo$(C_1-C_6)$alkyl, $(C_1-C_6)$alkoxy, halo$(C_1-C_6)$ alkoxy, $(C_1-C_6)$alkylsulphinyl, $(C_1-C_6)$alkylsulphanyl, $(C_1-C_6)$alkylsulphonyl, halo$(C_1-C_6)$ alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where one of the nitrogen atoms present in pyridyl $(C_1-C_3)$alkyl is optionally in the form of the N-oxide;
  or is $(C_3-C_6)$cycloalkyl or $(C_3-C_6)$cycloalkenyl, azetidinyl, azolidinyl, azinanyl, oxetanyl, oxolanyl, oxanyl, thiethanyl, thiolanyl, or thianyl;
  or is phenyl that is optionally mono- to trisubstituted by halogen, cyano, nitro, hydroxyl, amino, $(C_1-C_6)$ alkyl, halo$(C_1-C_6)$alkyl, $(C_1-C_6)$alkoxy, halo-$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$ alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, or is hetaryl selected from the group consisting of pyridyl, pyrimidyl, pyridazinyl, pyrazinyl, triazinyl, thiazolyl, thiazadiazolyl, oxazolyl, oxadiazolyl, pyrazolyl, and triazolyl, where the hetaryl is optionally mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, halo$(C_1-C_6)$alkylsulphinyl, halo$(C_1-C_6)$alkylsulphanyl, halo-$(C_1-C_6)$alkylsulphonyl or optionally methyl-, fluorine-, chlorine-, or cyano-substituted cyclopropyl, and where one of the nitrogen atoms present in hetaryl is optionally in the form of the N-oxide;
$R^4$ and $R^5$ are each independently hydrogen, halogen, cyano, $(C_1-C_4)$alkyl, $(C_3-C_6)$cycloalkyl, $(C_1-C_4)$haloalkyl, cyano$(C_1-C_6)$alkyl, or carboxyl;
$R^{11}$ is hydrogen, $(C_1-C_4)$alkyl, $(C_3-C_6)$cycloalkyl, $(C_1-C_4)$haloalkyl, or cyano$(C_1-C_6)$alkyl;
W is hydrogen or fluorine;
n is 0 or 1; and
X and Y are each independently hydrogen, fluorine, chlorine, bromine, cyano, nitro, amino, hydroxyl, methyl, ethyl, trifluoromethyl, difluoromethyl, difluoromethoxy, trifluoromethoxy or cyclopropyl; and
Z is hydrogen.
4. The compound according to claim 3, wherein D is a substructure of the formula (I-A-I).
5. The compound according to claim 3, wherein D is a substructure of the formula (I-A-II).
6. The compound according to claim 3, wherein D is a substructure of the formula (I-A-III).
7. The compound according to claim 1, wherein D is a substructure of the formula (I-A-1)

(I-A-1)

in which
$R^1$ is hydrogen;
  or is $(C_1-C_6)$alkyl, $(C_3-C_8)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl, phenyl$(C_1-C_3)$alkyl or pyridyl$(C_1-C_3)$alkyl, where the aforementioned radicals are each optionally mono- to trisubstituted by halogen, cyano, nitro, hydroxyl, amino, $(C_1-C_6)$alkyl, halo-$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where the nitrogen atom present in pyridyl$(C_1-C_3)$alkyl is optionally in the form of the N-oxide;
  or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyridyl, pyrimidyl, pyridazinyl, pyrazinyl, triazinyl, thiazolyl, thiazadiazolyl, oxazolyl, oxadiazolyl, pyrazolyl, or triazolyl, where the aforementioned radicals are each optionally mono- to trisubstituted by halogen, cyano, nitro, hydroxyl, amino, $(C_1-C_6)$alkyl, halo$(C_1-C_6)$ alkyl, $(C_1-C_6)$alkoxy, halo$(C_1-C_6)$alkoxy, $(C_1-C_6)$ alkylsulphinyl, $(C_1-C_6)$alkylsulphanyl, $(C_1-C_6)$ alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where the nitrogen atom present in pyridyl is optionally in the form of the N-oxide;

$R^4$ is hydrogen, halogen, $(C_1-C_4)$alkyl, $(C_1-C_4)$haloalkyl, cyano$(C_1-C_6)$alkyl, $(C_3-C_6)$cycloalkyl, cyano or carboxyl;

W is hydrogen or fluorine;

n is 0 or 1;

X and Y are each independently hydrogen, fluorine, chlorine, bromine, methyl, ethyl, trifluoromethyl, difluoromethyl, difluoromethoxy, trifluoromethoxy, cyclopropyl, cyano, amino, hydroxyl or nitro; and Z is hydrogen.

8. The compound according to claim 1 wherein D is a substructure of the formula (I-A-5)

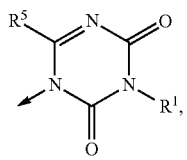

(I-A-5)

in which $R^1$ is hydrogen;

or is $(C_1-C_6)$alkyl, $(C_3-C_8)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl, phenyl$(C_1-C_3)$alkyl or pyridyl$(C_1-C_3)$alkyl, where the aforementioned radicals are each optionally mono- to trisubstituted by halogen, cyano, nitro, hydroxyl, amino, $(C_1-C_6)$alkyl, halo-$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where the nitrogen atom present in pyridyl$(C_1-C_3)$alkyl is optionally in the form of the N-oxide;

or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyridyl, pyrimidyl, pyridazinyl, pyrazinyl, triazinyl, thiazolyl, thiazadiazolyl, oxazolyl, oxadiazolyl, pyrazolyl, or triazolyl, where the aforementioned radicals are each optionally mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where the nitrogen atom present in pyridyl is optionally in the form of the N-oxide;

$R^5$ is hydrogen, halogen, $(C_1-C_4)$alkyl, $(C_1-C_4)$haloalkyl, cyano$(C_1-C_6)$alkyl, $(C_3-C_6)$cycloalkyl, cyano or carboxyl;

W is hydrogen or fluorine;

n is 0 or 1;

X and Y are each independently hydrogen, fluorine, chlorine, bromine, methyl, ethyl, trifluoromethyl, difluoromethyl, difluoromethoxy, trifluoromethoxy, cyclopropyl, cyano, amino, hydroxyl or nitro; and Z is hydrogen.

9. The compound according to any of claim 1 wherein D is a substructure of the formula (I-A-9)

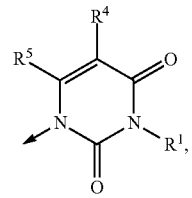

(I-A-9)

in which $R^1$ is hydrogen;

or is $(C_1-C_6)$alkyl, $(C_3-C_8)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl, phenyl$(C_1-C_3)$alkyl or pyridyl$(C_1-C_3)$alkyl, where the aforementioned radicals are each optionally mono- to trisubstituted by halogen, cyano, nitro, hydroxyl, amino, $(C_1-C_6)$alkyl, halo-$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where the nitrogen atom present in pyridyl$(C_1-C_3)$alkyl is optionally in the form of the N-oxide;

or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyridyl, pyrimidyl, pyridazinyl, pyrazinyl, triazinyl, thiazolyl, thiazadiazolyl, oxazolyl, oxadiazolyl, pyrazolyl, or triazolyl, where the aforementioned radicals are each optionally mono- to trisubstituted by halogen, cyano, nitro, hydroxyl, amino, $(C_1-C_6)$alkyl, halo$(C_1-C_6)$ alkyl, $(C_1-C_6)$alkoxy, halo$(C_1-C_6)$alkoxy, $(C_1-C_6)$ alkylsulphinyl, $(C_1-C_6)$alkylsulphanyl, $(C_1-C_6)$ alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, or cyano-substituted cyclopropyl, and where the nitrogen atom present in pyridyl is optionally in the form of the N-oxide;

$R^4$ and $R^5$ are each independently hydrogen, halogen, $(C_1-C_4)$alkyl, $(C_1-C_4)$haloalkyl, cyano$(C_1-C_6)$alkyl, $(C_3-C_6)$cycloalkyl, cyano or carboxyl;

W is hydrogen or fluorine;

n is 0 or 1;

X and Y are each independently hydrogen, fluorine, chlorine, bromine, methyl, ethyl, trifluoromethyl, difluoromethyl, difluoromethoxy, trifluoromethoxy, cyclopropyl, cyano, amino, hydroxyl or nitro; and Z is hydrogen.

10. An agrochemical formulation, comprising at least one compound of formula (I) according to claim 1.

11. The formulation according to claim 10, further comprising at least one extender and/or at least one surface-active substance.

12. The formulation according to claim 10, wherein the compound of formula (I) is in a mixture with at least one further active ingredient.

13. A method for controlling an animal pest, comprising applying a compound of formula (I) according to claim 1 to one or more pests and/or a habitat thereof.

14. The method according to claim 13, wherein the animal pest is an insect, an acarid or a nematode.

15. The method according to claim 13 comprising applying the compound of formula (I) to crops or habitat thereof.

16. The method according to claim 13 comprising applying the compound of formula (I) to an animal or habitat thereof.

17. A method for protecting seed and/or a germinating plant from one or more animal pests comprising contacting said seed or plant with a compound of the formula (I) according to claim 1.

18. A seed obtained by the method according to claim 17.

* * * * *